United States Patent [19]

Yanagibashi et al.

[11] Patent Number: 5,397,781

[45] Date of Patent: Mar. 14, 1995

[54] PYRIMIDINE DERIVATIVES

[75] Inventors: Kazutoshi Yanagibashi; Kiyoshi Mizuguchi; Shuhei Ohnishi; Kimihiro Murakami, all of Tokyo, Japan

[73] Assignee: Mochida Pharmaceutical Company, Limited, Tokyo, Japan

[21] Appl. No.: 16,286

[22] Filed: Feb. 11, 1993

[30] Foreign Application Priority Data

Mar. 18, 1992 [JP] Japan .................. 4-062380

[51] Int. Cl.⁶ ............... A61K 31/505; C07D 239/42; C07D 239/50; C07D 239/48
[52] U.S. Cl. ..................... 514/256; 514/232.2; 514/235.8; 514/252; 514/269; 514/270; 514/272; 514/273; 514/274; 514/275; 544/322; 544/300; 544/301; 544/310; 544/311; 544/316; 544/317; 544/319; 544/320; 544/321; 544/323; 544/324; 544/295; 544/122; 544/123; 544/82
[58] Field of Search .................. 514/232.2, 235.8, 252, 514/256, 269, 270, 272, 273, 274, 275; 544/322, 300, 301, 310, 311, 316, 317, 319, 320, 321, 323, 324, 295, 122, 123, 82

[56] References Cited

FOREIGN PATENT DOCUMENTS

| | | |
|---|---|---|
| 900178A | 7/1983 | European Pat. Off. . |
| 245687A | 4/1986 | European Pat. Off. . |
| 245687 | 11/1987 | European Pat. Off. . |
| 325397A | 1/1988 | European Pat. Off. . |
| 418071A | 9/1989 | European Pat. Off. . |
| 418071A2 | 9/1990 | European Pat. Off. . |
| 60-41655 | 3/1985 | Japan . |
| 62-258366 | 11/1987 | Japan . |
| 2-117651 | 5/1990 | Japan . |
| 3-120243 | 5/1991 | Japan . |

OTHER PUBLICATIONS

Bell et al., Chemical Abstracts, vol. 56, entry 12894f (1962).
Weinstock et al., Chemical Abstracts, vol. 73, entry 110105c (1970).
Bell et al. *J. Org. Chem.*, vol. 26, 1961, pp. 3534–3535.

Primary Examiner—John M. Ford
Attorney, Agent, or Firm—Birch, Stewart, Kolasch & Birch

[57] ABSTRACT

The present invention relates to novel 5-(ω-substituted amino-alkanoyl amino)pyrimidine derivatives, processes for producing the derivatives, and pharmaceutical compositions containing said derivatives. The compounds in the present invention have potent effects of inhibiting ACAT activity and lowering serum cholesterol. The compounds of the present invention are extremely useful for the treatment and/or prevention of arteriosclerosis or hyperlipidemia.

10 Claims, No Drawings

PYRIMIDINE DERIVATIVES

BACKGROUND OF THE PRESENT INVENTION

The present invention relates to novel substituted pyrimidine derivatives which have an amide bond in the 5-position, processes for producing the derivatives, and pharmaceutical compositions containing the pyrimidine derivatives for the treatment and/or prevention of arteriosclerosis or hyperlipidemia.

In recent years, arteriosclerosis has been recognized as a rapidly increasing disease in circulatory disorder, and is also given much attention as a basal lesion for serious disease. Arteriosclerosis causes various ischemic diseases or bleeding, for example, the ischemic heart disease due to coronary atherosclerosis, such as angina pectoris and myocardial infarction the cerebrovascular disease due to cerebrovascular arteriosclerosis, such as cerebral infarction and cerebral apoplexy, the optic nerve atrophy and hydrocephalia due to compression by cerebral arteriosclerosis, nephrosclerosis due to kidney arteriosclerosis, and aneurysm and arteriosclerosis obliterans due to stenosis in the lumen of the aorta and peripheral artery. Such diseases and occasionally fatal. It is generally said that hypertension, hyperlipidemia, smoking, obesity, diabetes and the like contribute to arteriosclerosis, especially pultaceous atherosclerosis. It is also known that cholesterinosis, calcinosis and foam cells derived from macrophages or vascular smooth muscle cells appear in sclerosis lesions. However, a clear mechanism for arteriosclerosis has not been elucidated, hence sufficient treatment and/or prevention of arteriosclerosis have yet to be established. In order to treat these diseases, drugs which can decrease serum cholesterol has been developed. Colestyramine and melinamide, which are inhibitors of cholesterol absorption from the intestine, and clofibrate, which partially facilitates cholesterol metabolism, are typical examples. As the mechanism of transport of serum cholesterol is gradually understood, drugs which regulate the balance of serum cholesterol level have also been developed. However, these drugs have not been effective in the prevention or treatment of arteriosclerosis. The development of drugs which lower the serum cholesterol level by the inhibition of cholesterol biosynthesis (HMG-CoA reductase inhibitors, squalene epoxidase inhibitors) has also been progressed. On the other hand, drugs that are antagonistic to platelet derived growth factor (PDGF) which inhibit the proliferation of vascular smooth muscle cells, and drugs which prevent macrophage infiltration to the arterial wall and the formation of foam cell, are also given much attention as a remedy for arteriosclerosis. Especially, in the stud of arteriosclerosis lesions, macrophage which transform into foam cell after scavenging degenerated lipids has been recognized as an essential factor which links hyperlipidemia to arteriosclerosis. It has also been said that the acyl-CoA cholesterol acyltransferase (ACAT) plays an important role on the onset of arteriosclerosis. That is to say, ACAT facilitates dietary cholesterol absorption from the intestine by esterification of free cholesterol at the intestinal mucosa. Furthermore, it is indicated that ACAT contributes to the formation of deposit of cholesterol esters derived from the above macrophage in the arterial wall. Therefore, ACAT inhibitors have been expected to lowering the level of serum lipids, and have been used for the treatment and/or prevention of arteriosclerosis.

Until now, various kinds of drugs for the treatment of arteriosclerosis have been developed, and some compounds directed to ACAT inhibition are described in JP-A-60 41655 and JP-A-2 117651. However, the development of these compounds has been discontinued since some of the compounds did not exhibit significant efficacy in clinical studies, and others had adverse effects on the liver, despite the good effects in lowering serum cholesterol in the animal models.

Although JP-A-62 258366 and JP-A-3 120243 exhibit pyrimidineamide compounds as anti-arteriosclerotic agents with an inhibitory effect on ACAT, the structures of these compounds are distinguishable from those of the present invention, and only a portion of inhibitory activities on ACAT in a variety of animal cells in vitro is shown. Further, there is no disclosure about any toxicological study in connection with the compounds described in JP-A-62 25866 and JP-A-3 120243.

Under these circumstances, anti-arteriosclerotic agents which possess beneficial effects directly on the arterial wall with good clinical efficacy and high safety in Homo sapiens are desired.

SUMMARY OF THE INVENTION

An object of the present invention is to provide novel 5-(ω-substituted amino-alkanoyl amino)-pyrimidine derivatives, or salts or solvates or solvates of said salts thereof.

Another object of the present invention is to provide a process for producing the novel pyrimidine derivatives.

A further object of the present invention is to provide pharmaceutical compositions for the treatment and/or the prevention of arteriosclerosis or hyperlipidemia which comprise the novel pyrimidine derivatives as active components.

Since the compounds of the present invention significantly prevent the accumulation of cholesteryl esters in macrophages and potently inhibit the microsomal ACAT activity from a variety of organs in vitro, these compounds are expected to exert beneficial effects directly on the atherosclerotic lesion. Further, the compounds of the present invention not only show significant hypolipidemic effect on high cholesterol diet feeding animals, but also have inhibitory activities on ACAT in microsomal fraction of human hepatoma cell line.

In addition, the compounds of the present invention have little toxicity and side effect on the liver and other organs that are apprehended with the former hypolipidemic drugs and/or ACAT inhibitor. It is therefore indicated that the compounds of the present invention are safe and beneficial for the treatment of arteriosclerosis itself and various maladies derived from arteriosclerosis, as such ischemic heart diseases caused by coronary atherosclerosis, such as angina pectoris and myocardial infarction, the cerebrovascular diseases caused by cerebrovascular arteriosclerosis, such as cerebral infarction and cerebral apoplexy, optic nerve atrophy and hydrocephalia caused by increased mechanical pressure in the region of cerebral arteriosclerosis, nephrosclerosis caused by arteriosclerosis of the kidney, aneurysm and arteriosclerosis obliterans caused by stenosis of the aorta and peripheral artery, sthenia of platelet aggregation, deep venous thrombosis, others; and hyperlipidemia, hypercholesterolemia, diabetes, variety of thrombosis, xanthoma and so on.

DETAILED DESCRIPTION OF THE INVENTION

As a result of extensive investigations, the present inventors have found novel pyrimidine derivatives and their salts which can directly affect the arterial wall, prevent the accumulation of cholesteryl esters in macrophages, and potently inhibit ACAT activity.

The present invention is directed to a pyrimidine derivatives represented by the formula (I):

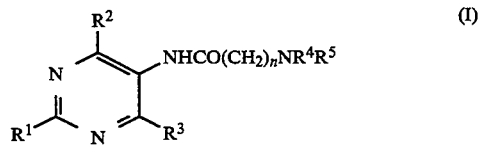

wherein $R^1$ represents a hydrogen atom, an alkyl group of straight or branched chain having 1 to 4 carbon atoms, $NR^6R^7$, $SR^8$ or $OR^8$, $R^2$ represents hydrogen atom, $NR^9R^{10}$, $SR^{11}$, $OR^{11}$, an alkyl group of straight or branched chain having 1 to 6 carbon atoms, or a halogen atom, $R^3$ represents a hydrogen atom, $NR^{12}R^{13}$, $SR^{14}$, $OR^{14}$, an alkyl group of straight or branched chain having 1 to 6 carbon atoms, or a halogen atom, $R^4$ and $R^5$ are identical or different and each represents a group selected from the group consisting of hydrogen atom, an alkyl group of straight or branched chain having 1 to 12 carbon atoms, a benzyl group, a cycloalkyl group having 3 to 10 carbon atoms and a phenyl group which may be substituted with 1 to 5 substituents selected that are optionally from the group consisting of an alkyl group of straight or branched chain having 1 to 6 carbon atoms, an alkoxyl group of straight or branched chain having 1 to 4 carbon atoms, a halogen atom, a hydroxyl group and an alkylenedioxy group having 1 or 2 carbon atoms, or $R^4$ and $R^5$, together with the nitrogen atom to which they are bonded, form a piperazine ring substituted with a phenyl group, or a tetrahydroquinoline ring, $R^6$, $R^7$ and $R^8$ are identical or different and each represents a group selected from the group consisting of hydrogen atom, and an alkyl group of straight or branched chain having 1 to 4 carbon atoms, $R^9$, $R^{10}$, $R^{11}$, $R^{12}$, $R^{13}$ and $R^{14}$ are identical or different and each represents a group selected from the group consisting of hydrogen atom, a phenyl group, a benzyl group, and an alkyl group of straight or branched chain having 1 to 10 carbon atoms, or $R^9$ and $R^{10}$, or $R^{12}$ and $R^{13}$, together with the nitrogen atom to which they are bonded, each form a morpholine ring, or a piperazine ring which may be substituted with an alkyl group of straight or branched chain having 1 to 4 carbon atoms, and n represents an integer from 1 to 6, provided that when n represents an integer of 1 and $R^2$ and $R^3$ represent methyl groups, $R^1$ does not represent a methyl group or an amino group, or a salt or a solvate or a solvate of said salt thereof, processes for producing said pyrimidine derivatives or a antiarteriosclerosis agent or antihyperlipidemia agent which comprises at least one of the said pyrimidine derivaties and pharmaceutically acceptable carriers. The substituted pyrimidine derivatives of the present invention and their salts potently inhibit the accumulation of cholesterol ester in macrophages and act on the arterial wall directly. Moreover, the substituted pyrimidine derivatives according to the present invention have the ability of the ACAT to inhibit ACAT. Therefore they can be used for the prevention, reduction or treatment of arteriosclerosis and hyperlipidemia.

In the compounds of the present invention represented by the formula (I), $R^1$ is preferably one of the above-mentioned groups; and hydrogen atom, methyl group, methoxy group, methylthio group or dimethylamino group are specially preferable. $R^2$ is preferably $NR^9R^{10}$ or an alkyl group of straight or branched chain having 1 to 6 carbon atoms; and $NR^9R^{10}$ or isopropyl group are specially preferable. $R^3$ is preferably $SR^{14}$, $OR^{14}$ or an alkyl group of straight or branched chain having 1 to 6 carbon atoms; and $SR^{14}$ or $OR^{14}$ are specially preferable. $R^4$ and $R^5$ are preferably an alkyl group of straight or branched chain having 1 to 12 carbon atoms, a benzyl group, a cycloalkyl group having 3 to 10 carbon atoms, and a phenyl group which may be substituted with 1 or 2 substituents that are selected from the group consisting of an alkyl group of straight or branched chain having 1 to 6 carbon atoms, an alkoxyl group of straight or branched chain having 1 to 4 carbon atoms, a halogen atom, hydroxyl group and an alkylenedioxy group having 1 or 2 carbon atoms. In the alternative, or $R^4$ and $R^5$, together with the nitrogen atom to which they are bonded, preferably form a piperazine ring substituted with a phenyl group, or a tetrahydroquinoline ring. $R^4$ is preferably an alkyl group of straight or branched chain having 3 to 10 carbon atoms or a cycloalkyl group having 3 to 10 carbon atoms. $R^5$ is preferably a phenyl group which may be substituted with 1 or 2 substituents that are selected from the group consisting of an alkyl group of straight or branched chain having 1 to 6 carbon atoms, an alkoxyl group of straight or branched chain having 1 to 4 carbon atoms, a halogen atom, a hydroxyl group and an alkylenedioxy group having 1 or 2 carbon atoms or a benzyl group. $R^9$ and $R^{10}$ are preferable alkyl groups of straight chain having 1 to 7 carbon atoms, phenyl groups or benzyl groups. In the alternative, $R^9$ and $R^{10}$, together with the nitrogen atom to which they are bonded, preferably form a morpholine ring. $R^{14}$ is preferably a hydrogen atom, an alkyl group of straight chain having 1 to 6 carbon atoms or a benzyl group. The letter n is preferably 2 to 5; and 3 or 4 are specially preferable.

From the view point of combination of these substituents preferable examples of the compounds of the present invention are, the compounds of the formula (I), wherein $R^1$ represents hydrogen atom or an alkyl group of straight or branched chain having 1 to 4 carbon atoms, $R^2$ represents $NR^9R^{10}$ or an alkyl group of straight or branched chain having 1 to 6 carbon atoms, $R^3$ represents $SR^{14}$, $OR^{14}$, or an alkyl group of straight or branched chain having 1 to 6 carbon atoms, $R^4$ and $R^5$ are identical or different and represent groups selected from the group consisting of an alkyl group of straight or branched chain having 1 to 12 carbon atoms, a cycloalkyl group having 3 to 10 carbon atoms, a benzyl group and a phenyl group which may be substituted with 1 or 2 substituents that are selected from the group consisting of an alkyl group of straight or branched chain having 1 to 6 carbon atoms, an alkoxyl group of straight or branched chain having 1 to 4 carbon atoms, halogen atom, hydroxyl group and an alkylenedioxy group having 1 to 2 carbon atoms; or $R^4$ and $R^5$, together with the nitrogen atom to which they are bonded, form a piperazine ring substituted with a phenyl group, or a tetrahydroquinoline ring. Other preferable examples are the compounds wherein $R^1$ represents $NR^6R^7$, $SR^8$ or $OR^8$, $R^2$ represents $NR^9R^{10}$ or an alkyl group of straight or branched chain having 1 to 6 carbon atoms, $R^3$ represents $SR^{14}$, $OR^{14}$ or an alkyl group of straight or branched chain having 1 to 6 carbon atoms, $R^4$ and $R^5$ are identical or different and represent groups selected from the group consisting of an alkyl group of straight or branched chain having 1 to 12 carbon atoms, a cycloalkyl group having 3 to 10 carbon atoms, a benzyl group and a phenyl group which may be substituted with 1 or 2 substituents that are selected from a group consisting of an alkyl group of straight or branched chain having 1 to 6 carbon atoms, an alkoxyl group of straight or branched chain having 1 to 4 carbon atoms, a halogen atom, hydroxyl group and an alkylenedioxy group having 1 or 2 carbon atoms; or $R^4$ and $R^5$, together with the nitrogen atom to which they are bonded, form a piperazine ring substituted with a phenyl group, or a tetrahydroquinoline ring.

More preferable compounds are the compounds of the formula (I), wherein $R^1$ represents hydrogen atom or an alkyl group of straight or branched chain having 1 to 4 carbon atoms, $R^2$ represents $NR^9R^{10}$ or an alkyl group of straight or branched chain having 1 to 6 carbon atoms, $R^3$ represents $SR^{14}$, $R^4$ represents an alkyl group of straight or branched chain having. 3 to 10 carbon atoms or a cycloalkyl group having 3 to 10 carbon atoms, $R^5$ represents a benzyl group, or a phenyl group which may be substituted with 1 or 2 substituents that are selected from the group consisting of an alkyl group of straight or branched chain having 1 to 6 carbon atoms, an alkoxyl group of straight or branched chain having 1 to 4 carbon atoms, a halogen atom, hydroxyl group and an alkylenedioxy group having 1 or 2 carbon atoms; $R^9$ and $R^{10}$ are identical or different and represent alkyl groups of straight chain having 1 to 7 carbon atoms, phenyl groups or benzyl groups, or $R^9$ and $R^{10}$, together with the nitrogen atom to which they are bonded, form a morpholine ring, $R^{14}$ represents hydrogen atom, an alkyl group of straight chain having 1 to 6 carbon atoms or a benzyl group and n represents an integer of 3 or 4. Further, more preferable examples are the compounds of the formula (I), wherein $R^1$ represents hydrogen atom, an alkyl group of straight or branched chain having 1 to 4 carbon atoms, $R^2$ represents $NR^9R^{10}$, $R^3$ represents $OR^{14}$, $R^4$ represents an alkyl group of straight or branched chain having 3 to 10 carbon atoms, $R^5$ represents a phenyl group which may be substituted with 1 or 2 substituents that are selected from a group consisting of an alkyl group of straight or branched chain having 1 to 6 carbon atoms, an alkoxyl group of straight or branched chain having 1 to 4 carbon atoms, a halogen atom, hydroxyl group and an alkylenedioxy group having 1 to 2 carbon atoms; $R^9$, $R^{10}$ and $R^{14}$ are identical or different and represent alkyl groups of straight or branched chain having 1 to 4 carbon atoms, and n represents an integer of 3 or 4. Further, other more preferable examples are the compounds of the formula (I), wherein $R^1$ represents $NR^6R^7$, $SR^8$ or $OR^8$, $R^2$ represents $NR^9R^{10}$, $R^3$ represents $SR^{14}$ or $OR^{14}$, $R^4$ represents an alkyl group of straight or branched chain having 3 to 10 carbon atoms, $R^5$ represents a phenyl group which may be substituted with 1 or 2 substituents that are selected from a group consisting of an alkyl group of straight or branched chain having 1 to 6 carbon atoms, an alkoxyl group of straight or branched chain having 1 to 4 carbon atoms, a halogen atom, a hydroxyl group and an alkylenedioxy group having 1 or 2 carbon atoms; $R^6$, $R^7$, $R^8$, $R^9$, $R^{10}$ and $R^{14}$ are identical or different and represent alkyl groups of straight or branched chain having 1 to 4 carbon atoms, and n represents an integer of 3 or 4.

The compounds of the present invention represented by the formula (I) can be obtained, for example, by the following Process 1, shown in <reaction scheme 1>. In the intermediates represented by the formula (II)–(VI) in reaction schemes 1–3, descriptions and other reaction schemes, substituents $R^1$–$R^5$ and n have the same significance as defined in the formula (I), X and Z each represent halogen atoms, R and R' each represent lower alkyl groups, and Ph represents a phenyl group.

Further in these intermediates, $R^1$–$R^3$ can also represent hydroxyl, mercapto or amino groups protected with a suitable conventional protecting group mentioned later.

<reaction scheme> process 1

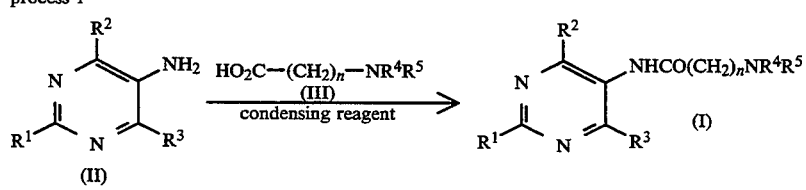

process 2

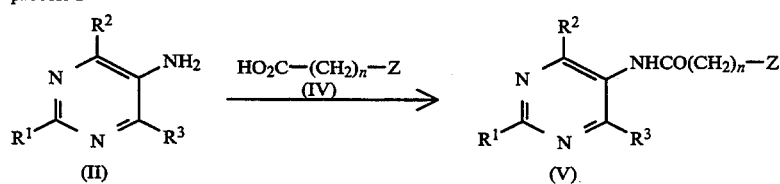

Process 1

Compounds of the formula (I) can be obtained by the reaction of intermediates of the formula (II) and intermediates of the formula (III) in the presence of condensing reagents in organic solvents. As a condensing reagent, dicyclohexylcarbodiimide (DCC), 2-halogeno-1-methylpyridinium iodide (Mukaiyama reagent), diethyl phosphorocyanidate (DEPC) or 1,1'-carbonyl diimidazole (CDI) can be use, preferably DCC or Mukaiyama reagent.

Moreover, instead of condensing reagents, the mixed anhydride method of using chloroformic ester and triethylamine, pyridine or N-methylmorpholine is useful for condensation.

When using DCC, DCC is added to a mixture of intermediates of the formula (II) and intermediates of the formula (III) at a temperature from approximately −20° C. to room temperature, preferably under ice-cooling, in a halogenated hydrocarbon type solvent, such as methylene chloride, chloroform and dichloroethane. The reaction mixture is warmed to room temperature, and stirred for from 1 hr to 24 hrs to obtain compounds of the formula (I).

Moreover, a Mukaiyama reagent is useful as a condensing reagent, as described in Chemistry Letters, p1163 (1975). After addition of Mukaiyama reagent according to the above DCC method, the reaction is carried out at a suitable temperature, from ice-cooling condition to gentle reflux condition.

Process 2

Intermediates of the formula (V) are obtained by the condensation of intermediates of the formula (II) and intermediates of the formula (IV) according to Process 1 or by the reaction of intermediates of the formula (II) with activated acid derivatives, prepared from intermediates of the formula (IV), such as acid halides or acid anhydrides.

The reaction using an acid halide is carried out in organic solvents at a suitable temperature below the boiling point of the mixture, in the presence of a suitable acid scavenger.

A tertiary amine such as triethylamine, pyridine, diisopropylethylamine or dimethylaminopyridine is employed as an acid scavenger, and an inert solvent such as a halogenated hydrocarbon, for example methylene chloride, an ether-type solvent, for example tetrahydrofuran or dioxane, or an aromatic hydrocarbon, for example toluene, is employed as a solvent wherein methylene chloride is preferred.

Intermediates of the formula (V) can be converted to compounds of the formula (I) by the reaction with amine derivatives of the formula (VI) in the presence of an organic base such as diethylaniline.

In the case of the formula (I) pyrimidine derivatives having mercapto groups, obtained above, the mercapto groups can be converted to substituted mercapto groups by the reaction with a suitable alkyl halide, aryl halide and/or aralkyl halide in the presence of an acid scavenger such as the above-mentioned tertiary amine.

Further, hydroxyl groups of pyrimidine derivatives can be converted to several substituent groups according to the preparation shown in the following Process (i).

Furthermore, the protecting groups of reactive functional groups such as hydroxyl, mercapto or amino group can be removed by the methods described in "Protective Groups in Organic Synthesis, second edition" T. W. Greene and P. G. M. Wuts ed., published by John Wiley and Sons, 1991. These reactive groups also can be subsequently converted to several functional groups by above-mentioned methods.

Intermediates of the formula (III) are known compounds, or can be synthesized from known or commercially available intermediates and can be synthesized from halogenocarboxylic acid derivatives, preferably halogenocarboxylic acid esters, or acrylic acid derivatives, with amine derivatives of the formula (VI).

In the case of the synthesis from halogenocarboxylic acid esters, the intermediates of the formula (III) can be obtained by the reaction of amine derivatives of the formulae (VI) with halogenocarboxylic acid esters with or without the inert solvents described in Process 2, using an organic base such as pyridine, triethylamine, dimethylaminopyridine, diethylaniline, dimethylaniline, diazabicycloundecene (DBU), etc., or an inorganic base such as potassium carbonate etc. and then by the hydrolysis with an alkali hydroxide such as sodium hydroxide.

In the case of the synthesis from acrylic acid, the intermediates of the formula (III) can be obtained by the reaction of acrylic acid and amine derivatives of the formula (VI) in an aqueous solution at a temperature from room temperature to the reflux temperature of the reaction mixture, preferably reflux condition.

Compounds of the formula (II) are also known compounds, or can be synthesized from known or commercially available intermediates. The synthetic methods about many pyrimidine intermediates are described in the review of "The Pyrimidines" D. J. Brown ed., published by John Wiley and Sons, 1962.

The detailed synthetic methods are described below.

Process (i)

4,6-Dihydroxypyrimidine derivatives, as starting materials, can De synthesized from amidine derivatives, such as formamidine or acetamidine, urea or its O-alkyl derivatives, thiourea or its S-alkyl derivatives and guanidine or its alkyl derivatives and malonic acid diesteEs by well-known method. The obtained 4,6-Dihydroxypyrimidine derivatives with reactive functional groups, such as hydroxyl, mercapto and amino, at the 2-position can be protected by a suitable protecting group, such as benzyl or acetyl, if necessary. Further, pyrimidine derivatives with protected reactive functional group at the 2-position can be synthesized directly using derivatives such as S-benzylisothiourea, O-benzylisourea, or 1-acetylguanidine.

The thus obtained 4,6-dihydroxypyrimidine derivatives are converted to the corresponding 4,6-dihydroxy-5-nitropyrimidine derivatives by the reaction with suitable nitrating reagents, such as concentrated nitric acid, fuming nitric acid, alkyl nitrate, nitric oxide, nitronium tetrafluoroborate and nitronium trifluoromethansulfonate, preferably with fuming nitric acid in acetic acid. Furthermore, 5-nitropyrimidine derivatives can be synthesized directly from 2-nitromalonic esters.

Hydroxyl groups at the 4- and 6-positions of the obtained 5-nitropyrimidine derivatives can be converted to 4,6-dichloro- or 4,6-dibromo-pyrimidine. As chlorinating or brominating reagents, oxalyl chloride, thionyl chloride, phosphorus trichloride, phosphorus pentachloride, phosphorus oxychloride, or corresponding bromide can be used.

Various kind of substituents can be introduced into the 4 and 6 positions of 4,6-disubstituted-5-nitropyrimidine derivatives by the reaction with nucleophilic reagents, as shown in <reaction scheme 2> below.

The same substituent groups are introduced at the 4- and 6-positions by using over two equivalents of nucleophilic reagents, and a different substituent group is introduced at the 4-position from that at the 6-position by using an equivalent of different nucleophilic reagents one by one. As nucleophilic reagents, substituted amine, alcohol, phenol, or mercapto etc. can be used. In <reaction scheme 2>, X represents a halogen atom, and $R^1$, $R^2$ and $R^3$ of each compounds have the same significance as defined in the formula (I).

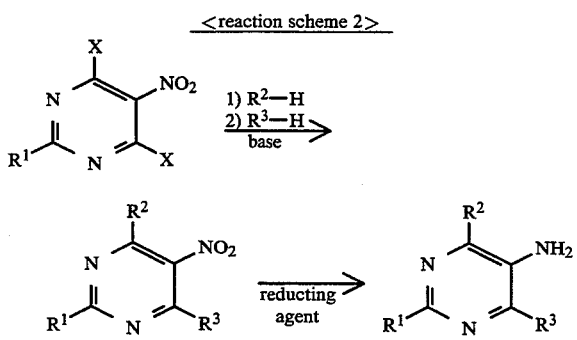

The introduction of amino groups can be carried out with desired mono- and/or di-substituted amines in the presence of the acid scavengers described above. The reactions are carried out conventionally in non-solvent or in suitable inert solvents such as the above-mentioned ether-type solvents or halogenated hydrocarbons, at a suitable temperature, preferably from −20° C. to room temperature, for 10 min. to 5 hrs.

The introduction of mercapto groups are carried out with sodium hydrosulfide in polar solvents, such as ethanol, methanol and dimethylformamide at a suitable temperature, preferably room temperature, for 1 hr to 10 hrs.

If necessary, the conversion from mercapto to alkylthio, arylthio or aralkylthio is carried out with alkyl halide, aryl halide or aralkyl halide using alkaline metal compounds, such as sodium hydride and alkoxide, or acid scavengers, such as the above-mentioned tertiary amines.

The substituted mercapto groups can directly be introduced by the reaction with sodium methylthiolate solution in an alcohol solvent, or with an alkyl mercaptane, an aryl mercaptane, an aralkyl mercaptane in an inert ether solvent such as cyclic- and dialkyl-ether, in the presence of as base, such as sodium hydride or alkoxide.

The synthesis of pyrimidine derivatives having an alkoxyl and/or phenoxy group can be carried out with an alkaline metal hydroxide in an alcohol, or a metal alkoxide or phenoxide, such as sodium alkoxide or phenoxide, in an alcoholic solvent.

Organometal reagents typically represented by Grignard reagents or lithium reagents, can be used as nucleophilic reagents to introduce alkyl and/or aryl groups. In the case of Grignard reagents, the reactions are carried out in above mentioned inert solvents or dimethylformamide, preferably in an ether-type solvent such as cyclic- or dialkyl-ether, without a catalyst or with metal catalysts such as 1,3-bis(diphenylphosphino)propane nickel cholride(Nidppp), 1,2-bis(diphenylphosphino)ethane nickel cholride(Nidppe), bis(-triphenylphosphine)palladium chloride, palladium acetate, preferably Nidppp or Nidppe, at a suitable temperature, generally at reflux condition with heat, for 1 hr to 24 hrs.

The corresponding 5-aminopyrimidine intermediates of the formula(II) can be prepared by the-reduction of the 5-nitropyrimidine derivatives obtained above, using zinc in acetic acid, or tin chloride, tin powder or iron powder in hydrochloric acid, or a reductant such as hydrogen gas with suitable catalysts, such as Raney nickel or palladium-carbon in an alcohol, preferably zinc in acetic acid. Namely, the 5-nitropyrimidine derivatives are dissolved with acetic acid, and zinc powder is added to the mixture under ice-cooling. The mixture is reacted at a temperature from −20° C. to the reflex temperature of the reaction mixture, preferably at room temperature, for 1 hr to 48 hrs, with stirring, to obtain the 5-aminopyrimidine intermediates of the formula Thus in the obtained intermediates of formula (II), the compounds having halogeno groups at the 4 and 6 positions, if necessary, can be reacted with the above-mentioned nucleophilic reagents. The compounds having a mercapto group of the pyrimidine derivatives can be converted to the compound having a substituted mercapto group.

If necessary, the protecting group of reactive functional group, such as hydroxyl, mercapto and amino can be removed by the method described "Protective Groups in Organic Synthesis", Second Edition, T. W. Greene and P. G. M. Wuts ed., published by John Wiley and Sons, at an arbitrary step in above process.

Process (ii)

According to the following <reaction scheme 3>, 5-phenylazopyrimidine can be synthesized by reacting phenylazo-β-keto esters prepared from β-keto esters, typically malonate or acetoacetate, and diazonium salts prepared from aniline and sodium nitrite, and amidine derivatives, such as formamidine and acetamidine, urea and its O-alkyl derivatives, thiourea and its S-alkyl derivatives, and guanidine and its alkyl derivatives in organic solvents, such as an alcohol in the presence of bases such as sodium alkoxide, at a suitable temperature from room temperature to the boiling temperature of the reaction mixture, for 1 hr to 10 hrs.

4,6-Dihydroxypyrimidine derivatives can be obtained using malonic acid diesters as starting materials.

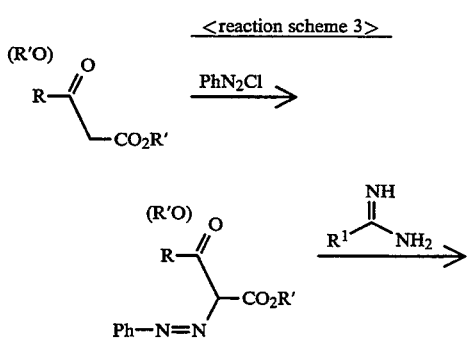

-continued
<reaction scheme 3>

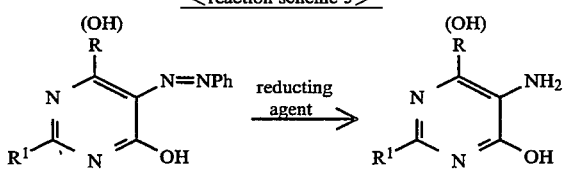

In the case of 4,6-dihydroxypyrimidine derivatives with reactive functional groups, such as hydroxyl, mercapto and amino at 2-position, the reactive functional groups can be protected by a suitable protecting group such as benzyl and acetyl etc., if necessary.

Further pyrimidine derivatives with protected reactive functional group at the 2-position, can be synthesized directly by using the derivatives of S-benzylisothiourea, O-benzylisourea, or 1-acetylguanidine.

5-Phenylazopyrimidine intermediates can be converted to 5-aminopyrimidine intermediates by electrolytic reduction in an acid solution, metal reduction using e.g. zinc, tin, nickel, or inorganic salts reduction using sodium hydrosulfite, preferably by the reduction using sodium hydrosulfite. The hydroxyl groups at 4(6)-position of 5-aminopyrimidine, obtained above, can be converted to several other substituent groups by the method shown in Process (i).

Process (iii)

The synthesis of pyrimidine having 6-alkyl, 6-aryl or 6-aralkyl group can be carried out directly by condensing β-diketones, typically acetoacetic acid ester, with amidine derivatives, such as formamidine or acetamidine, urea and its O-alkyl derivatives, thiourea and its S-alkyl derivatives, and guanidine and its alkyl derivatives. This method is well-known as Pinner's pyrimidine synthesis, wherein the reaction is carried out under basic conditions, for example, sodium alkoxide etc. in an alcohol, at a suitable temperature, preferably in a reflux condition, for 1 hr to 24 hrs.

β-diketone equivalents such as an acyl Meldrum's acid, diketene, diketene-acetone adduct(2,2,6-trimethyl-1,3-dioxin-4-one) can be used for pyrimidine synthesis under neutral conditions. In the case of pyrimidine derivatives with reactive functional groups, such as hydroxyl, mercapto, and amino at 2-position, the reactive functional groups can be protected by a suitable protecting group, such as benzyl or acetyl, if necessary. Further pyrimidine derivatives with a protected reactive functional group at 2-position, can be synthesized directly by using a derivative of S-benzylisothiourea, O-benzylisourea, or 1-acetylguanidine.

The obtained 2,6-disubstituted-4-pyrimidone derivatives Can be converted to substituted amino derivatives after halogenation according to the above-mentioned process. Then nitration and reduction at 5-position can convert the derivative to 5-aminopyrimidine intermediates of the formula (II).

Since the compounds of the present invention significantly prevent the ability of macrophages from accumulating cholesteryl esters, these compounds are expected to show an inhibitory effect against atherogenesis and/or the development of atherosclerotic lesion. Furthermore, the compounds potently inhibit the microsomal ACAT activity from a variety of organs in vitro. Indeed, these compounds are effective in reducing the intestinal absorption of dietary cholesterol and in inhibiting the synthesis and secretion of lipoproteins in the liver, resulting in hypolipidemic effect in experimental animals. Therefore, an obvious reduction of a risk factor for atherosclerosis can be expected. Not only do the pyrimidine derivatives and their salts of the present invention exert potent inhibition on the ACAT activity in microsomal fractions prepared from animal organs, but the derivatives also exert potent inhibition on the ACAT activity in those from human hepatoma cell line, HepG2, as compared with previous ACAT inhibitors. In addition, the compounds of the present invention possess quite low toxicity and side effect on the liver and other organs that are apprehended with the former hypolipidemic drugs and/or ACAT inhibitor.

Experimental Example will be illustrated by the pharmacological effects, toxicities, doses and directions for use of the compounds of the present invention.

Pharmacological effects of the compounds of the present invention are shown in more detail as follows.

Experimental Example 1

Inhibitory effect on cholesteryl ester accumulation in macrophages.

Mouse peritoneal macrophages were isolated from ddy-family male mice and cultured by the method of MS Brown et al. (MS Brown et al., J. Biol. Chem., 255, 9344 (1980)) with partial modification. Namely resident peritoneal cells suspended in phosphate-buffered saline (PBS) were plated in plastic Petri dishes (35 mm×10 mm) at a density of $2\times 10^6$ cells. The adherent macrophages were cultured overnight at 37° C. in Dalbecco's modified Eagle medium (DME) containing 10% fetal bovine serum (FCS) under humidified 5% $CO_2$. And then, the compounds of the present invention and the reference compound at the concentrations of 0.01~10 μM were applied to macrophages in DME containing 30 μg/ml rabbit β-very low density lipoproteins, 0.2 mM [$^3$H]oleic acid (185 kBq/ml) and 2.4 mg/ml bovine serum albumin, and incubated for additional 3 hrs. After discarding the medium, each macrophage monolayer was washed with PBS and lipids were extracted with hexane/isopropyl alcohol (3:2). Cholesteryl esters in the extract were separated by thin-layer chromatography and the radioactivity was measured by liquid scintillation counter. As the reference compound, CL277082 ((N'-2,4-difluorophenyl)-N-[[4-(2,2-dimethylpropyl)-phenyl]methyl]-N-heptyl urea; synthesized by the method of VG DeVries et al. ; VG DeVries et al. J. Med. Chem., 29, 1131 (1986)), which is a representative compound developed as an anti-atherosclerotic agent with selective inhibitory effect on ACAT, was used.

The inhibitory effect of the compounds of the present invention on cholesteryl ester accumulation in macrophages was shown in FIG. 1. The evaluation of the activity was defined in 3 grades as follows according to the concentration inducing 50% inhibition ($IC_{50}$).

TABLE 1

| A: 0.01 μM ≦ $IC_{50}$ < 0.1 μM |
|---|
| B: 0.1 μM ≦ $IC_{50}$ < 1.0 μM |
| C: 1.0 μM ≦ $IC_{50}$ < 10 μM |

| Example No. | Inhibition activity on cholesteryl ester accumulation |
|---|---|
| 143 | C |
| 148 | A |
| 219 | B |
| 220 | B |
| 221 | A |
| 223 | A |

TABLE 1-continued

A: 0.01 µM ≦ IC$_{50}$ < 0.1 µM
B: 0.1 µM ≦ IC$_{50}$ < 1.0 µM
C: 1.0 µM ≦ IC$_{50}$ < 10 µM

| Example No. | Inhibition activity on cholesteryl ester accumulation |
|---|---|
| 225 | A |
| 238 | B |
| 247 | A |
| 249 | B |
| CL277082 | C |

Each compound of the present invention exerted obvious inhibitory activity on the cholesteryl ester accumulation in macrophages.

Experimental Example 2

Hypocholesterolemic effect on cholesterol feeding rats. Male Wistar rats aged 7 weeks old were fed a diet (CE®) supplemented with 2%(w/w) cholesterol, 0.5%(w/w) sodium cholate, 10%(w/w) lard, 0.2%(w/w) propylthiouracyl and 5%(w/w) sucrose, for 3 days. Following 3 days, the compounds of the present invention were administered orally, and the animals were maintained with the high cholesterol diet. On the next day of final drug administration, blood was drown and serum total cholesterol-levels were measured enzymatically by autoanalyzer. CL277082 was used as a reference compound. The daily dose of the present compounds and % reduction of serum total cholesterol are shown in table 2.

TABLE 2

| Example No. | Dose (mg/kg/day) | % reduction of serum total cholesterol |
|---|---|---|
| 143 | 30 | 20 |
| 149 | 30 | 21 |
| 155 | 10 | 66 |
| 196 | 10 | 48 |
| 216 | 100 | 33 |
| 220 | 30 | 23 |
| 223 | 10 | 70 |
| 225 | 10 | 64 |
| 232 | 10 | 65 |
| 233 | 10 | 76 |
| 238 | 10 | 65 |
| 247 | 10 | 76 |
| 260 | 10 | 70 |
| 262 | 10 | 53 |
| CL277082 | 30 | 52 |

Each of the compounds of the present invention significantly improved hypercholesterolemia in the rats feeded with the high cholesterol diet.

Experimental Example 3

Inhibitory effect on microsomal ACAT activity in rabbit aorta.

Microsomal fraction of rabbit aorta was isolated by the method of Aram V Chobanian et al. (Aram V. Chobanian et al., Circulation Res., 56, 755 (1985)) with partial modifications. Namely, male New Zealand white rabbits aged 8 weeks old were fed on a diet supplemented with 1%(w/w) cholesterol for 2 months, and then the thoracic aorta was removed from the animals with serum total cholesterol levels from 2600 mg/dl to 4200 mg/dl. After removing the adventitia of the aorta, the intima and media were homogenized by teflon homogenizer in 40 mM 2-amino-2-hydroxymethyl-1,3-propanediol (Tris)-HCl (pH 7.2) containing 0.25M sucrose, 0.3 mM EDTA and 2 mM dithiothreitol. The obtained homogenate was centrifuged at 10,000×g for 15 minutes, and the supernatant was centrifuged twice at 100,000×g for 60 minutes. The resulting microsomal fraction was washed once and used for the experiment after resuspension in the same buffer.

The inhibitory effect of the compounds of the present invention on the microsomal ACAT activity were assayed by the method of AC Rustan et al. (AC Rustan et al., J. Biol. Chem., 263, 8126 (1988)) with partial modifications. In the incubation mixture of 0.1M potassium phosphate buffer (pH 7.4) containing 30 µM [$^{14}$C]oleyl-CoA (0.25 kBq/nmol) and 1 mg/ml bovine serum albumin, the enzymatic reaction was started by adding microsomes at the final concentration of 0.4 mg protein/ml. The incubation was carried out at 37° C. for 5 minutes, and stopped by the addition of acetone. After the extraction of lipids with hexane, cholesteryl esters were separated from other lipids by thin layer chromatography and the radioactivity was measured as described in experimental example 1. CL277082 was used as a reference compound.

Table 3 shows the concentration of the present compounds required to produce 50% inhibition of cholesterol esterification (IC$_{50}$).

TABLE 3

| (I) | | (II) | |
|---|---|---|---|
| Example No. | IC$_{50}$ (µM) | Example No. | IC$_{50}$ (µM) |
| 81 | 0.11 | 128 | 0.11 |
| 83 | 0.17 | 130 | 0.017 |
| 84 | 0.11 | 135 | 0.031 |
| 86 | 0.15 | 140 | 0.024 |
| 103 | 0.22 | 145 | 0.12 |
| 104 | 0.072 | 148 | 0.069 |
| 125 | 0.022 | 153 | 0.048 |
| 126 | 0.019 | CL277082 | 0.21 |

Each compound of the present invention showed remarkable inhibitory activity on ACAT in the rabbit aorta microsomes.

Experimental Example 4

Inhibitory effect on microsomal ACAT activity in rat liver.

Liver microsomes as an enzyme sample of ACAT were prepared from overnight-fasted male rats aged 6 weeks old according to the method of GN Anderson et al. (GN Anderson et al., Biochim. Biochem. Acta, 512, 539 (1978)) with partial modifications. ACAT activity was measured by the same procedure as described in Experimental Example 3. CL277082 was used as a reference compound.

Table 4 shows the concentration of the present compounds required to produce 50% inhibition of cholesterol esterification (IC$_{50}$).

TABLE 4

| (I) | | (II) | |
|---|---|---|---|
| Example No. | IC$_{50}$ (µM) | Example No. | IC$_{50}$ (µM) |
| 133 | 0.26 | 218 | 0.43 |
| 143 | 0.080 | 219 | 0.13 |
| 145 | 0.080 | 220 | 0.052 |
| 146 | 0.11 | 221 | 0.029 |
| 148 | 0.055 | 223 | 0.064 |
| 149 | 0.14 | 224 | 0.22 |
| 155 | 0.088 | 225 | 0.019 |
| 156 | 0.038 | 226 | 0.016 |
| 166 | 0.081 | 227 | 0.11 |
| 167 | 0.043 | 234 | 0.025 |

TABLE 4-continued

| | | | |
|---|---|---|---|
| 168 | 0.087 | 235 | 0.026 |
| 173 | 0.17 | 236 | 0.032 |
| 180 | 0.20 | 237 | 0.083 |
| 182 | 0.22 | 238 | 0.11 |
| 183 | 0.28 | 239 | 0.12 |
| 185 | 0.079 | 240 | 0.073 |
| 187 | 0.047 | 241 | 0.076 |
| 188 | 0.035 | 242 | 0.22 |
| 195 | 0.047 | 243 | 0.095 |
| 197 | 0.0088 | 244 | 0.19 |
| 205 | 0.28 | 245 | 0.064 |
| 210 | 0.47 | 246 | 0.014 |
| 216 | 0.12 | 247 | 0.016 |
| (III) | | (IV) | |
| 248 | 0.032 | 259 | 0.076 |
| 249 | 0.16 | 261 | 0.023 |
| 250 | 0.0096 | 263 | 0.10 |
| 252 | 0.033 | 266 | 0.17 |
| 256 | 0.10 | 268 | 0.056 |
| 257 | 0.22 | 272 | 0.037 |
| 258 | 0.23 | CL277082 | 0.62 |

Each compound of the present invention exhibited remarkable inhibitory activity on ACAT in the rat liver microsomes.

Experimental Example 5

Inhibitory effect on microsomal ACAT activity in human hepatoma cell line, HepG2.

The human hepatoma cell, HepG2, was cultured with DME containing 10% FCS. The cells were suspended in 40 mM Tris-HCl buffer (pH 7.4) containing 25 mM sucrose at a density of $4.5 \times 10^8$ cells and the membrane fraction of the cell was prepared by the method of Field F J et al. (Lipids, Vol. 26, 1, (1991)) with partial modifications. Namely, a homogenate of the fraction was prepared by a sonication. The homogenate was centrifuged at $10,000 \times g$ for 20 minutes and the supernatant was centrifuged at $100,000 \times g$ for 60 minutes. The resulting microsomal fraction was washed once by centrifuging at $100,000 \times g$ for 60 minutes and used for the experiment after resuspention in the same buffer.

The measurement of ACAT activity was performed by the same procedure as described in Experimental Example 3, wherein the enzyme sample was 0.8 mg/ml of the membrane fraction of HepG2, the reaction was carried out for 15 min. CL277082 was used as a reference compound.

Table 5 shows the concentration of the present compounds required to produce 50% inhibition of cholesterol esterification ($IC_{50}$).

TABLE 5

| Example No. | $IC_{50}$ (μM) |
|---|---|
| 81 | 0.21 |
| 120 | 1.0 |
| 121 | 0.85 |
| CL277082 | 1.4 |

Each compound of the present invention showed potent inhibitory activity on ACAT in HepG2 microsomes.

Experimental Examination 6

Acute toxicity.

The pyrimidine derivatives of the present invention were examined for acute toxicity by using male Wistar rats fasted over night aged 7 weeks old. After given orally the compounds of the Example 143 of the present invention at the single dose of 2 g/kg or the compounds of the Example 155, 196, 231, 232, 233, 240, 247, 260 and 262 of the present invention at the single dose of 1 g/kg, no lethal incident was observed over 7 days after the administration.

As mentioned above, it is clear that the compounds of the present invention possess a potent inhibitory effect on the accumulation of cholesteryl ester in macrophages in vitro and on ACAT in microsomal fractions of arterial wall and liver. These inhibitory activities on ACAT were more potent than a representative ACAT inhibitor, CL277082. Therefore, the compounds of the present invention are expected to exert beneficial effects directly on the atherosclerotic lesion. The compounds also show remarkable hypolipidemic effect on high cholesterol diet feeding rats and have inhibitory activity on ACAT in microsomal fraction of the human hepatoma cell line, HepG2. These compounds are accordingly expected to have a beneficial effect on the human hyperlipidemia and atherosclerosis. In addition, the compounds of the present invention have little toxicity and side effect on liver and other organs that are apprehended with the former hypolipidemic drugs and/or ACAT inhibitor. It is therefore indicated that the compounds of the present invention are safe and beneficial for the prevention and treatment of arteriosclerosis itself and various maladies derived from arteriosclerosis, such as (1) ischemic heart diseases caused by coronary atherosclerosis, such as angina pectoris and myocardial infarction etc., (2) the cerebrovascular diseases caused by cerebrovascular arteriosclerosis, such as cerebral infarction, cerebral apoplexy, cerebral thrombosis, transient ischemic attack and subarachnoid hemorrhage etc., (3) optic nerve atrophy and hydrocephalia caused by increased mechanical pressure in the region of cerebral arteriosclerosis, (4) nephrosclerosis caused by arteriosclerosis of the kidney, (5) aneurysm and arteriosclerosis obliterans caused by stenosis of the aorta and peripheral artery, (6) sthenia of platelet aggregation, (.7) deep venous thrombosis, and (8) others; hyperlipidemia, diabetes, variety of thrombosis, xanthoma and so on.

The compounds of the present invention may be in the form pharmaceutically acceptable salts. Typical examples of such salts of the-compounds include pharmaceutically acceptable salts with organic or inorganic acids, such as hydrochloric acid, hydrobromic acid, phosphoric acid, p-toluenesulfonic acid, methanesulfonic acid, salicylic acid, citric acid, fumaric acid, succinic acid, tartaric acid, oxalic acid, lactic acid and mandelic acid, or with acidic amino acids such as aspartic acid and glutamic acid.

The compounds of the present invention can be administered independently or can be mixed with appropriate pharmaceutically acceptable carriers or medium such as excipients, binders, lubricants, coloring agents, flavors, and optionally sterilized water, edible oils, non-toxic organic solvents or non-toxic solubilizers (for example, glycerin or propylene glycol), emulsifying agents, suspending agents (for example, Tween 80 or arabic gum), and can be prepared into the appropriate pharmaceutical compositions by appropriate selection and combination of the above compounds and carriers according to a conventional process.

The compounds of the present invention can be administered to the patient either orally or parenterally, in the form of tablets, capsules, powders, granules, subtilized granules, orally administrational liquid compositions, suppositories, syrups, inhalants, ointments or injections of aqueous or oily solutions, emulsions, suspensions or solidities or lyophilized formulations. The amount of the administration of the compounds may be in the range of 0.1 mg to 2.5 g/day, preferably 1 mg to 1.5 g/day. The amount of the administration may also be adjusted according to patients conditions or to the route of administration, and the total amount of the daily dose can be administered at once or at 2 to 6 times separately.

Hereafter the present invention will be described with references to the examples below but is not deemed to be limited thereto.

EXAMPLE 1

Preparation of 4,6-dihydroxy-2-methylpyrimidine

To a solution of sodium ethoxide, prepared from sodium (36.2 g) and ethanol (1000 ml), diethyl malonate (114 ml) and acetamidine hydrochloride (71 g) were added at room temperature, and the mixture was stirred for 5 hours under reflux. After cooling to room temperature, the resulting solid was collected by filtration and washed with ethanol and then dissolved in water. The aqueous solution was acidified to pH Ca.2 with concentrated hydrochloric acid (Ca. 170 ml) under ice-cooling. The formed precipitate was separated by filtration and washed with water, ethanol and ether to give 153 g (81%) of the objective compound.

Melting point: >300° C.
IR(KBr) $\nu$ cm$^{-1}$: 1687, 1641, 1577, 1456, 1329, 533, 525
NMR(90 MHz, DMSO-d$_6$) $\delta$ ppm: 4.95(1H, s), 2.21(3H, s)

The following compounds were prepared in a similar manner as EXAMPLE 1.

EXAMPLE 2

4,6-dihydroxy-2-(N,N-dimethylamino)pyrimidine
Yield: 68%
Melting point: 185.0° C. (decomposition)
IR(KBr) $\nu$ cm$^{-1}$: 1616, 1520, 1377, 1325, 789, 523
NMR(90 MHz, DMSO-d$_6$) $\delta$ ppm: 10.55(2H, br.s), 4.66(1H, s), 3.01(6H, s)

EXAMPLE 3

4,6-dihydroxy-2-methoxypyrimidine
Yield: 70%
IR(KBr) $\nu$ cm$^{-1}$: 1678, 1664, 1641, 1606, 1446, 1338, 1281
NMR(90 MHz, DMSO-d$_6$) $\delta$ ppm: 11.50(2H, br.s), 4.98(1H, s), 3.84(3H, s)

EXAMPLE 4

Preparation of 4,6-dihydroxy-2-methyl-5-nitropyrimidine

To a mixture of fuming nitric acid (160 ml) and acetic acid (260 ml) the product obtained in EXAMPLE 1 (100 g) was added portionwise, keeping inside at 10°-15° C. After stirring for 75 minutes at room temperature, the reaction mixture was poured into ice-water (1000 ml). The formed precipitate was separated by filtration and washed with water, ethanol and ether to give 107 g (79%) of the objective compound.

Melting point: >300° C.
IR(KBr) $\nu$ cm$^{-1}$: 2297, 1713, 1646, 1364, 1308
NMR(90 MHz, CDCl$_3$) $\delta$ ppm: 13.98(2H, br.s), 2.31(3H, s)

The following compounds were prepared in a similar manner as EXAMPLE 4.

EXAMPLE 5

4,6-dihydroxy-2-(N,N-dimethylamino)-5-nitropyrimidine
Yield: 82%
Melting point: 285.3° C. (decomposition)
IR(KBr) $\nu$ cm$^{-1}$: 97, 1647, 1406, 1387, 1321, 538
NMR(90 MHz, DMSO-d$_6$) $\delta$ ppm: 11.3(2H, br.s), 3.10(6H, s)

EXAMPLE 6

4,6-dihydroxy-2-methoxy-5-nitropyrimidine
Yield: 69%
Melting point: 168.8°-170.0° C.
IR(KBr) $\nu$ cm$^{-1}$: 64, 1630, 1595, 1560, 1435, 1315
NMR(90 MHz, DMSO-d$_6$) $\delta$ ppm: 6.12(2H, br.s), 3.95(3H, s)

EXAMPLE 7

4,6dihydroxy-2-methylthio-5-nitropyrimidine
Yield: 56.5%
Melting point: 214.3°-214.8° C.
IR(KBr) $\nu$ cm$^{-1}$: 1697, 1635, 1566, 1362, 1302, 1205, 530
NMR(90 MHz, DMSO-d$_6$) $\delta$ ppm: 7.50(2H, br.s), 2.56(3H, s)

EXAMPLE 8

Preparation of 4,6-dichloro-2-methyl-5-nitropyrimidine

To a suspension of the product obtained in EXAMPLE 4 (154 g) and phosphorus oxychloride (696 ml), diethylaniline (286 ml) was added dropwise under ice cooling. After refluxing for 3 hours, the reaction mixture was concentrated under reduced pressure. The residue was poured into ice-water (2000 ml) and extracted three times with ether. The organic layer was washed with water and saturated sodium chloride, dried over anhydrous sodium sulfate and concentrated under reduced pressure. The residue was purified by silica gel column chromatography (methylene chloride:hexane=1:1 to methylene chloride) to give 160.4 g (86%) of the objective compound.

Melting point: 42°-44° C.
IR(KBr) $\nu$ cm$^{-1}$: 1546, 1516, 1425, 1405, 1373, 1345, 834
NMR(90 MHz, CDCl$_3$) $\delta$ ppm: 2.73(3H, s)

The following compounds were prepared in a similar manner as EXAMPLE 8.

EXAMPLE 9

4,6-dichloro-2-(N,N-dimethylamino)-5-nitropyrimidine
Yield: 50%
Melting point: 123.1°-123.9° C.
IR(KBr) $\nu$ cm$^{-1}$: 1593, 1525, 1414, 1336, 1284, 829
NMR(90 MHz, CDCl$_3$) $\delta$ ppm: 3.25(6H, s)

EXAMPLE 10

4,6-dichloro-2-methoxy-5-nitropyrimidine
Yield: 18%
Melting point: 72.1°-73.8° C.
IR(KBr) $\nu$ cm$^{-1}$: 1566, 1543, 1525, 1479, 1389, 1358, 1300
NMR(90 MHz, CDCl$_3$) $\delta$ ppm: 4.12(3H, s)

EXAMPLE 11

4,6-dichloro-2-methylthio-5-nitropyrimidine
Yield: 95.3%
Melting point: 59.4°–60.0° C.
IR(KBr) $\nu$ cm$^{-1}$: 1537, 1500, 1292, 1238, 872, 845, 831
NMR(90 MHz, DMSO-d$_6$) $\delta$ ppm: 2.61(3H, s)

EXAMPLE 12

Preparation of 4-chloro-6-hydroxy-2-methyl-5-nitropyrimidine

To a suspension of the product obtained in EXAMPLE 4 (50 g) and phosphorus oxychloride (200 ml), diethylaniline (84 ml) was added dropwise under ice cooling. After stirring for 3 hours at 80° C., the reaction mixture was concentrated under reduced pressure. The residue was poured into ice-water (1000 ml) and extracted five times with ethyl acetate. The organic layer was washed with water and saturated sodium chloride, dried over anhydrous sodium sulfate and concentrated under reduced pressure. The residue was purified by silica gel column chromatography (methanol : methylene chloride=2:98–5:95) to give 6.4 g (11.5%) of the objective compound.

Melting point: 193.5°–196.5° C.
IR(KBr) $\nu$ cm$^{-1}$: 1687, 1584, 1542,. 1359, 1187
NMR(90 MHz, DMSO-d$_6$) $\delta$ ppm: 2.38(3H, s)

EXAMPLE 13

Preparation of 4-chloro-2-methyl-5-nitro-6-(N-phenyl-N-propylamino)pyrimidine

To a solution of the product obtained in EXAMPLE 8 (160 g) and triethylamine (128.6 ml) in THF (400 ml), a solution of N-propylaniline (109.5 ml) in THF (100 ml) was added dropwise. After stirring for 2 hours at room temperature, the formed insoluble material was removed by filtration and the filtrate was concentrated under reduced pressure. The residue was crystallized from ether and the crystal was separated by filtration and then washed with hexane/ether (9:1) to give 201 g (85%) of the objective compound.

Melting point: 99.8°–100.2° C.
IR(KBr) $\nu$ cm$^{-1}$: 1561, 1541, 1519, 1498, 1407, 1354, 1054
NMR (90 MHz, CDCl$_3$) $\delta$ ppm: 7.41–6.93(5H, m), 3.97(2H, t, J=7.6 Hz), 2.59(3H, s), 1.89–1.37(2H, m), 0.92(3H, t, J=7.0 Hz)

The following compounds were prepared in a similar manner as EXAMPLE 13.

EXAMPLE 14

4-chloro-6-(N,N-dimethylamino)-2-methyl-5-nitropyrimidine
Yield: 85%
Melting Point: 96.9°–98.4° C.
IR(KBr) $\nu$ cm$^{-1}$: 580, 1534, 1485, 1404, 1357, 1196, 835
NMR(90 MHz, CDCl$_3$) $\delta$ ppm: 3.12(6H, s), 2.51(3H, s)

EXAMPLE 15

4-chloro-6-(N,N-diethylamino)-2-methyl-5-nitropyrimidine
Yield: 84%
IR(neat) $\nu$ cm$^{-1}$: 2981, 2938, 1576, 1531, 1483, 1352, 834
NMR(90 MHz, CDCl$_3$) $\delta$ ppm: 3.46(4H, q, J=7.0 Hz), 2.50(3H, s), 1.21(6H, t, J=7.0 Hz)

EXAMPLE 16

4-chloro-6-(N,N-dipropylamino)-2-methyl-5-nitropyrimidine
Yield: 99%
IR(neat) $\nu$ cm$^{-1}$: 2968, 1574, 1533, 1481, 1352, 833
NMR(90 MHz, CDCl$_3$) $\delta$ ppm: 3.35 ( 4H, t, J=7.8 Hz), 2.50(3H, s), 1.86–1.32(4H, m), 0.89(6H, t, J=7.8 Hz)

EXAMPLE 17

4-chloro-6-(N,N-dibutylamino)-2-methyl-5-nitropyrimidine
Yield: 97%
IR(neat) $\nu$ cm$^{-1}$: 2962, 1571, 1533, 1478, 1353, 834
NMR(90 MHz, CDCl$_3$) $\delta$ ppm: 3.39(4H, t, J=7.4 Hz), 2.49(3H, s), 1.80–1.05(8H, m), 0.94(6H, t, J=5.9 Hz)

EXAMPLE 18

4-chloro-6-(N,N-dihexylamino)-2-methyl-5-nitropyrimidine
Yield: 100%
IR(neat) $\nu$ cm$^{-1}$: 2957, 2929, 1576, 1533, 1477, 1353, 834
NMR(90 MHz, CDCl$_3$) $\delta$ ppm: 3.38(4H, t, J=8.2 Hz), 2.49(3H, s), 1.74–1.62(16H, m), 0.89(6H, t, J=5.6 Hz)

EXAMPLE 19

4-(N-benzyl-N-ethylamino)-6-chloro-2-methyl-5-nitropyrimidine
Yield: 86%
IR(neat) $\nu$ cm$^{-1}$: 1570, 1531, 1481, 1412, 1350, 1043, 1043
NMR (90 MHz, CDCl$_3$ ) $\delta$ ppm: 7.44–7.11(5H, m), 4.81(2H, s), 3.36(2H, q, J=7.1 Hz), 2.51(3H, s), 1.16(3H, t, J=7.1 Hz)

EXAMPLE 20

4-(N-benzyl-N-heptylamino)-6-chloro-2-methyl-5-nitropyrimidine
Yield: 99%
IR(neat) $\nu$ cm$^{-1}$: 2929, 1569, 1533, 1351, 834
NMR(90 MHz, CDCl$_3$ ) $\delta$ ppm: 7.56–7.08(5H, m), 4.80(2H,s), 3.27(2H, t, J=7.6 Hz), 2.51(3H, s), 1.68–0.99(10H, m), 0.87(3H, t, J=5.6 Hz)

EXAMPLE 21

4-(N-butylamino)-6-chloro-2-methyl-5-nitropyrimidine
Yield: 100%
IR(neat) $\nu$ cm$^{-1}$: 2960, 2934, 1590, 1561, 1542, 1341
NMR(90 MHz, CDCl$_3$) $\delta$ ppm: 7.70(1H, br.s), 3.61(2H, q, J=6.3 Hz), 2.54(3H, s), 1.83–1.20(4H, m), 0.97(3H, t, J=6.9 Hz)

EXAMPLE 22

4-chloro-2-methyl-6-morpholino-5-nitropyrimidine
Yield: 63%
Melting point: 96.7°–98.1° C.
IR(KBr) $\nu$ cm$^{-1}$: 2855, 1571, 1522, 1451, 1346, 1114, 832
NMR(90 MHz, CDCl$_3$) $\delta$ ppm: 3.84–3.48(8H, m), 2.53(3H, s)

EXAMPLE 23

4-chloro-2-methyl-6-(4-methylpiperazinyl)-5-nitropyrimidine
Yield: 83%
Melting point: 80.4°–81.0° C.
IR(KBr) $\nu$ cm$^{-1}$: 2936, 1575, 1540, 1518, 1438, 1339, 989
NMR(90 MHz, CDCl$_3$) $\delta$ ppm: 3.61(4H, t, J=5.0Hz), 2.51(3H, s), 2.46(4H, t, J=4.6 Hz), 2.32(3H, s)

EXAMPLE 24

4-chloro-5-nitro-6-(N-phenyl-N-propylamino)-pyrimidine
Yield: 90%
Melting point: 136.8°–139° C.
IR(KBr) $\nu$ cm$^{-1}$: 1556, 1538, 1496, 1431, 1055
NMR(90 MHz, CDCl$_3$) $\delta$ ppm: 8.48(1H, s), 7.44–6.96(5H,m), 3.98(2H, t, J=7.8 Hz), 1.90–1.38(2H, m), 0.93(3H, t, J=7.3 Hz)

EXAMPLE 25

4-chloro-6-(N,N-dimethylamino)-5-nitropyrimidine
Yield: 57%
Melting point: 99.7°–102.0° C.
IR(KBr) $\nu$ cm$^{-1}$: 1590, 1526, 1481, 1425, 1003
NMR(90 MHz, CDCl$_3$) $\delta$ ppm: 8.36(1H, s), 3.15(6H, s)

EXAMPLE 26

4-chloro-6-(N,N-diethylamino)-5-nitropyrimidine
Yield: 82%
Melting point: 31.5°–31.7° C.
IR(KBr) $\nu$ cm$^{-1}$: 1578, 1524, 1483, 1354, 1022
NMR(90 MHz, CDCl$_3$) $\delta$ ppm: 8.34(1H, s), 3.48(4H, q, J=7.1 Hz), 1.30(6H, t, J=7.1 Hz)

EXAMPLE 27

4-chloro-6-(N,N-dibutylamino)-5-nitropyrimidine
Yield: 98%
IR(neat) $\nu$ cm$^{-1}$: 2962, 2873, 1572, 1533, 1485, 1352, 1030
NMR(90 MHz, CDCl$_3$) $\delta$ ppm: 8.33(1H, s), 3.40(4H, t, J=7.4 Hz), 1.80–1.05(8H, m), 0.9.4(6H, t, J=5.9 Hz)

EXAMPLE 28

4-chloro-6-(N,N-diethylamino)-2-methoxy-5-nitropyrimidine
Yield: 91%
IR(neat) $\nu$ cm$^{-1}$: 1576, 1525, 1500, 1462, 1385, 1344, 1254, 1030
NMR(90 MHz, CDCl$_3$) $\delta$ ppm: 3.96(3H, s), 3.46(4H, q, J=7.0 Hz), 1.24(6H, t, J=7.0 Hz)

EXAMPLE 29

4-chloro-6-(N,N-diethylamino)-2-methylthio-5-nitropyrimidine
Yield: 83%
Melting point: 69.5°–70.7° C.
IR(KBr) $\nu$ cm$^{-1}$: 1564, 1522, 1477, 1354, 1182
NMR(90 MHz, CDCl$_3$) $\delta$ ppm: 3.46(4H, q, J=7.1 Hz), 2.50(3H, s), 1.23(6H, t, J=7.1 Hz)

EXAMPLE 30

4-hydroxy-2-methyl-5-nitro-6-(N-phenyl-N-propylamino)pyrimidine
Yield: 90%
Melting point: 267.6°–268.6° C.
IR(KBr) $\nu$ cm$^{-1}$: 1639, 1616, 1552, 1532, 1494, 1482, 1421
NMR(90 MHz, CDCl$_3$) $\delta$ ppm: 12.96(1H, s), 7.56–7.02(5H, m), 4.01(2H, t, J=7.6 Hz), 2.41(3H, s), 1.83–1.35(2H, m), 0.89(3H, t, J=7.1 Hz)

EXAMPLE 31

Preparation of 4-chloro-6-(N,N-diphenylamino)-2-methyl-5-nitropyrimidine

A mixture of the product obtained in EXAMPLE (15 g), diphenylamine (12.2 g) and potassium carbonate (11.46 g) was stirred for 7 hours at 150° C. After cooling to room temperature, the reaction mixture was dissolved in hot ethyl acetate and the insoluble material was filtered off. The filtrate was concentrated under reduced pressure and the residue was purified by silica gel column chromatography (methylene chloride:hexane=1:1–3:1) followed by crystallization from, ether-hexane to give 4.9 g (20%) of the objective compound.
Melting point: 128.0°–129.9° C.
IR(KBr) $\nu$ cm$^{-1}$: 1548, 1541, 1508, 1490, 1436, 1397, 1347, 701
NMR (90 MHz, CDCl$_3$) $\delta$ ppm: 7.47–7.05(10H, m), 2.48(3H, s)

EXAMPLE 32

Preparation of 4,6-bis(N,N-diethylamino)-2-methyl-5-nitropyrimidine

To a solution of the product obtained in EXAMPLE 8 (5 g) and triethylamine (10 ml) in THF (50 ml), a solution of diethylamine (7.5 ml) in THF (20 ml) was added dropwise. After stirring for 6 hours at room temperature, diethylamine (5.0 ml) and triethylamine (8.4 ml) was added and the reaction mixture was stirred for another 17 hours at room temperature. The formed insoluble material was filtered off and the filtrate was concentrated under reduced pressure. The residue was dissolved in ether and washed with water and saturated sodium chloride. After drying over anhydrous sodium sulfate, the solvent was evaporated under reduced pressure to give 6.7 g (99%) of the objective compound.
IR(neat) $\nu$ cm$^{-1}$: 2979, 1549, 1507, 1498, 1492, 1459, 1250, 1100
NMR(90 MHz, CDCl$_3$) $\delta$ ppm: 3.63(8H, q, J=7.0 Hz), 2.29(3H, s), 1.26(12H, t, J=7.0 Hz)

The following compound was prepared in a similar manner as EXAMPLE 32.

EXAMPLE 33

4,6-bis(hexylamino)-2-methyl-5-nitropyrimidine
Yield: 94%
Melting point: 48.2°–48.7° C.
IR(KBr) $\nu$ cm$^{-1}$: 3338, 2929, 2855, 1571, 1536, 1263, 1172
NMR(90 MHz, CDCl$_3$) $\delta$ ppm: 9.33(2H, br.s), 3.59(4H, dt, J=5.6 and 6.6 Hz), 2.35(3H, s), 1.83–1.08(16H,m), 0.89(6H, t, J=5.6 Hz)

EXAMPLE 34

Preparation of 4-mercapto-2-methyl-5-nitro-6-(N-phenyl-N-propylamino)pyrimidine

To a suspension of sodium hydrosulfide n-hydrate (65.3 g) in ethanol (300 ml), a solution of the product obtained in EXAMPLE 13 (100 g) in ethanol (200 ml) was added. After refluxing for 40 minutes, the solvent was evaporated under reduced pressure and the residue was dissolved in water (1500 ml). The aqueous solution was acidified to pH 4 with 3N hydrochloric acid and extracted with ethyl acetate. The organic layer was washed with water and saturated sodium chloride and dried over anhydrous sodium sulfate. The solvent was evaporated under reduced pressure to give 96.9 g (97%) of the objective compound.

IR(neat) $\nu$ cm$^{-1}$: 1605, 1564, 1556, 1539, 1509, 1423, 1335

NMR(90 MHz, CDCl$_3$) $\delta$ ppm: 12.56(1H, s), 7.39–6.99(5H, m), 3.96(2H, t, J=7.6 Hz), 2.47(3H, s), 1.87–1.36(2H, m), 0.89(3H, t, J=7.6 Hz)

The following compounds were prepared in a similar manner as EXAMPLE 34.

EXAMPLE 35

4-(N,N-dimethylamino)-6mercapto-2-methyl-5-nitropyrimidine

Yield: 99%

Melting point: 192.5° (decomposition)

IR(KBr) $\nu$ cm$^{-1}$: 1579, 1516, 1417, 1401, 1350

NMR(90 MHz, CDCl$_3$) $\delta$ ppm: 3.16(6H, s), 2.42(3H, s)

EXAMPLE 36

4-(N,N-diethylamino)-6-mercapto-2-methyl-5-nitropyrimidine

Yield: 85%

Melting point: 185.6°–186.3° C.

IR(KBr) $\nu$ cm$^{-1}$: 1617, 1576, 1523, 1482

NMR(90 MHz, CDCl$_3$) $\delta$ ppm: 12.47(1H, s), 3.49(4H, q, J=7.1 Hz), 2.42(3H, s), 1.22(6H, t, J=7.1 Hz)

EXAMPLE 37

4-(N,N-dipropylamino)-6-mercapto-2-methyl-5-nitropyrimidine

Yield: 80.4%

Melting point: 165.5°–167.0° C.

IR(KBr) $\nu$ cm$^{-1}$: 2972, 1614, 1570, 1525, 1477, 1333

NMR(90 MHz, CDCl$_3$) $\delta$ ppm: 12.53(1H, s), 3.39(4H, t, J=7.6 Hz), 2.41(3H, s), 1.84–1.38(4H, m), 0.89(6H, t, J=7.3 Hz)

EXAMPLE 38

4-(N,N-dibutylamino)-6-mercapto-2-methyl-5-nitropyrimidine

Yield: 97%

Melting point: 139.5°–141.0° C.

IR(KBr) $\nu$ cm$^{-1}$: 2960, 2932, 1619, 1560, 1527

NMR(90 MHz, CDCl$_3$) $\delta$ ppm: 12.09(1H, s), 3.42(4H, t, J=7.4 Hz), 2.40(3H, s), 1.80–1.05(8H, m), 0.92(6H, t, J=6.3 Hz)

EXAMPLE 39

4-(N,N-dihexylamino)-6-mercapto-2-methyl-5-nitropyrimidine

Yield: 96%

Melting point: 81.8°–83.6° C.

IR(KBr) $\nu$ cm$^{-1}$: 2956, 2928, 2857, 1611, 1568, 1531

NMR(90 MHz, CDCl$_3$) $\delta$ ppm: 12.37(1H, s), 3.42(4H, t, J=7.3 Hz), 2.40(3H, s), 1.80–1.08(16H, m), 0.88(6H, t, J=5.8 Hz)

EXAMPLE 40

4-(N,N-diphenylamino)-6-mercapto-2-methyl-5-nitropyrimidine

Yield: 90%

Melting point: 205.5°–207.9° C.

IR(KBr) $\nu$ cm$^{-1}$: 1604, 1552, 1532, 1488, 1465, 1423, 1195

NMR(90 MHz, DMSO-d$_6$) $\delta$ ppm: 13.74(1H, s), 7.46–7.06(10H, m), 2.23(3H, s)

EXAMPLE 41

4-(N-benzyl-N-ethylamino)-6-mercapto-2-methyl-5-nitropyrimidine

Yield: 93%

Melting point: 136.7°–137.6° C.

IR(KBr) $\nu$ cm$^{-1}$: 1605, 1558, 1525, 1477, 1452, 1329

NMR(90 MHz, CDCl$_3$) $\delta$ ppm: 12.40(1H, br.s), 7.56–7.08(5H, m), 4.82(2H, 3.37(2H, q, J=7.1 Hz), 2.40(3H, s), 1.16(3H, t, J=7.1 Hz)

EXAMPLE 42

4-(N-benzyl-N-heptylamino)-6-mercapto-2-methyl-5-nitropyrimidine

Yield: 87%

Melting point: 116.2°–117.5° C.

IR(KBr) $\nu$ cm$^{-1}$: 2968, 2928, 1635, 1570, 1499

NMR(90 MHz, CDCl$_3$) $\delta$ ppm: 12.27(1H, s), 7.44–6.96(5H, m), 4.80(2H, s), 3.29(2H, t, J=7.8 Hz), 2.41(3H, s), 1.74–1.02(10H, m), 0.86(3H, t, J=5.8 Hz)

EXAMPLE 43

4-(N-butylamino)-6-mercapto-2-methyl-5-nitropyrimidine

Yield: 60%

Melting point: 209.8°–212.4° C.

IR(KBr) $\nu$ cm$^{-1}$: 3315, 2958, 1598, 1546, 1542, 1140

NMR(90 MHz, DMSO-d$_6$) $\delta$ ppm: 13.07(1H, br.s), 8.39(1H, t, J=5.3 Hz), 3.43(2H, q, J=6.3 Hz), 2.31(3H, s), 1.68–1.02(4H, m), 0.95(3H, t, J=6.6 Hz)

EXAMPLE 44

4-mercapto-2-methyl-6-morpholino-5-nitropyrimidine

Yield: 97%

Melting point: 213.2°–216.9° C.

IR(KBr) $\nu$ cm$^{-1}$: 3190, 1607, 1571, 1517, 1423, 1320

NMR(90 MHz, DMSO-d$_6$) $\delta$ ppm: 13.31(1H, br.s), 3.72–3.36(8H, m), 2.32(3H, s)

EXAMPLE 45

4-mercapto-2-methyl-6-(4-methylpiperazinyl)-5-nitropyrimidine

Yield: 100%

Melting point: 234.2°–243.2° C.

IR(KBr) $\nu$ cm$^{-1}$: 3384, 1615, 1595, 1561, 1522, 978

NMR(90 MHz, DMSO-d$_6$) $\delta$ ppm: 3.51–3.06(8H, m), 2.75(3H, s), 2.36(3H, s)

EXAMPLE 46

4-mercapto-5-nitro-6-(N-phenyl-N-propylamino)-pyrimidine

Yield: 92%

Melting point: 136.7°–139.2° C.

IR(KBr) $\nu$ cm$^{-1}$: 1610, 1555, 1530, 1509

NMR(90 MHz, CDCl$_3$) $\delta$ ppm: 7.88(1H, s), 7.44–7.00(5H, m), 3.96(2H, t, J=7.6 Hz), 1.80–1.32(2H, m), 0.90(3H, t, J=7.3 Hz)

EXAMPLE 47

4-(N,N-diethylamino)-6-mercapto-5-nitropyrimidine

Yield: 88%

Melting point: 146.1°–148.2° C.

IR(KBr) $\nu$ cm$^{-1}$: 1618, 1566, 1520, 1423, 1335, 1032

NMR(90 MHz, DMSO-d$_6$) δ ppm: 13.45(1H, br.s), 8.08(1H, s), 3.43(4H, q, J=6.9 Hz), 1.13(6H, t, J=6.9 Hz)

EXAMPLE 48

4-(N,N-dibutylamino)-6-mercapto-5-nitropyrimidine
Yield: 86%
Melting point: 97.3°–99.4° C.
IR(KBr) ν cm$^{-1}$: 2958, 1616, 1562, 1533, 1479, 1335, 1038
NMR(90 MHz, CDCl$_3$) δ ppm: 12.61(1H, br.s), 7.80(1H, s), 3.43(4H, t, J=7.4 Hz), 1.83–1.08(8H, m), 0.92(6H, t, J=6.3 Hz)

EXAMPLE 49

4-(N,N-diethylamino)-6-mercapto-2-methoxy-5-nitropyrimidine
Yield: 93%
Melting point: 145.5°–145.8° C.
IR(KBr) ν cm$^{-1}$: 1612, 1566, 1524, 1342, 1327, 1032
NMR(90 MHz, DMSO-d$_6$) δ ppm: 13.20(1H, br.s), 3.93(3H, s), 3.42(4H, q, j=7.0 Hz), 1.15(6H, t, J=7.0 Hz)

EXAMPLE 50

4-(N,N-diethylamino)-6-mercapto-2-methylthio-5-nitropyrimidine
Yield: 95%
Melting point: 143.9°–144.3° C.
IR(KBr) ν cm$^{-1}$: 1566, 1527, 1438, 1412, 1333, 1230
NMR(90 MHz, DMSO-d$_6$) δ ppm: 13.61(1H, s), 3.44(4H, q, J=7.0 Hz), 2.51(3H, s), 1.15(6H, t, J=7.0 Hz)

EXAMPLE 51

Preparation of 4,6-dimercapto-2-methyl-5-nitropyrimidine
Starting from the product obtained in EXAMPLE 8, the objective compound was prepared in a similar manner as EXAMPLE 34.
Yield: 99%
Melting point: >300° C.
IR(KBr) ν cm$^{-1}$: 1624, 1618, 1601, 1579, 1542, 1535, 1353, 1158
NMR(90 MHz, DMSO-d$_6$) δ ppm: 2.39(3H, s)

EXAMPLE 52

Preparation of 4-(N,N-diethylamino)-2-(N,N-dimethylamino)-6-mercapto-5-nitropyrimidine
Starting from 4-chloro-6-(N,N-diethylamino)-2-(N,N-dimethylamino)-5-nitropyrimidine (prepared in a similar manner as EXAMPLE 13 by using the product obtained in EXAMPLE 9 as a starting substrate), the objective compound was prepared in a similar manner as EXAMPLE 34.
Yield: 52%
Melting point: 152.3° C. (decomposition)
IR(KBr) ν cm$^{-1}$: 2933, 16.08, 1562, 1514, 1444, 1327
NMR (90 MHz, CDCl$_3$) δ ppm: 3.42(4H, q, J=6.9 Hz), 3.17(6H, s), 1.22(6H, t, J=6.9 Hz)
The following compound was prepared in a similar manner as EXAMPLE 52

EXAMPLE 53

4-(N,N-dibutylamino)-2-(N,N-dimethylamino)-6-mercapto-5-nitropyrimidine
Yield: 43%
Melting point: 153.0°–153.6° C.
IR(KBr) ν cm$^{-1}$: 2960, 1614, 1556, 1512, 1454
NMR(90 MHz, DMSO-d$_6$) δ ppm: 11.2(1H, S), 3.48–3.12(4H, m), 3.10(6H, s), 1.74 –0.84(8H, m), 0.87(6H, t, J=5.9 Hz)

EXAMPLE 54

Preparation of 2-methyl-4-methylthio-5-nitro-6-(N-phenyl-N-propylamino)pyrimidine
To a solution of the product obtained in EXAMPLE 13 (1.0 g) in methanol (100 ml), 15% aqueous sodium methanethiolate (15 ml) was added. After stirring for 1 hour at room temperature, the solvent was evaporated under reduced pressure and the residue was dissolved in ethyl acetate. The solution was washed with water and saturated sodium chloride, dried over anhydrous sodium sulfate and then concentrated under reduced pressure to give 0.98 g (95%) of the objective compound.
Melting point: 116.9°–118.9° C.
IR(KBr) ν cm$^{-1}$: 1542, 1510, 1491, 1424, 1340, 1214, 1061, 836, 700
NMR(90 MHz, CDCl$_3$) δ ppm: 7.46–6.94(5H, m), 4.04(2H, t, J=7.4 Hz), 2.57(3H, s), 2.49(3H, s), 1.67–1.44(2H, m), 0.92(3H, t, J=7.3 Hz)

EXAMPLE 55

Preparation of 4,6-dimethoxy-2-methyl-5-nitropyrimidine
To a solution of potassium hydroxide (9.5 g) in ethanol (95 ml), the product obtained in EXAMPLE 8 (10 g) was added under ice-cooling and the mixture was stirred for 15 minutes. The solvent was evaporated under reduced pressure and the residue was dissolved in water. The aqueous solution was neutralized with 2N hydrochloric acid and extracted with ethyl acetate. The organic layers were collected to wash with water and saturated sodium chloride. After drying over anhydrous sodium sulfate, the solvent was evaporated under reduced pressure and the residue was crystallized from ether to give 7.5 g (78%) of the objective compound.
Melting point: 113.5°–115.2° C.
IR(KBr) ν cm$^{-1}$: 1578, 1568, 1530, 1392, 1375, 1341, 1252, 1141
NMR(90 MHz, CDCl$_3$) δ ppm: 4.05(6H, s), 2.55(3H, s)
The following compounds were prepared in a similar manner as EXAMPLE 55.

EXAMPLE 56

4-methoxy-2-methyl-5-nitro-6-(N-phenyl-N-propylamino)pyrimidine
Yield: 93%
Melting point: 133.3°–135.0° C.
IR (KBr) ν cm$^{-1}$: 1574, 1543, 1496, 1377, 1336, 1192
NMR(90 MHz, CDCl$_3$) δ ppm: 7.46–6.99(5H, m), 3.97(2H, t, J=7.6 Hz), 3.95(3H, s), 2.51(3H, s), 1.89–1.39(2H, m), 0.91(3H, t, J=7.3 Hz)

EXAMPLE 57

4-(N,N-diethylamino)-6-methoxy-2-methyl-5-nitropyrimidine
Yield: 100%
IR(neat) ν cm$^{-1}$: 2975, 2934, 1583, 1552, 1523
NMR(90 MHz, CDCl$_3$) δ ppm: 3.96(3H, s), 3.43(4H, q, J=6.9 Hz), 2.42(3H, s), 1.18(6H, t, J=6.9 Hz)

EXAMPLE 58

4-(N,N-dipropylamino)-6-methoxy-2-methyl-5-nitropyrimidine

Yield: 97%

IR(neat) ν cm⁻¹: 1585, 1551, 1524, 1377, 1119

NMR(90 MHz, CDCl₃) δ ppm: 3.96(3H, s), 3.33(4H,t, J=7.4 Hz), 2.41(3H, s), 1.83–1.38(4H, m), 0.87(6H, t, J=7.3 Hz)

EXAMPLE 59

4-(N,N-dibutylamino)-6-methoxy-2-methyl-5-nitropyrimidine

Yield: 98%

IR(neat) ν cm⁻¹: 3410, 2960, 1597, 1375, 1120, 839, 787

NMR(90 MHz, CDCl₃) δ ppm: 3.96(3H, s), 3.37(4H,t, J=7.3 Hz), 2.41(3H, s), 1.74–1.02(8H, m), 0.92(6H, t, J=6.3 Hz)

EXAMPLE 60

4-(N,N-dibutylamino)-6-ethoxy-2-methyl-5-nitropyrimidine

Yield: 96%

IR(neat) ν cm⁻¹: 2960, 2873, 1581, 1549, 1524, 1379, 1344, 1120

NMR(90 MHz, CDCl₃) δ ppm: 4.42(2H, q, J=7.1 Hz), 3.37(4H, t, J=7.3 Hz), 2.40(3H, s), 1.34(3H, t, J=7.1 Hz), 1.75–0.96(8H, m), 0.92(6H, t, J=6.3 Hz)

EXAMPLE 61

4-(N,N-dibutylamino)-6-ethoxy-5-nitropyrimidine

Yield: 87%

IR(neat) ν cm⁻¹: 2960, 1587, 1537, 1506, 1470, 1444, 1101

NMR(270 MHz, CDCl₃) δ ppm: 8.19(1H}s), 4.44(2H, q, J=7.1 Hz), 3.37(4H, t, J=7.8 Hz), 1.62–1.49(4H, m), 1.37(3H, t, J=7.1 Hz), 1.38–1.20(4H, m), 0.92(6H, t, J=7.3 Hz)

EXAMPLE 62

4-(N,N-diethylamino)-6-methoxy-2-methylthio-5-nitropyrimidine

Yield: 98%

IR(neat) ν cm⁻¹: 1572, 1518, 1435, 1379, 1327, 1304, 1254, 1109

NMR(90 MHz, CDCl₃) δ ppm: 3.97(3H, S), 3.43(4H, q, J=7.1 Hz), 2.49(3H, S), 1.20(6H, t, J=7.1 Hz)

EXAMPLE 63

4-(N,N-diethylamino)-2,6-dimethoxy-5-nitropyrimidine

Yield: 84%

IR(neat) ν cm⁻¹: 1591, 1560, 1524, 1456, 1385, 1352, 1209, 1109

NMR(90 MHz, CDCl₃) δ ppm: 3.99(3H, s), 3.94(3H, s), 3.43(4H, q, J=7.1 Hz), 1.22(6H, t, J=7.1 Hz)

EXAMPLE 64

Preparation of 2-methyl-4-methylthio-5-nitro-6-(N-phenyl-N-propylamino)pyromidine Methyl iodide (4.6 ml) was added slowly to a solution of the product obtained in EXAMPLE 34 (15 g) and triethylamine (8.1 ml) in methylene chloride (200 ml) and the mixture was stirred for 1 hour at room temperature. The solution was washed with water and saturated sodium chloride. After drying over anhydrous sodium sulfate, the solvent was evaporated under reduced pressure and the residual crystal was washed with ether to give 13.5 g (86%) of the objective compound.

Melting point: 116.9°–118.9° C.

IR(KBr) ν cm⁻¹: 1542, 1510, 1491, 1424, 1340, 1214, 1061, 836, 700

NMR(90 MHz, CDCl₃) δ ppm: 7.46–6.94(5H, m), 4.04(2H, t, J=7.4 Hz), 2.57(3H, s), 2.49(3H, s), 1.67–1.44(2H, m), 0.92(3H, t, J=7.3 Hz)

The following compounds were prepared in a similar manner as EXAMPLE 64.

EXAMPLE 65

2-methyl-4,6-bis(methylthio)-5-nitropyrimidine

Yield: 73%

Melting point: 181.8°–184.7° C.

IR (KBr) ν cm⁻¹: 1525, 1519, 1507, 1329, 1311, 1202, 826

NMR (90 MHz, CDCl₃) δ ppm: 2.68(3H, s), 2.55(6H, s)

EXAMPLE 66

4,6-bis(hexylthio)-2-methyl-5-nitropyrimidine

Yield: 19%

Melting point: 28.4°–31.5° C.

IR(KBr) ν cm⁻¹: 2930, 1534, 1498, 1322, 823

NMR(90 MHz, CDCl₃) δ ppm: 3.17(4H, t, J=7.1 Hz), 2.64(3H, s), 1.98–1.08(16H, m), 0.90(6H, t, J=5.8 Hz)

EXAMPLE 67

Preparation of 4-mercapto-2-methyl-5-nitro-6-propylthiopyrimidine

To a solution of the product obtained in EXAMPLE 51 (4.87 g) in DMF (100 ml), sodium hydride (60% NaOH dispersion in mineral oil; 1.13 g) was added under ice-cooling and under nitrogen atmosphere. After stirring for 20 minutes, a solution of n-propyl bromide (2.35 ml) in DMF (10 ml) was added dropwise to the mixture and the resulting mixture was stirred for 1 hour under ice-cooling and for 1.5 hour at room temperature.

The reaction mixture was diluted with water, acidified to pH 3 with concentrated hydrochloric acid and then extracted three times with ethyl acetate. The collected organic layer was washed with water and saturated sodium chloride and dried over anhydrous sodium sulfate. The solvent was evaporated under reduced pressure and the residue was purified by silica gel column chromatography (ethyl acetate:hexane=1:2–1:1) to give 1.31 g (23%) of the objective compound.

Melting point: 161.5°–163.7° C.

IR(KBr) ν cm⁻¹: 2965, 1560, 1534, 1527, 1420, 1357, 858

NMR(90 MHz, CDCl₃) δ ppm: 3.19(2H, t, J=7.3 Hz), 2.55(3H, s), 1.73(2H, q, J=7.3 Hz), 1.03(3H, t, J=7.3 Hz)

EXAMPLE 68

Preparation of 5-amino-2-methyl-4-mercapto-6-(N-phenyl-N-propylamino)pyrimidine

To a solution of the product obtained in EXAMPLE 34 (96.6 g) in acetic acid (1000 ml), zinc powder (103.7 g) was added portionwise under ice-cooling. After stirring for 17 hours at room temperature, the insoluble materials were filtered off and washed with ethyl acetate. The filtrate was concentrated under reduced pressure and the residue Was dissolved in ethyl acetate. The solution was washed with water and saturated sodium chloride, dried over anhydrous sodium sulfate and then concentrated under reduced pressure. The residue was crystallized from methylene chloride-hexane and washed with hexane to give 31.8 g (37%) of the objective compound.

Melting point: 183.7°–185.0° C.
IR(KBr) $\nu$ cm$^{-1}$: 1596, 1565, 1561, 1496, 1451, 1119
NMR(90 MHz, CDCl$_3$) $\delta$ ppm: 7.46–6.81(5H, m), 4.03–3.56(4H, m), 2.50(3H, s), 1.88–1.42(2H, m), 0.91(3H, t, J=7.6 Hz)

The following compounds were prepared in a similar manner as EXAMPLE 68.

EXAMPLE 69

5-amino-4-(N,N-dimethylamino)-6-mercapto-2-methylpyrimidine
Yield: 68%
Melting point: 193.4° C. (decomposition)
IR(KBr) $\nu$ cm$^{-1}$: 1568, 1523, 1393, 1382, 1145, 923
NMR(90 MHz, DMSO-d$_6$) $\delta$ ppm: 13.09(1H, s), 4.62(2H, s), 2.96(6H, s), 2.28(3H, s)

EXAMPLE 70

5-amino-4-(N,N-diethylamino)-6-mercapto-2-methylpyrimidine
Yield: 83%
Melting point: 172.1–°173.2° C.
IR(KBr) $\nu$ cm$^{-1}$: 3305, 1577, 1506, 1429
NMR(90 MHz, CDCl$_3$) $\delta$ ppm: 12.81(1H, s), 4.12(2H, s), 3.51(4H, q, J=7.0 Hz), 2.44(3H, s), 1.16(6H, t, J=7.0 Hz)

EXAMPLE 71

5-amino-4-(N,N-dipropylamino)-6-mercapto-2-methylpyrimidine
Yield: 83%
Melting point: 144.1°–144.7° C.
IR(KBr) $\nu$ cm$^{-1}$: 2960, 2873, 1570, 1500, 1419, 1358, 1142
NMR(90 MHz, CDCl$_3$) $\delta$ ppm: 12.48(1H, br.s), 4.11(2H, br.s), 3.42(4H, t, J=7.4 Hz), 2.43(3H, s), 1.80–1.32(4H, m), 0.87(6H, t, J=7.1 Hz)

EXAMPLE 72

5-amino-4-(N,N-dibutylamino)-6-mercapto-2-methylpyrimidine
Yield: 76%
Melting point: 140.6°–141.8° C.
IR(KBr) $\nu$ cm$^{-1}$: 3310, 3012, 2958, 2931, 2873, 1571, 1499
NMR(90 MHz, CDCl$_3$) $\delta$ ppm: 3.45(4H, t, J=7.1 Hz), 2.41(3H, s), 1.74–1.02(8H, m), 0.92(6H, t, J=6.6 Hz)

EXAMPLE 73

5-amino-4-(N,N-dihexylamino)-6-mercapto-2-methylpyrimidine
Yield: 75%
Melting point: 112.2°–113.0° C.
IR(KBr) $\nu$ cm$^{-1}$: 3308, 3016, 2929, 1572, 1498, 1422, 1144
NMR(90 MHz, CDCl$_3$) $\delta$ ppm: 12.57(1H, s), 4.10(2H, br.s), 3.45(4H, t, J=7.3 Hz), 2.43(3H, s), 1.71–1.05(16H, m), 0.87(6H, t, J=5.4 Hz)

EXAMPLE 74

5-amino-4-(N,N-diphenylamino)-6-mercapto-2-methylpyrimidine
Yield:78%
Melting point: 239.4°–242.5° C.
IR(KBr) $\nu$ cm$^{-1}$: 1577, 1559, 1491, 1396, 1376, 1229, 1121, 696
NMR(90 MHz, DMSO-d$_6$) $\delta$ ppm: 13.75(1H, s),7.38–6.88(10H, m), 4.20(2H, br.s), 2.24(3H, s)

EXAMPLE 75

5-amino-4-(N-benzyl-N-ethylamino)-6-mercapto-2-methylpyrimidine
Yield: 93%
Melting point: 148.9°–149.7° C.
IR(KBr) $\nu$ cm$^{-1}$: 3005, 2881, 1560, 1498, 1450,
NMR(90 MHz, DMSO-d$_6$) $\delta$ ppm: 13.20(1H, br.s), 7.40–7.04(5H, m), 4.65(2H, s), 3.40(2H, q, J=7.1 Hz), 2.26(3H, s), 1.05(3H, t, J=7.1 Hz)

EXAMPLE 76

5-amino-4-(N-benzyl-N-heptylamino)-6-mercapto-2-methylpyrimidine
Yield: 80%
Melting point: 138.9°–140.3° C.
IR(KBr) $\nu$ cm$^{-1}$: 3324, 2928, 1559, 1527
NMR(90 MHz, CDCl$_3$ ) $\delta$ ppm: 12.14(1H, s), 7.48–7.14(5H, m), 4.76(2H, s), 4.16(2H, br.s), 3.42(2H, t, J=7.4 Hz), 2.41(3H, s), 1.74–1.02(10H, m), 0.87(3H, t, J=5.9 Hz)

EXAMPLE 77

5-amino-4-(N-butylamino)-6-mercapto-2-methylpyrimidine
Yield: 12%
Melting point: 216.8°–231.9° C.
IR(KBr) $\nu$ cm$^{-1}$: 3330, 2953, 2929, 2871, 1630, 1588
NMR(90 MHz, DMSO-d$_6$) $\delta$ ppm: 12.61(1H, s), 6.51(1H, t, J=6.4 Hz), 4.52(2H, br.s), 3.54–3.12(2H, m), 2.26(3H, 1.71–1.11(4H, m), 0.90(3H, t, J=6.3 Hz)

EXAMPLE 78

5-amino-4-mercapto-2-methyl-6-morpholinopyrimidine
Yield: 87%
Melting point: 203.1°–205.8° C.
IR(KBr) $\nu$ cm$^{-1}$: 2892, 1575, 1439, 1344, 1109, 916
NMR(90 MHz, CDCl$_3$ ) $\delta$ ppm: 12.84(1H, br.s), 3.87–3.36(8H, m), 2.47(3H, s)

EXAMPLE 79

5-amino-4-mercapto-2-methyl-6-(4-methylpiperazinyl)pyrimidine
Yield: 45%
Melting point: 237.9°–242.8° C.
IR(KBr) $\nu$ cm$^{-1}$: 3464, 3433, 1637, 1589, 1564, 1433
NMR(90 MHz, CDCl$_3$) $\delta$ ppm: 4.59(2H, br.s), 3.45–3.24(4H, m), 2.52–2.34(4H, m), 2.28(3H, s), 2.19(3H, s)

EXAMPLE 80

5-amino-4-mercapto-6-(N-phenyl-N-propylamino)-pyrimidine
Yield: 58%
Melting point: 176.4°–178.9° C.
IR(KBr) $\nu$ cm$^{-1}$: 1579, 1550, 1450, 1422, 1118
NMR(90 MHz, CDCl$_3$) $\delta$ ppm: 7.81(1H, s), 7.47–6.90(5H, m), 4.05(2H, br.s), 3.95(2H, t, J=7.6 Hz), 1.82–1.38(2H, m), 0.92(3H, t, J=7.3 Hz)

EXAMPLE 81

5-amino-4-(N,N-diethylamino)-6-mercaptopyrimidine

Yield: 85%
Melting point: 201.1°–202.1° C.
IR(KBr) ν cm$^{-1}$: 2968, 2889, 1591, 1552, 1506, 1429, 1373, 1120
NMR(90 MHz, DMSO-d$_6$) δ ppm: 13.32(1H, br.s), 7.76(1H, s), 3.40(4H, q, J=6.9 Hz), 1.06(6H, t, J=6.9 Hz)

EXAMPLE 82

5-amino-4-(N,N-dibutylamino)-6-mercaptopyrimidine
Yield: 57%
Melting point: 122.1°–122.6° C.
IR(KBr) ν cm$^{-1}$: 2956, 2872, 1587, 1552, 1504, 1427, 1358
NMR(90 MHz, CDCl$_3$) δ ppm: 7.74(1H, s), 4.30(2H, br.s),3.42(4H, t, J=7.3 Hz), 1.77–1.08(8H, m), 0.91(6H, t, J=6.3 Hz)

EXAMPLE 83

5-amino-4-(N,N-diethylamino)-2-(N,N-dimethylamino)-6-mercaptopyrimidine
Yield: 72%
Melting point: 161.0°–162.1° C.
IR(KBr) ν cm$^{-1}$: 2962, 1591, 1564, 1516, 1348, 1325
NMR(90 MHz, CDCl$_3$) δ ppm: 3.62(4H, q, J=6.9 Hz), 3.08(6H, s), 1.20(6H, t, J=6.9 Hz)

EXAMPLE 84

5-amino-4-(N,N-dibutylamino)-2-(N,N-dimethylamino)-6-mercaptopyrimidine
Yield: 74%
Melting point: 140.1°–142.9° C.
IR(KBr) ν cm$^{-1}$: 2956, 2931, 1593, 1566, 1504, 1331
NMR(90 MHz, DMSO-d$_6$) δ ppm: 11.0(1H, br.s), 4.02(2H, br.s), 3.50(4H, t, J=6.9 Hz), 3.00(6H, s), 1.80–0.96(8H, m), 0.88(6H, t, J=5.9 Hz)

EXAMPLE 85

5-amino-4-(N,N-diethylamino)-6-mercapto-2-methoxypyrimidine
Yield: 41%
Melting point: 147.4°–151.9° C.
IR(KBr) ν cm$^{-1}$: 1618, 1570, 1514, 1425, 1340, 1026
NMR(90 MHz, DMSO-d$_6$) δ ppm: 12.82(1H, br.s), 4.16(2H, br.s), 3.83(3H, s), 3.56(4H, J=6.9 Hz), 1.14(6H, t, J=6.9 Hz)

EXAMPLE 86

5-amino-4-(N,N-diethylamino)-6-mercapto-2-methylthiopyrimidine
Yield: 58%
Melting point: 166.6°–172.1° C.
IR(KBr) ν cm$^{-1}$: 2868, 2850, 1549, 1512, 1423, 1344, 1313
NMR(90 MHz, DMSO-d$_6$) δ ppm: 13.30(1H, br.s), 4.41(2H, br.s), 3.50(4H, q, J=6.9 Hz), 2.46(3H, s), 1.11(6H, t, J=6.9 Hz)

EXAMPLE 87

5-amino-4-methoxy-2-methyl-6-(N-phenyl-N-propylamino)pyrimidine
Yield: 56%
Melting point: 55.9°–57.5° C.
IR(KBr) ν cm$^{-1}$: 1575, 1492, 1471, 1426, 1405, 1203
NMR(90 MHz, CDCl$_3$) δ ppm: 7.39–6.71(5H, m), 3.99(3H, s), 3.91(2H, t, J=7.6 Hz), 3.04(2H, br.s), 2.49(3H, s), 1.92–1.44(2H, m), 0.92(3H, t, J=7.3 Hz)

EXAMPLE 88

5-amino-4-(N,N-diethylamino)-6-methoxy-2-methylpyrimidine
Yield: 62%
IR(neat) ν cm$^{-1}$: 3426, 3338, 1579, 1467, 1428, 1211
NMR(90 MHz, CDCl$_3$) δ ppm: 3.97(3H, s), 3.54–3.06(2H, m), 3.27(4H, q, J=6.9 Hz), 2.44(3H, s), 1.07(6H, t, J=6.9 Hz)

EXAMPLE 89

5-amino-4-(N,N-dipropylamino)-6-methoxy-2-methylpyrimidine
Yield: 86%
IR(neat) ν cm$^{-1}$: 2960, 1579, 1470, 1427, 1203
NMR(90 MHz, CDCl$_3$) δ ppm: 3.96(3H, s), 3.30(2H, br.s), 3.18(4H, t, J=7.3 Hz), 2.43(3H, s), 1.74–1.26(4H, m), 0.86(6H, t, J=7.3 Hz)

EXAMPLE 90

5-amino-4-(N,N-dibutylamino)-6-methoxy-2-methylpyrimidine
Yield: 79%
IR(neat) ν cm$^{-1}$: 3433, 3342, 2958, 2870, 1579, 1470, 1427, 1196
NMR(90 MHz, CDCl$_3$) δ ppm: 3.96(3H, s), 3.27(2H, br.s), 3.21(4H, t, J=7.3 Hz), 2.43(3H, s), 1.67–1.03(8H, m), 0.89(6H, t, J=5.9 Hz)

EXAMPLE 91

5-amino-4-(N,N-dibutylamino)-6-ethoxy-2-methylpyrimidine
Yield: 82%
IR(neat) ν cm$^{-1}$: 2958, 2929, 2872, 1578, 1443, 1381, 1196, 1072
NMR(90 MHz, CDCl$_3$) δ ppm: 4.39(2H, q, J=7.1 Hz), 3.20(4H, t, J=7.3 Hz), 3.12(2H, br.s), 2.41(3H, s), 1.39(3H, t, J=7.1 Hz), 1.74–1.02(8H, m), 0.89(6H, t, J=5.6 Hz)

EXAMPLE 92

5-amino-4-(N,N-dibutylamino)-6-ethoxy-pyrimidine
Yield: 42%
IR(neat) ν cm$^{-1}$: 2956, 2929, 1578, 1450, 1383, 1194, 1053
NMR(90 MHz, CDCl$_3$) δ ppm: 8.05(1H, s), 4.43(2H, q, J=7.0 Hz), 3.49(2H, br.s), 3.22(4H, t, J=7.1 Hz), 1.89–1.05(8H, m), 1.42(3H, t, J=7.0 Hz), 0.89(6H, t, J=5.9 Hz)

EXAMPLE 93

5-amino-4-(N,N-diethylamino)-6-methoxy-methylthiopyrimidine
Yield: 90.5%
IR(neat) ν cm$^{-1}$: 1568, 1462, 1416, 1387, 1336, 1306, 1211
NMR(90 MHz,CDCl$_3$) δ ppm: 3.96(3H,s),3.33(4H,q,J=7.0 Hz),2.50(3H,s),1-10(6H,t J=7.0 Hz)

EXAMPLE 94

5-amino-4-(N,N-diethylamino)-2,6-dimethoxypyrimidine
Yield: 91%
IR(neat) ν cm$^{-1}$: 2970, 1589, 1466, 1396, 1375, 1217, 1088
NMR(90 MHz, CDCl$_3$) δ ppm: 3.97(3H, s), 3.87(3H, s), 3.40(4H, q, J=7.1 Hz), 1.13(6H, t, J=7.1 Hz)

EXAMPLE 95

5-amino-2-methyl-4-methylthio-6-(N-phenyl-N-propylamino)pyrimidine
Yield: 49%
Melting point: 66.5°–67.4° C.
IR(KBr) $\nu$ cm$^{-1}$: 1598, 1541, 1487, 1425, 1401, 1216, 1116
NMR(90 MHz, CDCl$_3$) $\delta$ ppm: 7.41–6.86(5H, m), 3.92(2H, t, J=7.3 Hz), 3.09(2H, br.s), 2.61(3H, s), 2.55(3H, s), 1.86–1.37(2H, m), 0.92(3H, t, J=7.3 Hz)

EXAMPLE 96

5-amino-4,6-bis(N,N-diethylamino)-2-methylpyrimidine
Yield: 93%
IR(neat) $\nu$ cm$^{-1}$: 2967, 2931, 1570, 1459, 1432, 1421, 1224
NMR(90 MHz, CDCl$_3$) $\delta$ ppm: 3.27(8H, q, J=7.0 Hz), 2.43(3H, s), 1.09(12H, t, J=7.0 Hz)

EXAMPLE 97

5-amino-4,6-bis(hexylamino)-2-methylpyrimidine
Yield: 52%
Melting point: 65.0°–65.7° C.
IR(KBr) $\nu$ cm$^{-1}$: 3326, 2927, 2856, 1593, 1500, 1419, 1190
NMR(90 MHz, CDCl$_3$) $\delta$ ppm: 4.77(2H, br.s), 3.40(4H, dt, J=5.9 and 6.4 Hz), 2.39(3H, s), 1.56–1.02(16H, m), 0.89(6H, t, J=4.9 Hz)

EXAMPLE 98

5-amino-4-hydroxy-2-methyl-6-(N-phenylpropylamino)pyrimidine
Yield: 80%
Melting point: 93.8°–96.7° C.
IR(KBr) $\nu$ cm$^{-1}$: 1654, 1648, 1490, 1405
NMR(90 MHz, CDCl$_3$) $\delta$ ppm: 7.44–7.11(3H, m), 7.02–6.72(2H, m), 3.88(2H, t, J=7.4 Hz), 2.84(2H, br.s), 2.42(3H, s), 1.95–1.41(2H, m), 9.93(3H, t, J=7.4 Hz)

EXAMPLE 99

5-amino-4-mercapto-2-methyl-6-propylthiopyrimidine
Yield: 91%
Melting point: 178.3°–180.2° C.
IR(KBr) $\nu$ cm$^{-1}$: 3404, 3305, 2869, 1571, 1550, 1344, 1295, 1281, 1104
NMR(90 MHz, CDCl$_3$) $\delta$ ppm: 12.27(1H, s), 4.56(2H, br.s), 3.20(2H, t, J=7.1 Hz), 2.49(3H, s), 1.84–1.54(2H, m), 1.03(3H, t, J=7.3 Hz)

EXAMPLE 100

5-amino-4,6-bis(methylthio)-2-methylpyrimidine
Yield: 27%
Melting point: 123.3°–124.0° C.
IR(KBr) $\nu$ cm$^{-1}$: 3363, 3282, 3196, 2920, 1532, 1418, 1363, 798
NMR(90 MHz, CDCl$_3$) $\delta$ ppm: 3.61(2H, br.s), 2.61(6H, s), 2.55(3H, s)

EXAMPLE 101

5-amino-4,6-bis(hexylthio)-2-methylpyrimidine
Yield: 31%
IR(neat) $\nu$ cm$^{-1}$: 2930, 1526, 1523, 1419
NMR(90 MHz, CDCl$_3$) $\delta$ ppm: 3.64(2H, br.s), 3.24(4H, t, J=7.1 Hz), 2.52(3H, 2.04–1.08 (16H, m), 0.89(6H, t, J=5.6 Hz)

EXAMPLE 102

5-amino-4,6-dimethoxy-2-methylpyrimidine
Yield: 26%
Melting point: 98.2°–98.8° C.
IR(KBr) $\nu$ cm$^{-1}$: 1592, 1487, 1437, 1377, 1188, 1076
NMR(90 MHz, CDCl$_3$) $\delta$ ppm: 3.97(6H, s), 3.34(2H, br.s), 2.45(3H, s)

EXAMPLE 103

5-amino-4-chloro-6-(N,N-dimethylamino)pyrimidine
Yield: 10%
Melting point: 117.8°–118.0° C.
IR(KBr) $\nu$ cm$^{-1}$: 3370, 1627, 1557, 1531, 1403, 975
NMR(90 MHz, CDCl$_3$) $\delta$ ppm: 8.11(1H, s), 3.82(2H, br.s), 2.96(6H, s)

EXAMPLE 104

Preparation of 5-amino-4-(N,N-dimethylamino)-6-hexylaminopyrimidine

A suspension of the product obtained in EXAMPLE 103 (280mg) and hexylamine (2 ml) was refluxed for 7 hours. After cooling to room temperature, the reaction mixture was diluted with water and extracted with ethyl acetate. The organic layer was washed with water and saturated sodium chloride, dried over anhydrous sodium sulfate and then concentrated under reduced pressure. The residue was purified by silica gel column chromatography (ethyl acetate:hexane=1:1) followed by crystallization from ether-hexane to give 220mg (57%) of the objective compound.
Melting point: 123.2°–124.8° C.
IR(KBr) $\nu$ cm$^{-1}$: 3367, 3327, 2929, 1583, 1446, 1417, 1335
NMR(90 MHz, CDCl$_3$) $\delta$ ppm: 8.14(1H, s), 4.41(1H, br.s), 3.54–3.24(2H, m), 2.80(6H, s), 1.80–1.05(8H, m), 1.05–0.72(3H, m)

EXAMPLE 105

Preparation of 5-amino-4-(N,N-diethylamino)-2-methyl-6-methylthiopyrimidine

Starting from the product obtained in EXAMPLE 70, the objective compound was prepared in a similar manner as EXAMPLE 64.
Yield: 98%
IR(neat) $\nu$ cm$^{-1}$: 2967, 2929, 1542, 1430, 1375, 1364
NMR(90 MHz, CDCl$_3$) $\delta$ ppm: 3.50(2H, br.s), 3.27(4H, q, J=7.0 Hz), 2.60(3H, s), 2.48(3H, s), 1.09(6H, t, J=7.0 Hz)

EXAMPLE 106

Preparation of 4-hydroxy-6-isopropyl-2-methyl-5-phenylazopyrimidine

To a solution of aniline (17.66 g) in 3N hydrochloric acid (210 ml), a solution of sodium nitrite (13.1 g) in water (40 ml) was added dropwise under ice-cooling to give the solution of diazonium salt. To a solution of ethyl isobutyrylacetate (30 g) in ethanol (190 ml), a solution of sodium acetate (136 g) in water (75 ml) was added and then the solution of diazonium salt was added dropwise under ice-cooling. After stirring for 30 minutes under ice-cooling, the reaction mixture was diluted with water and extracted twice with ethyl acetate. The combined organic layer was washed with water, saturated sodium bicarbonate and saturated sodium chloride in order, dried over anhydrous sodium sulfate and then concentrated under reduced pressure to give the phenylazo-$\beta$-ketoester derivative. 28 g (55%)

of the objective compound was prepared from above obtained β-ketoester derivative in a similar manner as EXAMPLE 1.

Melting point: 171.3° C. (decomposition)

IR(KBr) ν cm⁻¹: 3473, 2966, 1654, 1581, 1545, 1457, 1431

NMR(90 MHz, CDCl₃) δ ppm: 7.98–7.14(2H, m), 7.62–7.38(3H, m), 4.71(1H, s), 4.20–3.60(1H, m), 2.60(3H, s), 1.31(6H, d, J=6.6 Hz)

EXAMPLE 107

Preparation of 5-amino-4-hydroxy-6-isopropyl-2-methylpyrimidine

To a suspension of the product obtained in EXAMPLE 106 (5.0 g) in 3N aqueous sodium hydroxide (10 ml), sodium hydrosulfite (10 g) was added and the mixture was stirred for 5 hours under reflux. After the addition of sodium hydrosulfite (5.0 g), the mixture was stirred for another 2 hours under reflux. The reaction mixture was poured into ice-water and extracted three times with ethyl acetate. The combined organic layer was washed with saturated sodium chloride, dried over anhydrous sodium sulfate and then concentrated under reduced pressure. The residue was purified by silica gel column chromatography (ethyl acetate:hexane=1:1 to ethyl acetate) followed by crystallization from ether-hexane to give 1.6 g (49%) of the objective compound.

Melting point: 170.9°–171.6° C.

IR(KBr) ν cm⁻¹: 3368, 2965, 1670, 1606, 1588, 1309

NMR(90 MHz, CDCl₃) δ ppm: 12.85(1H, br.s), 3.56(2H, br.s), 3.06–2.70(3H, s), 1.22(6H, d, J=6.9 Hz)

EXAMPLE 108

Preparation of ethyl 2-(N-phenyl-N-propylamino)acetate

To a solution of N-propylaniline (60 g) and ethyl bromoacetate (83.6 ml) in dioxane (60 ml), diazabicycloundecene (DBU;113 ml) was added dropwise under ice-cooling. After stirring for 1 hour at room temperature, the reaction mixture was diluted with water and extracted three times with ethyl acetate. The combined organic layer was washed with successive, 1N hydrochloric acid, water and saturated sodium chloride in order. After drying over anhydrous sodium sulfate, the solvent was evaporated under reduced pressure to give 87.9 g (90%) of the objective compound.

IR(neat) ν cm⁻¹: 2963, 1751, 1600, 1508, 1186, 748

NMR(90 MHz, CDCl₃) δ ppm: 7.32–7.05(2H, m), 6.81–6.51(3H, m), 4.18(2H, q, J=7.1 Hz), 4.02(2H, s), 3.34(2H, t, J=7.6 Hz), 1.81–1.44(2H, m), 1.25(3H, t, J=7.1 Hz), 0.94(3H, t, J=7.3 Hz)

EXAMPLE 109

Preparation of 2-(N-phenyl-N-propylamino)acetic acid

To a solution of the product obtained in EXAMPLE 108 (5.0 g) in ethanol (30 ml), 3N aqueous sodium hydroxide (30 ml) was added and the mixture was stirred for 10 minutes under reflux. The aqueous solution was concentrated under reduced pressure and washed with ether, acidified to pH 3 with 2N hydrochloric acid and extracted four times with ethyl acetate. The combined organic layer was washed with saturated sodium chloride, dried over anhydrous sodium sulfate and then concentrated under reduced pressure. The residue was crystallized from ethyl acetate-hexane to give 2.96 g (68%) of the objective compound.

Yield: 89.8°–91.4° C.

IR(KBr) ν cm⁻¹: 2955, 1709, 1599, 1508, 1236

NMR(90 MHz, CDCl₃) δ ppm: 7.38–7.08(2H, m), 6.90–6.60(3H, m), 5.05(1H, br.s), 4.05(2H, s), 3.33(2H, t, J=7.6 Hz), 1.92–1.44(2H, m), 0.94(3H, t, J=7.3 Hz)

EXAMPLE 110

Preparation of 3-(N-phenyl-N-propylamino)propionic acid

A mixture of N-propyl aniline (5.0 g), acrylic acid (5.1 ml) and water (7 ml) was stirred for 2 hours under reflux. After cooling to room temperature, the aqueous solution was adjusted to pH 11 with 5N aqueous sodium hydroxide and washed four times with ether. The aqueous layer was acidified to pH 3 with concentrated hydrochloric acid and extracted three times with ethyl acetate. The combined organic layer was washed with saturated sodium chloride, dried over anhydrous sodium sulfate and concentrated under reduced pressure to give 7.2 g (94%) of the objective compound.

IR(neat) ν cm⁻¹: 2958, 1716, 1600, 1506, 1367

NMR(90 MHz, CDCl₃) δ ppm: 7.38–7.08(2H, m), 6.90–6.63(3H, m), 3.61(2H, t, J=7.2 Hz), 3.23(2H, t, J=7.6 Hz), 2.61(2H, t, J=7.2 Hz), 1.86–1.38(2H, m), 0.92(3H, t, J=7.3 Hz)

EXAMPLE 111

Preparation of 4-(N-methyl-N-phenylamino)butanoic acid

A mixture of N-methylaniline (10 g), ethyl 4-bromobutyrate (13.2 ml) and potassium carbonate (12.7 g) was stirred for 1.5 hour at 110° C. After cooling to room temperature, ethanol (100 ml) and 3N aqueous sodium hydroxide (100 ml) were added to the mixture, and the mixture was stirred for 30 minutes under reflux. After cooling to room temperature, the reaction mixture was concentrated under reduced pressure and the residue was diluted with water and then washed with ether. The aqueous layer was acidified to pH 4 with concentrated hydrochloric acid and extracted three times with ethyl acetate. The organic layers were collected and extracted twice with 3N hydrochloric acid. The aqueous layers were collected, adjusted to pH 4 by using 20% NaCl aqueous solution, and extracted five times with an ethyl acetate. The combined organic layer was washed with water and saturated sodium chloride, dried over anhydrous sodium sulfate and then concentrated under reduced pressure to give 14.8 g (84%) of the objective compound.

IR(neat) ν cm⁻¹: 2942, 1702, 1600, 1508, 1375, 1194

NMR(90 MHz, CDCl₃) δ ppm: 10.74(1H, br.s), 7.32–7.08(2H, m), 6.81–6.57(3H, m), 3.36(2H, t, J=7.1 Hz), 2.91(3H, s), 2.40(2H, t, J=7.3 Hz), 2.07–1.74(2H, m)

The following compounds were prepared in a similar manner as EXAMPLE 111.

EXAMPLE 112

4-(N-phenyl-N-propylamino)butyric acid

Yield: 73%

IR(neat) ν cm⁻¹: 2962, 1716, 1599, 1506, 747

NMR(90 MHz, CDCl₃) δ ppm: 7.34–7.10(2H, m), 6.76–6.54(3H, m), 3.30(2H, t, J=7.3 Hz), 3.26(2H, t, J=7.6 Hz), 2.41(2H, t, J=7.6 Hz), 2.22–1.32(4H, m), 0.91(3H, t, J=7.3 Hz)

EXAMPLE 113

3-(N-hexyl-N-phenylamino)propionic acid

Yield: 39%

IR(neat) ν cm⁻¹: 2929, 2858, 1713, 1599, 1506, 1367, 1194, 746

NMR(270 MHz, CDCl₃) δ ppm: 7.32–7.22(2H, m), 6.89–6.78(3H, m), 3.57(2H, t, J=7.0 Hz), 3.23(2H, t, J=7.6 Hz), 2.60(2H, t, J=7.0 Hz), 1.60–1.46(2H, m), 1.38–1.21(6H, m), 0.88(3H, t, J=6.6 Hz)

EXAMPLE 114

4-(N-hexyl-N-phenylamino)butyric acid
Yield: 41%

IR(neat) ν cm⁻¹: 2927, 1708, 1598, 1507, 1370, 1192, 746, 694

NMR(90 MHz, CDCl₃) δ ppm: 9.81(1H, br.s), 7.32–7.02(2H, m), 6.78–6.48(3H, m), 3.33(2H, t, J=7.3 Hz), 3.24(2H, t, J=7.4 Hz), 2.42(2H, t, J=6.8 Hz), 2.10–1.68(2H, m), 1.68–1.02(8H, m), 0.89(3H, t, J=5.3 Hz)

EXAMPLE 115

4-(N-cycloheptyl-N-phenylamino) butyric acid
Yield: 59%

IR (neat) ν cm⁻¹: 2927, 2858, 1732, 1711, 1597, 1502

NMR(270 MHz, CDCl₃) δ ppm: 7.29(2H, dd, J=8.3 and 7.3 Hz), 7.01(2H, d, J=8.3 Hz), 6.92(1H, t, J=7.3 Hz), 3.62–3.50(1H, m), 3.28(2H, t, J=7.3 Hz), 2.47(2H, t, J=6.7 Hz), 2.06–1.34(14H, m)

EXAMPLE 116

4-(N-decyl-N-phenylamino)butyric acid
Yield: 40%

IR(neat) ν cm⁻¹: 2921, 2856, 1702, 1598, 1508, 746

NMR(90 MHz, CDCl₃) δ ppm: 7.32–7.08(2H, m), 6.78–6.54(3H, m), 3.33(2H, t, J=7.3 Hz), 3.25(2H, t, J=7.6 Hz), 2.43(2H, t, J=6.8 Hz), 2.07–1.74(2H, m), 1.68–1.08(16H, m), 0.88(3H, t, J=6.6 Hz)

EXAMPLE 117

4-[N-(4-butylphenyl)-N-propylamino]butyric acid
Yield: 37%

IR(neat) ν cm⁻¹: 2957, 2931, 1708, 1617, 1521, 1191, 1170

NMR(90 MHz, CDCl₃) δ ppm: 9.78(1H, br.s), 7.05(2H, d, J=8.9 Hz), 6.69 (2H, d, J=8.9 Hz), 3.31(2H, t, J=7.1 Hz), 3.18(2H, t, J=7.6 Hz), 2.51(2H, t, J=7.3 Hz), 2.43(2H, t, J=6.3 Hz), 2.04–1.08(8H, m), 0.92(3H, t, J=7.3 Hz), 0.90(3H, t, J=7.3 Hz)

EXAMPLE 118

4-[N-(4-methoxyphenyl)-N-propylamino]butyric acid
Yield: 29%

IR(neat) ν cm⁻¹: 2966, 1719, 1509, 1242, 1181, 1037

NMR(90 MHz, CDCl₃) δ ppm: 10.81(1H, br.s), 6.87(4H, s), 3.77(3H, s), 3.36–2.94(4H, m), 2.96(2H, t, J=6.8 Hz), 2.04–1.32(4H, m), 0.88(3H, t, J=7.3 Hz)

EXAMPLE 119

4[N-(3-methoxyphenyl)-N-propylamino]butyric acid
Yield: 77%

IR(neat) ν cm⁻¹: 2937, 1709, 1610, 1576, 1500, 1211, 1159

NMR(270 MHz, CDCl₃) δ ppm: 7.12(1H, t, J=8.6 Hz), 6.32(1H, dd, J=8.2 and 2.3 Hz), 6.29–6.22(2H, m), 3.79(3H, s), 3.33(2H, t, J=7.4 Hz), 3.21(2H, t, J=7.8 Hz), 2.42(2H, t, J=7.1 Hz), 1.99–1.86(2H, m), 1.69–1.51(2H, m), 0.91(3H, t, J=7.4 Hz)

EXAMPLE 120

[N-(1,3-benzodioxol-5-yl)-N-propylamino]butyric acid
Yield: 83%

IR(neat) ν cm⁻¹: 1713, 1504, 1491, 1244, 1217, 1038

NMR(90 MHz, CDCl₃) δ ppm: 9.05(1H, br.s), 6.71(1H, d, J=8.3 Hz), 6.46(1H, d, J=2.3 Hz), 6.27(1H, dd, J=8.3 and 2.3 Hz), 5.88(2H, s), 3.22(2H, t, J=6.9 Hz), 3.10(2H, t, J=7.6 Hz), 2.43(2H, t, J=6.8 Hz), 2.07–1.14(4H, m), 0.89(3H, t, J=7.3 Hz)

EXAMPLE 121

4-[N-hexyl-N-(4-methoxyphenyl)amino]butyric acid
Yield: 82%

IR(neat) ν cm⁻¹: 2954, 2931, 1718, 1514, 1464, 1246, 1182

NMR(90 MHz, CDCl₃) δ ppm: 7.58(1H, br.s), 7.02–6.72(4H, m), 3.77 (3H, s.), 3.33–2.94(4H, m), 2.49(2H, t, J=6.6 Hz), 2.01–1.62(2H, m), 1.62–1.08(8H, m), 0.86(3H, t, J=4.6 Hz)

EXAMPLE 122

4-[N-hexyl-N-(2-methoxyphenyl)amino]butyric acid
Yield: 65%

IR(neat) ν cm⁻¹: 2956, 2931, 1736, 1500, 1464, 1240

NMR(270 MHz, CDCl₃) δ ppm: 7.27–7.15(2H, m), 6.98–6.91(2H, m), 3.87(3H, s), 3.22(2H, t, J=5.9 Hz), 3.12–3.04(2H, m), 2.58–2.51(2H, m), 1.87–1.76(2H, m), 1.46–1.30(2H, m), 1.30–1.15(6H, m), 0.84(3H, t, J=6.6 Hz)

EXAMPLE 123

4-[N-(2,4-difluorophenyl)-N-propylamino]butyric acid
Yield: 48%

IR(neat) ν cm⁻¹: 2966, 2934, 1710, 1508, 1273, 1142

NMR(90 MHz, CDCl₃) δ ppm: 7.14–6.60(3H, m), 3.24–2.82(4H, m), 2.43(2H, J=7.1 Hz), 1.92–1.62(2H, m), 1.62–1.20(2H, m), 0.86(3H, t, J=7.3 Hz)

EXAMPLE 124

4-(N-benzyl-N-propylamino)butyric acid
Yield: 42%

IR(neat) ν cm⁻¹: 2966, 17 18, 1577, 1457, 1406, 742, 701

NMR(90 MHz, CDCl₃) δ ppm: 11.41(1H, br.s), 7.62–7.20(5H, m), 4.02(2H, s), 3.06–2.52(4H, m), 2.52–2.16(2H, m), 2.10–1.44(4H, m), 0.90(3H, t, J=7.1 Hz)

EXAMPLE 125

4-(N-benzyl-N-heptylamino)butyric acid
Yield: 10%

IR(neat) ν cm⁻¹: 2955, 2929, 2857, 1718, 1458

NMR(90 MHz, CDCl₃) δ ppm: 8.38(1H, br.s), 7.56–7.32(5H, m), 4.03(2H, s), 3.06–2.64(4H, m), 2.55–2.34(2H, m), 2.10–1.80(2H, m), 1.41–1.08(10H, m), 0.86(3H, t, J=5.4 Hz)

EXAMPLE 126

4-tetrahydroquinolinobutyric acid
Yield: 62%

IR(KBr neat) ν cm⁻¹: 1702, 1498, 1245, 754

NMR(90 MHz, CDCl₃) δ ppm: 10.67(1H, br.s), 7.20–6.78(2H, m), 6.72–6.36(2H, m), 3.42–3.06(4H, m), 2.74(2H, t, J=6.3 Hz), 2.42(2H, t, J=6.8 Hz), 2.10–1.50(4H, m)

EXAMPLE 127

4-(4-phenylpiperazinyl)butyric acid
Yield: 24%
IR(KBr) $\nu$ cm$^{-1}$: 3384, 1598, 1579, 1498, 1394, 771
NMR(90 MHz, CDCl$_3$) $\delta$ ppm: 7.41–7.17(2H, m), 7.05–6.78(3H, m), 3.45–3.24(4H, m), 3.03–2.79(4H, m), 2.79–2.52(4H, m), 2.07–1.74(2H, m)

EXAMPLE 128

5-(N-phenyl-N-propylamino)pentanoic acid
Yield: 87%
IR(neat) $\nu$ cm$^{-1}$: 2956, 2875, 1716, 1710, 1599, 746
NMR(90 MHz, CDCl$_3$) $\delta$ ppm: 7.32–7.02(2H, m), 6.75–6.45(3H, m), 3.39–3.03(4H, m), 2.52–2.22(2H, m), 1.86–1.32(6H, m), 0.91(3H, t, J=7.3 Hz)

EXAMPLE 129

5-(N-hexyl-N-phenylamino)pentanoic acid
Yield: 72%
IR(neat) $\nu$ cm$^{-1}$: 2933, 2859, 1709, 1598, 1507, 746
NMR(90 MHz, CDCl$_3$) $\delta$ ppm: 7.32–7.08(2H, m), 6.72–6.51(3H, m), 3.36–3.12(4H, m), 2.49–2.25(2H, m), 1.80–1.14(12H, m), 0.89(3H, t, J=5.6 Hz)

EXAMPLE 130

5-(N-cyclohexyl-N-propylamino)pentanoic acid
Yield: 40%
IR(neat) $\nu$ cm$^{-1}$: 3398, 2943, 1716, 1456
NMR(270 MHz, DMSO-d$_6$) $\delta$ ppm: 3.04–2.88(1H, m), 2.88–2.70(4H, m), 2.25(2H, t, J=6.9 Hz), 1.98–1.86(2H, m), 1.82–1.71(2H, m), 1.69–1.00(12H,m), 0.88(3H, t, J=7.3 Hz)

EXAMPLE 131

6-(N-phenyl-N-propylamino)hexanoic acid
Yield: 10%
IR(neat) $\nu$ cm$^{-1}$: 2939, 1718, 1598, 1507, 1244
NMR(90 MHz, CDCl$_3$) $\delta$ ppm: 7.32–7.08(2H, m), 6.78–6.48(3H, m), 3.37–3.09(4H, m), 2.37(2H, t, J=7.1 Hz), 1.92–1.14(8H, m), 0.91(3H, t, J=7.3 Hz)

EXAMPLE 132

Preparation of N-[4-mercapto-2-methyl-6-(N-phenyl-N-propylamino)pyrimidin -5-yl]-2-(N-phenyl-N-propylamino)acetamide To a solution of the product obtained in EXAMPLE 68 (137 mg) and the product obtained in EXAMPLE 109 (116 mg) in methylene chloride (5 ml), N,N'-dicyclohexylcarbodiimide (134 mg) was added under ice-cooling and the solution was stirred for 1 hour at room temperature. The formed insoluble material was filtered off and the filtrate was diluted with 50 ml of ethyl acetate. The organic solution was washed with saturated sodium bicarbonate and saturated sodium chloride, dried over anhydrous sodium sulfate and then concentrated under reduced pressure. The residue was purifed by silica gel column chromatography (ethyl acetate:hexane=1:4–2:3) and followed by washing with ether to give 164 mg (73%) of the objective compound.
Melting point: 230.1°–231.1° C.
IR(KBr) $\nu$ cm$^{-1}$: 2959, 1654, 1596, 1561, 1506, 1457, 1421, 1229
NMR(90 MHz, DMSO-d$_6$) $\delta$ ppm: 13.17(1H, s), 8.21(1H, s), 7.44–6.90(7H, m), 6.68–6.32(3H, m), 4.02–3.78(2H, m), 3.17(2H, s), 3.12–2.88(2H, m), 2.37(3H, s), 1.86–1.32(4H, m), 0.85(6H, t, J=6.9 Hz)

The following compounds were prepared in a similar manner as EXAMPLE 132.

EXAMPLE 133

N-[4-(N,N-diethylamino)-6-mercapto-2-methyl-pyrimidin-5-yl]-2-(N-phenyl-N-propylamino)acetamide
Yield: 17%
Melting point: 200.0°–201.2° C.
IR(KBr) $\nu$ cm$^{-1}$: 1655, 1601, 1561, 1542, 1527, 1508
NMR(90 MHz, DMSO-d$_6$) $\delta$ ppm: 12.77(1H, s), 8.73(1H, S), 7.12(2H, t, J=7.9 Hz), 6.75–6.51(3H, m), 4.05(2H, s), 1.74–1.44(2H, m), 1.14–0.80(6H, m)

EXAMPLE 134

N-[4-(N,N-diphenylamino)-6-mercapto-2-methyl-pyrimidin-5-yl]-2-(N-phenyl-N-propylamino)acetamide
Yield: 48%
Melting point: 194.1°–195.7° C.
IR(KBr) $\nu$ cm$^{-1}$: 1686, 1535, 1521, 1492, 1465, 1451, 1240, 748, 696
NMR(90 MHz, DMSO-d$_6$) $\delta$ ppm: 13.55(1H, s), 8.53(1H, s), 7.34–6.94(12H, m), 6.60–6.37(3H, m), 3.34(2H, s),. 3.00(2H, t, J=8.6 Hz), 2.22(3H, s), 1.64–1.26(2H, m), 0.84(3H, t, J=6.9 Hz)

EXAMPLE 135

N-[4-methoxy-2-methyl-6-(N-phenyl-N-propylamino)pyrimidin -5-yl]-2-(N-phenyl-N-propylamino)acetamide
Yield: 16%
Melting point: 152.8°–153.4° C.
IR (KBr) $\nu$ cm$^{-1}$: 3201, 1666, 1555, 1496, 1415, 1376, 1127
NMR (90 MHz, CDCl$_3$ ) $\delta$ ppm: 7.41–6.36(10H, m), 3.91(2H, t, J=7.6 Hz), 3.74(3H, s), 3.36(2H, s), 2.83(2H, t, J=7.6 Hz), 2.47(3H, s), 1.82–1.01(4H, m), 1.01–0.69(6H, m)

EXAMPLE 136

N-[4-hydroxy-2-methyl-6-(N-phenyl-N-propylamino)pyrimidin -5-yl]-2-(N-phenyl-N-propylamino)acetamide
Yield: 63%
Melting point: 197.3°–198.4° C.
IR(KBr) $\nu$ cm$^{-1}$: 1654, 1618, 1560, 1507, 1496, 1458, 1414
NMR(90 MHz, DMSO-d$_6$) $\delta$ ppm: 12.01(1H, s), 7.96(1H, s), 7.50–7.14(7H, m), 6.66–6.24(3H, m),. 3.84(2H, t, J=7.0 Hz), 3.14 (2H, s), 2.97(2H, t, J=7.0 Hz), 2.25(3H, s), 1.80–1.02(4H, m), 0.84(6H, t, J=6.9 Hz)

EXAMPLE 137

N-(4-mercapto-2-methyl-6-propylthiopyrimidin-5-yl)-2-(N-phenyl-N-propylamino)acetamide
Yield: 26%
Melting point: 184.7°–186.8° C.
IR(KBr) $\nu$ cm$^{-1}$: 2964, 1684, 1591, 1577, 1554, 1521, 1507, 1492
NMR(90 MHz, DMSO-d$_6$) $\delta$ ppm: 13.81(1H, s), 9.13(1H, s), 7.26–7.00(2H, m), 6.79–6.49(3H, m), 4.02(2H, s), 3.46–3.16(2H, m), 3.03(2H, t, J=6.8 Hz), 2.41(3H, s), 1.72–1.50(4H, m), 1.09–0.78(6H, m)

EXAMPLE 138

N-[4-mercapto-2-methyl-6-(N-phenyl-N-propylamino)pyrimidin-5-yl]-3-(N-phenyl-N-propylamino)propionamide
Yield: 36%
Melting point: 130.6°–132.4° C.
IR(KBr) ν cm$^{-1}$: 2957, 1595, 1560, 1506, 1459, 1423
NMR (90 MHz, DMSO-d$_6$) δ ppm: 13.09(1H, s), 8.16(1H, s), 7.38–6.90(7H, m), 6.66–6.42(3H, m), 4.02–3.75(2H, m), 3.28–2.94(4H, m), 2.08(3H, s), 1.94–1.02(6H, m), 0.85(6H, t, J=6.6 Hz)

EXAMPLE 139

N-[4-(N,N-diethylamino)6-mercapto-2-methyl-pyrimidin-5-yl]-3-(N-phenyl-N-propylamino)propionamide
Yield: 25%
Melting point: 182.7°–186.4° C.
IR(KBr) ν cm$^{-1}$: 2964, 2869, 1674, 1607, 1564, 1506, 1320
NMR(90 MHz, DMSO-d$_6$) δ ppm: 12.73(1H, s), 8.90(1H, s), 7.26–6.93(2H, m), 6.72–6.48(3H, m), 4.02–3.06(8H, m), 2.67–2.37(2H, m), 2.28(3H, s), 1.74–1.32(2H, m), 1.07(6H, t, J=7.1 Hz), 0.89(3H, t, J=7.6 Hz)

EXAMPLE 140

N-[4-methoxy-2-methyl-6-(N-phenyl-N-propylamino)pyrimidin-5-yl]-3-(N-phenyl-N-propylamino)propionamide
Yield: 6%
Melting point: 124.4°–125.2° C.
IR(KBr) ν cm$^{-1}$: 1660, 1578, 1550, 1506, 1495, 1372
NMR(90 MHz, CDCl$_3$) δ ppm: 7.34–6.47(10H, m), 3.87(3H, s), 4.04–3.73(2H, m), 3.54–2.96(4H, m), 2.50(3H, s), 1.95–1.09(6H, m), 0.88(6H, t, J=6.6 Hz)

EXAMPLE 141

N-[4-hydroxy-2-methyl-6-(N-phenyl-N-propylamino)pyrimidin-5-yl]-3-(N-phenyl-N-propylamino)propionamide
Yield: 23%
Melting point: 90.5°–91.4° C.
IR(KBr) ν cm$^{-1}$: 1654, 1617, 1596, 1560, 1507
NMR(90 MHz, DMSO-d$_6$) δ ppm: 12.01(1H, s), 8.14(1H, s), 7.35–6.75(7H, m), 6.60–6.24(3H, m), 4.00–3.60(2H, m), 3.24–2.88(4H, m), 2.25(3H, s), 1.92–1.30(6H, m), 1.02–0.72(6H, m)

EXAMPLE 142

N-[4-(N,N-diethylamino)-6-mercapto-2-methylpyrimidin-5-yl]-3-(N-hexyl-N-phenylamino)propionamide
Yield: 50%
Melting point: 166.5°–168.2° C.
IR(KBr) ν cm$^{-1}$: 2960, 2929, 1605, 1564, 1506, 1431, 1321
NMR(270 MHz, DMSO-d$_6$) δ ppm: 12.76(1H, s), 8.92(1H, s), 7.15(2H, dd, J=8.3 and 7.3 Hz), 6.68(2H, d, J=8.3 Hz), 6.57(1H, t, J=7.3 Hz), 3.62–3.51(2H, m), 3.44(4H, q, J=6.9 Hz), 3.28(2H, t, J=7.4 Hz), 2.56–2.44(2H, m), 2.28(3H, s), 1.58–1.43(2H, m), 1.35–1.20(6H, m), 1.06(6H, t, J=6.9 Hz), 0.87(3H, t, J=6.8 Hz)

EXAMPLE 143

N-[4-mercapto-2-methyl-6-(N-phenyl-N-propylamino)pyrimidin-5-yl]-4-(N-phenyl-N-propylamino)butanamide
Yield: 41%
Melting point: 131.8°–134.2° C.
IR(KBr) ν cm$^{-1}$: 2958, 1595, 1560, 1505, 1466, 1459, 1423
NMR(90 MHz, DMSO-d$_6$) δ ppm: 13.06(1H, s), 7.87(1H, s), 7.38–6..84(7H, m), 6.72–6.42(3H, m), 3.85(2H, t, J=6.9 Hz), 3.29–3.00(4H, m), 2.37(3H, s), 1.75–1.28(8H, m), 0.87(3H, t, J=6.9 Hz), 0.84(3H, t, J=7.3 Hz)

EXAMPLE 144

N-[4-(N,N-dimethylamino)-6-mercapto--2methylpyrimidin-5-yl]-4-(N-phenyl-N-propylamino)-butanamide
Yield: 24%
194.8–197.6° C.
Melting point:
IR(KBr) ν cm$^{-1}$: 1761, 1606, 1570, 1506, 1398
NMR(90 MHz]DMSO-d$_6$) δ ppm: 12.75(1H, s), 8.75(1H, s), 7.26–6.93(2H, m), 6.78–6.36(3H, m), 3.36–2.84(4H, m), 3.04(6H, s), 2.28(3H, s), 2.04–1.20(6H, m), 0.88(3H, t, J=7.3 Hz)

EXAMPLE 145

N-[4-(N,N-diethylamino)-6-mercapto-2-methylpyrimidin-5-yl]-4-(N-phenyl-N-propylamino)butanamide
Yield: 60%
Melting point: 172.4°–174.5° C.
IR(KBr) ν cm$^{-1}$: 3212, 1677, 1608, 1566, 1506
NMR(90 MHz, DMSO-d$_6$) δ ppm: 12.71(1H, s), 8.79(1H, s), 7.26–6.90(2H, m), 6.78–6.36(3H, m), 3.66–2.82(8H, m), 2.27(3H, s), 2.04–1.20(6H, m), 1.00(6H, t, J=6.9 Hz), 0.88(3H, t, J=7.1 Hz)

EXAMPLE 146

N-[4-(N,N-dibutylamino)-6-mercapto2-methyl-pyrimidin-5-yl]-4-(N-phenyl-N-propylamino)butanamide
Yield: 84%
Melting point: 170.8°–171.9° C.
IR(KBr) ν cm$^{-1}$: 2957, 2930, 2870, 1608, 1562, 1506
NMR(90 MHz, DMSO-d$_6$) δ ppm: 12.71(1H, s), 8.79(1H, s), 7.20–6.90(2H, m), 6.72–6.33(3H, m), 3.60–3.30(8H, m), 2.36–2.16(2H, m), 2.26(3H, s), 1.98–0.98(12H, m), 0.87(9H, t, J=6.3 Hz)

EXAMPLE 147

N-[4-(N,N-dihexylamino)-6-mercapto-2-methyl-pyrimidin-5-yl]-4-(N-phenyl-N-propylamino)butanamide
Yield: 45%
Melting point: 143.3°–145.6° C.
IR(KBr) ν cm$^{-1}$: 2956, 2929, 1676, 1610, 1567, 1506
NMR(90 MHz, DMSO-d$_6$) δ ppm: 12.70(1H, s), 8.76(1H, s), 7.20–6.93(2H, m), 6.72–6.36(3H, m), 3.60–3.00(8H, m), 2.26(3H, s), 1.98–1.65(2H, 1.65–0.99(20H, m), 0.99–0.69(9H, m)

EXAMPLE 148

N-[4-(N-benzyl-N-heptylamino)-6-mercapto-2-methylpyrimidin -5-yl]-4-(N-phenyl-N propylamino)-butanamide Yield: 52%
Melting point: 123.4°–124.7° C.
IR(KBr) ν cm⁻¹: 3219, 2870, 2855, 1648, 1599, 1564, 1561
NMR(90 MHz, DMSO-d₆) δ ppm: 12.89(1H, s), 8.80(1H, s), 7.44–6.84(7H, m), 6.72–6.30(3H, m), 4.98–4.50(2H, m), 3.48–2.76(6H, m), 2.27(3H, s), 2.34–1.98(2H, m), 1.92–0.96(14H, m), 0.96–0.66(6H, m)

EXAMPLE 149

N-[4-mercapto-6-(N-phenyl-N-propylamino)pyrimidin-5-yl]-(N-phenyl-N-propylamino)butanamide
Yield: 39%
Melting point: 138.7°–140.2° C.
IR(KBr) ν cm⁻¹: 1607, 1590, 1529, 1506, 1425
NMR (90 MHz, DMSO-d₆ ) δ ppm: 13.26(1H, s), 8.08(1H, s), 8.03(1H, s), 7.38–6.80(7H, m), 6.70–6.36(3H, m), 3.87(2H, t, J=6.6 Hz), 3.36–2.82(4H, m), 2.34–1.20(8H, 0.87(3H, t, J=6.9 Hz), 0.83(3H, t, J=7.3 Hz)

EXAMPLE 150

N-[4-(N,N-diethylamino)-6-mercapto-2-methoxypyrimidin-5-yl]-4-(N-phenyl-N-propylamino)butanamide
Yield: 21%
Melting point: 118.6°–118.9° C.
IR(KBr) ν cm⁻¹: 2958, 1616, 1570, 1506, 1344, 1321, 1038
NMR(270 MHz, DMSO-d₆) δ ppm: 12.69(1H, s), 8.72(1H, s), 7.10(2H, dd, J=8.3 and 7.3 Hz), 6.66(2H, d, J=8.3 Hz), 6.51(1H, t, J=7.3 Hz), 3.87(3H, s), 3.56–3.10(8H, m), 2.45–2.18(2H, m), 1.88–1.72(2H, m), 1.62–1.45(2H, m), 1.17(6H, t, J=6.8 Hz), 0.88(3H, t, J=7.3 Hz)

EXAMPLE 151

N-[4,6-bis(hexylamino)-2-methylpyrimidin-5-yl]-4-(N-phenyl-N-propylamino)butanamide
Yield: 22%
Melting point: 139.6°–140.7° C.
IR(KBr) ν cm⁻¹: 3382, 3226, 2956, 2929, 2858, 1646, 1593, 1507
NMR(90 MHz, DMSO-d₆) δ ppm: 8.36(1H, s), 7.20–6.81(2H, m), 6.81–6.30(3H, m), 5.54(2H, br.s), 3.45–2.61(8H, m), 2.61–2.22(2H, m), 2.19(3H, s), 1.98–1.02(20H, m), 1.02–0.66(9H, m)

EXAMPLE 152

N-[4-(N,N-dimethylamino)-6-hexylaminopyrimidin-5-yl]-4-(N-phenyl-N-propylamino)butanamide
Yield: 7%
Melting point: 81.0°–81.9° C.
IR(KBr) ν cm⁻¹: 3427, 3246, 2958, 2873, 1647, 1593, 1506, 1411
NMR(90 MHz, DMSO-d₆) δ ppm: 8.77(1H, s), 7.92(1H, s), 7.17–6.90(2H, m), 6.72–6.36(3H, m), 6.02(1H, t, J=7.0 Hz), 3.36–3.00(6H, m), 2.93(6H, s), 2.64–2.19(2H, m), 1–95–0.99(12H, m), 0.89(6H, t, J=5.0 Hz)

EXAMPLE 153

N-(4-hydroxy-6-isopropyl-2-methylpyrimidin-5-yl]-4-(N-phenyl-N-propylamino)butanamide
Yield: 40%
Melting point: 201.0°–202.2° C.
IR(KBr) ν cm⁻¹: 3235, 2964, 2931, 1675, 1659, 1606, 1506
NMR(90 MHz, DMSO-d₆) δ ppm: 12.40(1H, s), 8.94(1H, s), 7.26–6.96(2H, m), 6.78–6.36(3H, m), 3.48–2.70(5H, m), 2.46–2.16(2H, m), 2.27(3H, s), 1.98–1.26(4H, m), 1.05(6H, d, J=6.9 Hz), 0.88(3H, t, J=7.3 Hz)

EXAMPLE 154

N-[4-(N,N-diethylamino)-6-mercapto-2-methylpyrimidin-5-yl]-4-(N-methyl-N-phenylamino)butanamide
Yield: 79%
Melting point: 169.6°–171.8° C.
IR(KBr) ν cm⁻¹: 1663, 1605, 1596, 1523, 1508, 1431, 1322
NMR(90 MHz, DMSO-d₆) δ ppm: 12.70(1H, s), 8.76(1H, s), 7.26–7.02(2H, m), 6.78–6.45 (3H, m), 3.63–3.12(6H, m), 2.88(3H, s), 2.43–2.13(2H, m), 2.27 (3H, s), 2.01–1 59(2H, m), 1.08(6H, t, J=6.6 Hz)

EXAMPLE 155

N-[4-(N,N-diethylamino)-6-mercapto-2-methylpyrimidin-5-yl]-4-(N-hexyl-N-phenylamino)butanamide
Yield: 66%
Melting point: 143.3°–145.6° C.
IR(KBr) ν cm⁻¹: 2956, 2929, 1607, 1561, 1508
NMR(90 MHz, DMSO-d₆) δ ppm: 12.71(1H, s), 8.77(1H, s), 7.20–6.96(2H, m), 6.75–6.36(3H, m), 3.63–3.06(8H, m), 2.37–2.10(2H, m), 2.27(3H, s), 1.98–1.62(2H, m), 1.62–1.14(8H, m), 1.08(6H, t, J=6.8 Hz), 0.87 (3H, t, J=5.4 Hz)

EXAMPLE 156

N-[4-(N,N-dipropylamino)-6-mercapto-2-methylpyrimidin-5-yl]-4-(N-hexyl-N-phenylamino)butanamide
Yield: 62%
Melting point: 148.0°–149.3° C.
IR(KBr) ν cm⁻¹: 2960, 2929, 1606, 1564, 1506
NMR(270 MHz, DMSO-d₆) δ ppm: 12.7(1H, s), 8.83(1H, s), 7.10(2H, dd, J=7.9 and 7.3 Hz), 6.67(2H, d, J=7.9 Hz), 6.52(1H, t, J=7.3 Hz), 3.57–3.12(8H, m), 2.45–2.18(2H, m), 2.27(3H, s), 1.89–1.72(2H, m), 1.62–1.38(6H, m), 1.37–1.21(6H, m), 0.86(3H, t, J=6.6 Hz), 0.80(6H, t, J=7.3 Hz)

EXAMPLE 157

N-[4-(N,N-dibutylamino)-6-mercapto-2-methylpyrimidin-5-yl]-4-(N-hexyl-N-phenylamino)butanamide
Yield: 33%
Melting point: 125.6°–128.1° C.
IR(KBr) ν cm⁻¹: 3218, 3178, 1682, 1610, 1567, 1506, 1426, 1326
NMR(90 MHz, DMSO-d₆) δ ppm: 12.73(1H, s), 8.79(1H, s), 7.20–6.96(2H, m), 6.72–6.36(3H, m), 3.60–2.88(8H, m), 2.26(3H, s), 2.40–2.04(2H, m), 1.98–0.96(18H, m), 0.87(9H, t, J=5.9 Hz)

EXAMPLE 158

N-[4-(N-benzyl-N-ethylamino)-6-mercapto -2-methylpyrimidin-5-yl]-4-(N-hexyl-N-phenylamino)-butanamide
Yield: 55%
Melting point: 161.7°–162.0° C.
IR(KBr) ν cm⁻¹: 2929, 1647, 1599, 1564, 1504, 1439, 1429, 1319
NMR(270 MHz, DMSO-d₆) δ ppm: 12.90(1H, s), 8.81(1H, s), 7.36–7.17(5H, m), 7.18(2H, dd, J=8.2 and 7.3 Hz), 6.63(2H, .d, J=8.2 Hz), 6.54(1H, t, J=7.3 Hz), 4.95–4.62(2H, m), 3.48–3.08(4H, m), 2.30–1.92(2H, m), 2.28(3H, s), 1.79–1.63(2H, m), 1.51–1.39(2H, m), 1.34–1.28(6H, m), 1.06(3H, t, j=6.9 Hz), 0.86(3H, t, J=6.6 Hz)

EXAMPLE 159

N-[4-(N-benzyl-N-heptylamino)-6-mercapto-2-methylpyrimidin-5-yl]-4-(N-hexyl-N-phenylamino)butanamide Yield: 70%

Melting point: 119.220 –120.9° C.

IR(KBr) $\nu$ cm$^{-1}$: 3228, 1648, 1600, 1561, 1506

NMR(90 MHz, DMSO-d$_6$) $\delta$ ppm: 12.87(1H, s), 8.79(1H, s), 7.32–6.90(7H, m), 6.72–6.36(3H, m), 4.98–4.56(2H, m), 3.48–2.94(6H, m), 2.34–2.04(2H, m), 2.26(3H, s), 1.92–1.02(20H, m), 0.96–0.66(6H, m)

EXAMPLE 160

N-[4-(N-butylamino)-6-mercapto-2-methylpyrimidin-5-yl]-4-(N-hexyl-N-phenylamino)butanamide Yield: 63%

Melting point: 215.8°–216.7° C.

IR(KBr) $\nu$ cm$^{-1}$: 3315, 2956, 2929, 2861, 1654, 1591, 1506

NMR(90 MHz, DMSO-d$_6$) $\delta$ ppm: 12.62(1H, s), 8.56(1H, s), 7.23–6.96(2H, m), 6.84(1H, t, J=5.4 Hz), 6.72–6.36(3H, m), 3.45–3.03(6H, m), 2.40–2.19(2H, m), 2.29(3H, s), 1.98–1.62(2H, m), 1.62–1.08(12H, m), 0.87(6H, t, J=5.6 Hz)

EXAMPLE 161

4-(N-hexyl-N-phenylamino)-N-(4-mercapto-2-methyl-6-morpholinopyrimidin-5-yl)butanamide Yield: 38%

Melting point: 199.1°–201.0° C.

IR(KBr) $\nu$ cm$^{-1}$: 2956, 2926, 1605, 1567, 1507, 1308

NMR (90 MHz, DMSO-d$_6$) $\delta$ ppm: 12.93(1H, s), 8.76(1H, s), 7.20–6.96(2H, m), 6.72–6.36(3H, m), 3.72–3.42(8H, m), 3.42–3.09(4H, m), 2.40–2.16(2H, m), 2.30(3H, s), 1.95–1.62(2H, m), 1.62–1.08(8H, m), 0.87(3H, t, J=5.8 Hz)

EXAMPLE 162

4-(N-hexyl-N-phenylamino)-N-[4-mercapto-2-methyl-6-(4-methylpiperazinyl)pyrimidin-5-yl]butanamide Yield: 8%

Melting point: 192.7°–194.9° C.

IR (KBr) $\nu$ cm$^{-1}$: 3435, 2929, 1680, 1608, 1570, 1508, 1309

NMR(270 MHz, DMSO-d$_6$) $\delta$ ppm: 12.89(1H, s), 8.79(1H, s), 7.11(2H, dd, J=8.6 and 7.3 Hz), 6.66(2H, d, J=8.6 Hz), 6.52(1H, t, J=7.3 Hz), 3.70–3.55(4H, m), 3.39–3.20(4H, m), 2.39–2.21(9H, m), 2.13(3H, s), 1.86–1.72(2H, m), 1.58–1.41(2H, m), 1.36–1.22(6H, m), 0.92–0.83(3H, m)

EXAMPLE 163

N-[4-(N,N-diethylamino)-6-mercaptopyrimidin-5-yl]-4-(N-hexyl-N-phenylamino)butanamide Yield: 64%

Melting point: 133.3°–135.2° C.

IR(KBr) $\nu$ cm$^{-1}$: 1612, 1595, 1545, 1502, 1470, 1431, 1321

NMR(270 MHz, DMSO-d$_6$) $\delta$ ppm: 12.91(1H, s), 8.89(1H, s), 7.90(1H, s), 7.11(2H, dd, J=8.3 and 7.3 Hz), 6.66(2H, d, J=S.3 Hz), 6.52(1H, t, J=7.3 Hz), 3.47(4H, q, J=6.9 Hz), 3.32–3.20(4H, m), 2.46–2.22(2H, m), 1.88–1.72(2H, m), 1.56–1.38(2H, m), 1.38–1.20 (6H, m), 1.09(6H, t, J=6.9 Hz), 0.87(3H, t, J=6.6 Hz)

EXAMPLE 164

N-[4-(N,N-diethylamino)-6-mercapto-2-methoxypyrimidin-5-yl]-4-(N-hexyl-N-phenylamino)butanamide Yield: 47%

Melting point: 95.9°–97.2° C.

IR(KBr) $\nu$ cm$^{-1}$: 2926, 1682, 1610, 1572, 1508, 1348, 1317, 1038

NMR(270 MHz, DMSO-d$_6$) $\delta$ ppm: 12.67(1H, s), 8.70(1H, s), 7.10(2H, dd, J=8.6 and 7.3 Hz), 6.65(2H, d, J=8.6 Hz), 6.51(1H, t, J=7.3 Hz), 3.87(3H, s), 3.60–3.18(8H, m), 2.40–2.20(2H, m), 1.86–1.72(2H, m), 1.56–1.42(2H, m), 1.34–1.20(6H, m), 1.12(6H, t, J=6.9 Hz), 0.87(3H, t, J=6.6 Hz)

EXAMPLE 165

N-[4-(N,N-diethylamino)-6-mercapto-2-methylthiopyrimidin -5-yl]-4-(N-hexyl-N-phenylamino)butanamide Yield: 49%

Melting point: 137.3°–138.3° C.

IR(KBr) $\nu$ cm$^{-1}$: 2924, 1682, 1552, 1504, 1427, 1321, 1269

NMR(270 MHz, DMSO-d$_6$) $\delta$ ppm: 13.10(1H, s), 8.82(1H, s), 7.11(2H, dd, J=8.6 and 7.3 Hz), 6.66(2H, d, J=S.6 Hz), 6.52(1H, t, J=7.3 Hz), 3.62–3.13(8H, m), 2.48(3H, s), 2.43–2.17(2H, m), 1.88–1.70(2H, m), 1.57–1.37(2H, m), 1.35–1.18(6H, m), 1.11(6H, t, J=6.9 Hz), 0.87(3H, t, J=6.4 Hz)

EXAMPLE 166

N-[4-(N,N-diethylamino)-6-methoxy-2-methylpyrimidin-5-yl]-4-(N-hexyl-N-phenylamino)butanamide Yield: 39%

Melting point: 74.0°–74.8° C.

IR(KBr) $\nu$ cm$^{-1}$: 2854, 1654, 1568, 1561, 1506, 1374

NMR(90 MHz, DMSO-d$_6$) $\delta$ ppm: 8.88(1H, s), 7.32–6.96(2H, m), 6.84–6.36(3H, m), 3.73(3H, s), 3.60–2.94(8H, m), 2.32(3H, s), 2.40–2.10(2H, 1.98–1.14(10H, m), 1.08(6H, t, J=6.8 Hz), 0 87(3H, t, J=5.6 Hz)

EXAMPLE 167

N-[4-(N,N-dipropylamino)-6-methoxy-2-methylpyrimidin-5-yl]-4-(N-hexyl-N-phenylamino)butanamide Yield: 25%

Melting point: 79.8°–81.2° C.

IR(KBr) $\nu$ cm$^{-1}$: 1651, 1583, 1564, 1506, 1427, 1375, 1109

NMR(270 MHz, DMSO-d$_6$) $\delta$ ppm: 8.91(1H, s), 7.11(2H, dd, J=8.3 and 7.3 Hz), 6.65(2H, d, J=8.3 Hz), 6.53(1H, t, J=7.3 Hz), 3.73(3H, s), 3.42–3.20(8H, m), 2.34–2.18(2H, m), 2.30(3H, s), 1.86–1.68(2H, m), 1.60–1.38(6H, m), 1.38–1.16(4H, m), 0.83(3H, t, J=7.3 Hz), 0.80(6H, t, J=7.3 Hz)

EXAMPLE 168

N-[4-(N,N-diethylamino)-6-methoxy-2-methylthiopyrimidin-5-yl]-4-(N-hexyl-N-phenylamino)butanamide Yield: 40%

Melting point: 73.6°–74.7° C.

IR(KBr) $\nu$ cm$^{-1}$: 2926, 1653, 1552, 1504, 1377, 1321, 1097

NMR(270 MHz, DMSO-d$_6$) $\delta$ ppm: 8.93(1H, s), 7.12(2H, dd, J=8.3 and 7.3 Hz), 6.66(2H, d, J=8.3 Hz), 6.53(1H, t, J=7.3 Hz), 3.73(3H, s), 3.60–3.13(8H, m), 2.43(3H, s), 2.38–2.17(2H, m), 1.87–1.67(2H, m), 1.58–1.40(2H, m), 1.40–1.16(6H, m), 1.09(6H, t, J=6.9 Hz), 0.87(3H, t, J=6.6 Hz)

EXAMPLE 169

N-(4,6-dimethoxy-2-methylpyrimidin-5-yl)-4-(N-hexyl-N-phenylamino)butanamide
Yield: 73%
Melting point: 85.5°–87.1° C.
IR(KBr) $\nu$ cm$^{-1}$: 3236, 1659, 1579, 1533, 1506, 1362, 1134
NMR(270 MHz, DMSO-d$_6$) $\delta$ ppm: 9.04(1H, s), 7.12(2H, dd, J=7.9 and 7.3 Hz), 6.65(2H, d, J=7.9 Hz), 6.53(1H, t, J=7.3 Hz), 3.86(6H, s), 3.44–3.12(4H, m), 2.47(3H, s), 2.36–2.20(2H, m), 1.86–1.67(2H, m), 1.58–1.41(2H, m), 1.37–1.18(6H, m), 0.86(3H, t, J=6.4 Hz)

EXAMPLE 170

4-(N-cycloheptyl-N-phenylamino)-N-[4-(N,N-diethylamino)-6-mercapto-2-methylpyrimidin-5-yl]butanamide
Yield: 48%
Melting point: 195.0°–199.0° C.
IR(KBr) $\nu$ cm$^{-1}$: 2929, 1608, 1564, 1504, 1429, 1319
NMR(270 MHz, DMSO-d$_6$ ) $\delta$ ppm: 12.74(1H, s), 8.83(1H, s), 7.12(2H, dd, J=8.3 and 7.3 Hz), 6.73(2H, d, J=8.3 Hz), 6.55(1H, t, J=7.3 Hz), 3.75–3.62(1H, m), q, 3.45(4n, J=6.9 Hz), 3.33–3.15(2H, m), 2.42–2.20 (2H, m), 2.28(3H, s),1.86–1.38(14H, m), 1.08(6H, t, J=6.9 Hz)

EXAMPLE 171

4-(N-decyl-N-phenylamino)-N-[4-(N,N-diethylamino)-6-mercapto-2-methylpyrimidin-5-yl]butanamide
Yield: 56%
Melting point: 131.3°–134.2° C.
IR (KBr) $\nu$ cm$^{-1}$: 2925, 2854, 1678, 1609, 1565, 1507
NMR(90 MHz, DMSO-d$_6$ ) $\delta$ ppm: 12.73(1H, s), 8.80(1H, s), 7.20–6.96(2H, m), 6.72–6.39(3H, m), 3.63–3.09(8H, m), 2.28(3H, s), 2.01–1.65(2H, m),1.65–1.20(18H, m), 1.08(6H, t, J=6.9 Hz), 0.85(3H, t, J=5.8 Hz)

EXAMPLE 172

4-[N-(4-butylphenyl)-N-propylamino]-N-[4-(N,N-diethylamino)-6-mercapto-2-methylpyrimidin-5-yl]butanamide
Yield: 48%
Melting point: 145.7°–147.5° C.
IR (KBr) $\nu$ cm$^{-1}$: 3172, 1610, 1564, 1430, 1320
NMR(90 MHz, DMSO-d$_6$) $\delta$ ppm: 12.71(1H, s), 8.76(1H, s), 6.93(2H, d, J=8.4 Hz), 6.58(2H, d, J=8.4 Hz), 3.66–2.82(8H, m), 2.46–2.04(4H, m), 2.27(3H, s), 2.04–1.20(8H, m), 1.08(6H, t, J=6.9 Hz), 0.87(6H, t, J=6.9 Hz)

EXAMPLE 173

N-[4-(N,N-diethylamino)-6-mercapto-2-methyl-pyrimidin-5-yl]-4-[N-(4-methoxyphenyl)-N-propylamino]butanamide
Yield: 75%
Melting point: 142.2°–144.6° C.
IR(KBr) $\nu$ cm$^{-1}$: 2963, 2958, 1610, 1564, 1513, 1430, 1321, 1240
NMR(90 MHz, DMSO-d$_6$) $\delta$ ppm: 12.71(1H, s), 8.74(1H, s), 6.84–6.48(4H, m), 3.64(3H, s), 3.60–2.94(8H, m), 2.40–2.10(2H, m), 2.27(3H, s), 1.98–1.26(4H, m), 1.07(6H, t, J=6.8 Hz), 0.86(3H, t, J=7.1 Hz)

EXAMPLE 174

N-[4-(N,N-diethylamino)-6-mercapto-2-methoxypyrimidin-5-yl]-4-[N-(4-methoxyphenyl)-N-propylamino]butanamide
Yield: 25%
Melting point: 156.2°–158.4° C.
IR(KBr) $\nu$ cm$^{-1}$: 2958, 1682, 1622, 1570, 1516, 1342, 1321, 1034
NMR(270 MHz, DMSO-d$_6$) $\delta$ ppm: 12.68(1H, s), 8.70(1H, s), 6.76(2H, d, J=9.2 Hz), 6.65(2H, d, J=9.2 Hz), 3.87(3H, s), 3.64(3H, s), 3.58–3.35(4H, m), 3.33–3.05(4H, m), 2.43–2.15(2H, m), 1.85–1.70(2H, m), 1.58–1.40(2H, m), 1.11(6H, t, J=6.8 Hz), 0.86(3H, t, J=7.3 Hz)

EXAMPLE 175

N-[4-(N,N-diethylamino)-2-6-dimethoxypyrimidin-5-yl]4-N-(4-methoxyphenyl)-N-propylamino ]butanamide
Yield: 33%
IR(neat) $\nu$ cm$^{-1}$: 3259, 2956, 1593, 1514, 1464, 1375, 1240, 1105
NMR(270 MHz, DMSO-d$_6$) $\delta$ ppm: 8.80(1H, s), 6.77(2H, d, J=9.2 Hz), 6.65(2H, d, J=9.2 Hz),3.78(3H, s), 3.71(3H, s), 3.54–3.36(4H, m), 3.26–3.10(4H, m), 2.37–2.12(2H, m), 1.82–1.65(2H, m), 1.57–1.38(2H, m), 1.09(6H, t, J=6.9 Hz), 0.86(3H, t, J=7.4 Hz)

EXAMPLE 176

N-[4-(N,N-diethylamino)-6-mercapto-2-methyl-pyrimidin-5-yl]-4-[N-(3-methoxyphenyl)-N-propylamino]butanamide
Yield: 41%
Melting point: 136.9°–139.3° C.
IR(KBr) $\nu$ cm$^{-1}$: 2960, 2935, 1610, 1566, 1500, 1429, 1321
NMR(270 MHz, DMSO-d$_6$) $\delta$ ppm: 12.74(1H, s), 8.82(1H, s), 7.01(1H, t, J=8.3 Hz), 6.27(1H, d, J=8.3 Hz), 6.17(1H, s), 6.13(-1H, d, J=8.3 Hz), 3.68(3H, s), 3.45(4H, q, J=6.9 Hz), 3.39–3.12(4H, m), 2.40–2.19(2H, m), 2.28(3H, s), 1.87–1.72(2H, m), 1.60–1.43(2H, m), 1.08(6H, t, J=6.9 Hz), 0.87(3H, t, J=7.3 Hz)

EXAMPLE 177

N-[4-(N,N-diethylamino)-6-mercapto-2-methyl-pyrimidin-5-yl]-4-[N-(1,3-benzodioxol-5-yl)-N-propylamino]butanamide
Yield: 76%
Melting point: 172.6°–173.1° C.
IR(KBr) $\nu$ cm$^{-1}$: 2958, 1682, 1610, 1564, 1504, 1429, 1321, 1221
NMR(270 MHz, DMSO-d$_6$) $\delta$ ppm: 12.74(1H, s), 8.81(1H, s), 6.69(1H, d, J=8.4 Hz), 6.42(1H, d, J=2.3 Hz), 6.08(1H, dd, J=8.4 and 2.3 Hz), 5.82(2H, s), 3.45(4H, q, J=7.1 Hz), 3.39–3.00(2H, m), 2.43–2.18(2H, m), 2.27(3H, s), 1.86–1.66(2H, m), 1.58–1.42(2H, m), 1.08(6H, t, J=7.1 Hz), 0.86(3H, t, J=7.3 Hz)

EXAMPLE 178

N-[4-(N,N-diethylamino)-6-mercapto-2-methyl-pyrimidin-5-yl]-4-[N-hexyl-N-(4-methoxyphenyl)amino]butanamide
Yield: 61%
Melting point: 131.1°–135.2° C.
IR (KBr) $\nu$ cm$^{-1}$: 2931, 2868, 1566, 1516, 1431, 1319, 1244

NMR(90 MHz, DMSO-d$_6$) δ ppm: 12.72(1H, s), 8.75(1H, s), 6.84–6.48(4H, m), 3.64(3H, s), 3.60–2.94(8H, m), 2.40–2.13(2H, m), 2.27(3H, s), 1.95–1.59(2H, m), 1.59–1.14(8H, m), 1.07(6H, t, J=6.6 Hz), 0.85(3H, t, J=5.4 Hz)

EXAMPLE 179

N-[4-(N,N-diethylamino)-6-mercapto-2-methylpyrimidin-5-yl]-4-[N-hexyl-N-(2-methoxyphenyl)amino]butanamide
Yield: 35%
Melting point: 69.6°–72.0° C.
IR(KBr) ν cm$^{-1}$: 2929, 1610, 1564, 1500, 1429, 1319, 1236
NMR(270 MHz, DMSO-d$_6$) δ ppm: 12.70(1H, s), 8.69(1H, s), 6.95–6.77(4H, m), 3.76(3H, s), 3.42(4H, q, J=6.7 Hz), 3.14–2.97 (4H, m), 2.32–2.17 (2H, m), 2.26(3H, s), 1.75–1.57(2H, m), 1.43–1.30(2H, m), 1.30–1.12(6H, m), 1.05(6H, t, J=6.8 Hz), 0.83(3H, t, J=6.4 Hz)

EXAMPLE 180

N-[4-(N,N-diethylamino)-6-mercapto-2-methylpyrimidin-5-yl]-4-[N-(2,4-difluorophenyl)-N-propylamino]butanamide
Yield: 38%
Melting point: 133.6°–135.5° C.
IR(KBr) ν cm$^{-1}$: 2966, 1610, 1565, 1561, 1508, 1430, 1322
NMR(90 MHz, DMSO-d$_6$) δ ppm: 12.69(1H, s), 8.70(1H, s), 7.26–6.75(3H, m), 3.43(4H, q, J=6.8 Hz), 3.24–2.82(4H, m), 2.40–2.10(2H, m), 2.27 (3H, s), 1.86–1.23(4H, m), 1.06(6H, t, J=6.8 Hz), 0.82(3H, t, J=7.1 Hz)

EXAMPLE 181

4-(N-benzyl-N-propylamino)-N-[4-(N,N-diethylamino)-6-mercapto-2-methylpyrimidin-5-yl]butanamide
Yield: 47%
Melting point: 117.8°–119.3° C.
IR(KBr) ν cm$^{-1}$: 3227, 2956, 1685, 1611, 1561, 1509, 1320
NMR(90 MHz, DMSO-d$_6$) δ ppm: 12.68(1H, s), 8.65(1H, s), 7.43–7.13(5H, m), 3.54–3.18(4H, m), 3.53(2H, s), 2.40–2.10(6H, m), 2.26(3H, s), 1.92–1.26(4H, m), 1.06(6H, t, J=6.8 Hz), 0.80(3H, t, J=7.1 Hz)

EXAMPLE 182

4-(N-benzyl-N-heptylamino)-N-[4-(N,N-diethylamino)-6-mercapto-2-methylpyrimidin-5-yl]butanamide
Yield: 77%
Melting point: 93.6°–96.9° C.
IR(KBr) ν cm$^{-1}$: 2954, 2928, 1611, 1567, 1514, 1498, 1319
NMR(90 MHz, DMSO-d$_6$) δ ppm: 12.70(1H, s), 8.66(1H, s), 7.38–7.14(5H, m), 3.63–3.24(4H, m), 3.52(2H, s), 2.52–2.04(6H, m), 2.27(3H, s), 1.90–1.08(14H, m), 1.07(6H, t, J=6.9 Hz), 0.89(3H, t, J=4.9 Hz)

EXAMPLE 183

N-[4-(N,N-diethylamino)-6-mercapto-2-methylpyrimidin-5-yl]-4-(tetrahydroquinolino)butanamide
Yield: 14%
Melting point: 202.6°–203.4° C.
IR(KBr) ν cm$^{-1}$: 3256, 1655, 1603, 1569, 1508

NMR(90 MHz, DMSO-d$_6$) δ ppm: 12.71(1H, s), 8.78(1H, s), 7.02–6.72(2H, m), 6.66–6.30(2H, m), 3.60–3.06(8H, m), 2.66(2H, t, J=5.9 Hz), 2.34–2.10(2H, m), 2.27(3H, s), 1.98–1.56(4H, m),.1.08(6H, t, J=6.6 Hz)

EXAMPLE 184

N-[4-(N,N-diethylamino)-6-mercapto-2-methylpyrimidin-5-yl]-4-(4-phenylpiperazinyl)butanamide
Yield: 5%
Melting point: 199.0°–201.7° C.
IR(KBr) ν cm$^{-1}$: 2969, 1683, 1602, 1565, 1497, 1320
NMR (90 MHz, CDCl$_3$) δ ppm: 8.0 2(1H, s), 7.38–7.11(2H, m), 6.99–6.72(3H, m), 3.75–3.30(4H, m), 3.30–3.06(4H, m), 2.76–2.40(8H, m), 2.35(3H, s), 2.16–1.62(2H, m), 1.16(6H, t, J=6.9 Hz)

EXAMPLE 185

N-[4-mercapto-2-methyl-6-(N-phenyl-N-propylamino)pyrimidin-5-yl]-5-(N-phenyl-N-propylamino)pentanamide
Yield: 31%
Melting point: 122.1°–123.6° C.
IR (KBr) ν cm$^{-1}$: 2959, 1594, 1560, 1505, 1422
NMR(90 MHz, DMSO-d$_6$) δ ppm: 13.07(1H, s), 7.79(1H, s), 7.38–6.81(7H, m), 6.66–6.39(3H, m), 4.00–3.70(2H, m), 3.30–3.00(4H, m), 2.64–2.28(2H, m), 2.36(3H, s), 1.74–1.14(8H, m), 0.87(3H, t, J=7.1 Hz), 0.84(3H, t, J=6.9 Hz)

EXAMPLE 186

N-[4-(N,N-dimethylamino)-6-mercapto-2-methylpyrimidin-5-yl]-5-(N-phenyl-N-propylamino)pentanamide
Yield: 31%
Melting point: 180.2°–181.0° C.
IR(KBr) ν cm$^{-1}$: 1678, 1606, 1570, 1504, 1398, 1313
NMR(270 MHz, DMSO-d$_6$) δ ppm: 12.76(1H, s), 8.69(1H, s), 7.11(2H, dd, J=8.3 and 7.3 Hz), 6.61(2H, d, J=8.3 Hz), 6.52(1H, t, J=7.3 Hz), 3.33–3.12(4H, m), 3.01(6H, m), 2.38–2.20(2H, m), 2.28(3H, s), 1.68–1.38(6H, m), 0.88(3H, t, J=6.8 Hz)

EXAMPLE 187

N-[4-(N,N-diethylamino)-6-mercapto-2-methylpyrimidin-5-yl]-5-(N-phenyl-N-propylamino)pentanamide
Yield: 55%
Melting point: 138.7°–140.4° C.
IR(KBr) ν cm$^{-1}$: 1607, 1561, 1507, 1431, 1320
NMR(90 MHz, DMSO-d$_6$) δ ppm: 12.70(1H, s), .8.68(1H, 7.26–6.96(2H, m), 6.72–6.66(3H, m), 3.60–3.03(8H, 2.46–2.10(2H, m), 2.27(3H, s), 1.92–1.26(6H, m), 1.06(6H, t, J=6.9 Hz), 0.88(3H, t, J=7.4 Hz)

EXAMPLE 188

N-[4-(N,N-dipropylamino)-6-mercapto-2-methylpyrimidin-5-yl]-5-(N-phenyl-N-propylamino)pentanamide
Yield: 61%
Melting point: 145.9°–146.9° C.
IR(KBr) ν cm$^{-1}$: 2958, 2931, 2872, 1674, 1608, 1566, 1506, 1425
NMR(270 MHz, DMSO-d$_6$) δ ppm: 12.7(1H, s), 8.72(1H, s), 7.11 (2H, dd, J=8.2 and 7.3 Hz), 6.61(2H, d, J=8.2 Hz), 6.52(1H, t, J=7.3 Hz), 3.62–3.08(8H, m), 2.42–2.18(2H, m), 2.26(3H, s), 1.72–1.32(10H, m), 0.88(3H, t, J=7.4 Hz), 0.80(6H, t, J=7.3 Hz)

EXAMPLE 189

N-[4-(N,N-dibutylamino)-6-mercapto-2-methyl-pyrimidin-5-yl]-5-(N-phenyl-N-propylamino)pentanamide Yield: 43%

Melting point: 140.3°–143.0° C.

IR(KBr) ν cm$^{-1}$: 2956, 2870, 1678, 1610, 1566, 1510

NMR(90 MHz, DMSO-d$_6$) δ ppm: 12.70(1H., s), 8.69(1H, s), 7.20–6.90(2H, m), 6.72–6.36(3H, m), 3.72–2.76(8H, m), 2.40–2.04(2H, m), 2.25(3H, s), 1.80–1.02(14H, m), 0.86(9H, t, J=6.3 Hz)

EXAMPLE 190

N-[4-(N-benzyl-N-ethylamino)-6-mercapto-2-methyl-pyrimidin-5-yl]-5-(N-phenyl-N propylamino)pentanamide Yield: 39%

Melting point: 55.9°–57.1° C.

IR(KBr) ν cm$^{-1}$: 2956, 1662, 1605, 1564, 1506, 1431, 1319, 1296

NMR(270 MHz, DMSO-d$_6$) δ ppm: 12.89(1H, s), 8.71(1H, s), 7.32–7.18(5H, m), 7.10(2H, dd, J=8.6 and 7.3Hz), 6.59(2H, d, J=8.6 Hz), 6.51(1H, t, J=7.3 Hz), 4.99–4.59(2H, m), 3.50–3.29(2H, m), 3.26–3.09(4H , m), 2.32–1.98(2H, m), 2.27(3H, s), 1.60–1.40(6H, m), 1.03(3H, t, J=6.9 Hz), 0.86(3H, t, J=7.4 Hz)

EXAMPLE 191

N-[4-(N-benzyl-N-heptylamino)-6-mercapto-2-methylpyrimidin-5-yl]-5-(N-phenyl-N-propylamino)-pentanamide Yield: 55%

Melting point: 90.4°–92.6° C.

IR(KBr) ν cm$^{-1}$: 2954, 2929, 2854, 1601, 1561, 1506

NMR(90 MHz, DMSO-d$_6$) δ ppm: 12.86(1H, s), 8.70(1H, 7.32–6.93(7H, m), 6.66–6.36(3H, m), 4.98–4.56(2H, m), 3.42–2.97(6H, m), 2.31–2.04(2H, m), 2.26(3H, s), 1.80–0.96(16H, m), 0.96–0.66(6H, m)

EXAMPLE 192

N-[4-(N,N-dibutylamino)-6-mercaptopyrimidin-5-yl]-5-(N-phenyl-N-propylamino)pentanamide Yield: 59%

Melting point: 107.4°–108.0° C.

IR(KBr) ν cm$^{-1}$: 2954, 2931, 1668, 1608, 1537, 1504, 1425, 1375

NMR(270 MHz, DMSO-d$_6$) δ ppm: 12.90(1H, s), 8.82(1H, s), 7.89(1H, s), 7.11(2H, dd, J=8.2 and 7.3 Hz), 6.61(2H, d, J=8.2 Hz), 6.52(1H, t, J=7.3 Hz), 3.60–3.44(2H, m), 3.36–3.15(6H, m), 2.42–2.20(2H, m), 1.69–1.38(10H, m), 1.30–1.12(4H, m), 0.88(3H, t, J=7.3 Hz), 0.86(6H, t, J=7.3 Hz)

EXAMPLE 193

N-[4-(N,N-dibutylamino)-2-(N,N-dimethylamino)-6-mercaptopyrimidin-5-yl]-5-(N-phenyl-N-propylamino)-pentanamide Yield: 30%

Melting point:94.6°–100.0° C.

IR(KBr) ν cm$^{-1}$: 2956, 2933, 1610, 1552, 1506, 1371

NMR(2,70 MHz, DMSO-d$_6$) δ ppm: 10.77(1H, s), 8.50(1H, s), 7.11(2H, dd, J=8.2 and 7.3 Hz), 6.61(2H, d, J=8.2 Hz), 6.52(1H, t, J=7.3 Hz), 3.54–3.12(8H, m), 3.05(6H, s), 2.43–2.12(2H, m), 1.70–1.33(10H, m), 1.26–1.18(4H, m), 0.88(3H, t, J=7.3 Hz), 0.86(6H, t, J=7.3 Hz)

EXAMPLE 194

N-[4-(N,N-dipropylamino)-6-methoxy-2-methyl-pyrimidin-5-yl]-5-(N-phenyl-N-propylamino)pentanamide Yield: 48%

Melting point: 98.1°–98.8° C.

IR(KBr) ν cm$^{-1}$: 1649, 1578, 1564, 1504, 1423, 1371, 1109

NMR(270 MHz, DMSO-d$_6$) δ ppm: 8.83(1H,.s), 7.11(2H, dd, J=8.2 and 7.3 Hz), 6.62(2H, d, J=8.2 Hz), 6.52(1H, t, J=7.3 Hz), 3.67(3H, s), 3.40–3.10 (8H, m), 2.36–2.16(2H, m), 2.29(3H, s), 1.68–1.38(10H, m), 0.88(3H, t, J=7.3 Hz), 0.79(6H, t, J=7.3 Hz)

EXAMPLE 195

N-[4-(N,N-dibutylamino)-6-methoxy-2-methyl-pyrimidin-5-yl]-5-(N-phenyl-N-propylamino)pentanamide Yield: 50%

Melting point: 83.6°–85.3° C.

IR (KBr) ν cm$^{-1}$: 3296, 2956, 1651, 1576, 1504, 1109, 746, 694

NMR(270 MHz, DMSO-d$_6$) δ ppm: 8.82(1H, s), 7.12(2H, dd, J=8.2 and 7.3 Hz), 6.62(2H, d, J=8.2 Hz), 6.55 (1H, t, J=7.3 Hz), 3.67(3H, s), 3.42–3.14(8H, m), 2.30–2.20(2H, m), 2.29(3H, s), 2.30–2.20(2H, m), 1.65–1.3.8(10H, m), 1.30–1.13(4H, m), 0.88(3H, t, J=7.3 Hz), 0.87(6H, t, J=7.3 Hz)

EXAMPLE 196

N-[4-(N,N-dibutylamino)-6-ethoxy-2-methylpyrimidin-5-yl]-5-(N-phenyl-N-propylamino)pentanamide Yield: 71%

Melting point: 87.9°–89.2° C.

IR(KBr) ν cm$^{-1}$: 3305, 2956, 2872, 1653, 1578, 1506, 1375, 1111

NMR(270 MHz, DMSO-d$_6$) δ ppm: 8.81(1H, s), 7.11(2H, dd, J=7.9 and 7.3 Hz), 6.61(2H, d, J=7.9 Hz), 6.52(1H, t, J=7.3 Hz), 4.15 (2H, q, J=7.0 Hz), 3.42–3.10(8H, m), 2.34–2.14(2H, m), 2.27(3H, s), 1.67–1.32(10H, m), 1.30–1.08(4H, m), 1.15 (3H, t, J=7.0 Hz), 0.88(3H, t, J=7.4 Hz), 0.87(6H, t, J=7.3 Hz)

EXAMPLE 197

N-[4-(N,N-dibutylamino)-6-ethoxypyrimidin-5-yl]-5-(N-phenyl-N-propylamino)pentanamide Yield: 23%

Melting point: 80.8°–83.3° C.

IR(KBr) ν cm$^{-1}$: 2956, 1655, 1585, 1508, 1431, 1377, 1099

NMR(270 MHz, DMSO-d$_6$) δ ppm: 8.92(1H, s), 8.08(1H, s), 7.11(2H, dd, J=8.2 and 7.3 Hz), 6.62(2H, d, J=8.2 Hz), 6.52 (1H, t, J=7.3 Hz), 4.18(2H, q, J=7.0 Hz), 3.42–3.16(8H, m), 2.30–2.20(2H, m), 1.63–1.40(10H, m), 1.30–1.12(4H, m), 1.16(3H, t, J=7.0 Hz), 0.88(3H, t, J=7.4 Hz), 0.87(6H, t, J=7.3 Hz)

EXAMPLE 198

N-(4,6-dimethoxy-2-methylpyrimidin-5-yl)-5-(N-phenyl-N-propylamino)pentanamide

Yield: 31%

Melting point: 126.6°–129.2° C.

IR(KBr) ν cm$^{-1}$: 3263, 1660, 1579, 1522, 1506, 1360, 1134

NMR(270 MHz, DMSO-d$_6$) δ ppm: 8.98(1H, s), 7.11(2H, dd, J=7.9 and 7.3 Hz), 6.62(2H, d, J=7.9Hz), 6.52 (1H, t, J=7.3 Hz), 3.81(6H, s), 3.33–3.16(4H, m), 2.45(3H, s), 2.34–2.22(2H, m), 1.66–1.44(6H, m), 0.88(3H, t, J=7.3 Hz)

EXAMPLE 199

N-[4-(N,N-diethylamino)-6-mercapto-2-methyl-pyrimidin-5-yl]-5-(N-hexyl-N-phenylamino)pentanamide Yield: 40%

Melting point: 93.0°–97.0° C.

IR(KBr) ν cm$^{-1}$: 2931, 2867, 1609, 1561, 1506

NMR(90 MHz, DMSO-d$_6$) δ ppm: 12.70(1H, s), 8.67(1H, s), 7.20–6.96(2H, m), 6.66–6.36(3H, m), 3.48(4H, q, J=6.8 Hz), 3.36–3.06(4H, m), 2.40–2.13(2H, m), 2.27(3H, s), 1.80–1.14(12H, m), 1 06(6H, t, J=6.9 Hz), 0.86(3H, t, J=5.6 Hz)

EXAMPLE 200

5-(N-cyclohexyl-N-propylamino)-N-[4-(N,N-dibutylamino)-6-mercapto-2-methylpyrimidin-5-yl]butanamide Yield: 32%

IR(KBr) ν cm$^{-1}$: 2933, 2860, 1606, 1560, 1520, 1456, 1427

NMR(270 MHz, DMSO-d$_6$).δ ppm: 12.76(1H, s), 8.87(1H, s), 3.62–2.80(9H, m), 2.42–2.14(2H, m), 2.26(3H, s), 2.10–1.02(24H, m), 0.88(9H, t, J=6.6 Hz)

The structures of the compounds of examples 132–200 are shown in the following.

Example No.

132 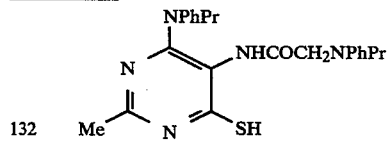

133 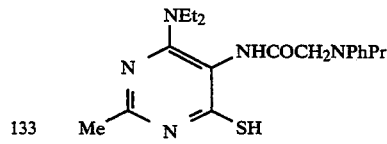

134 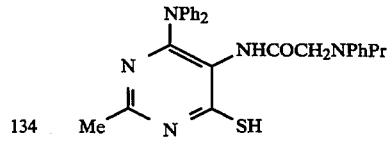

135 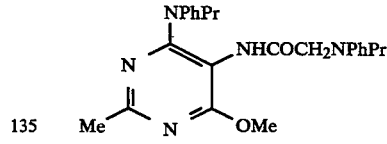

136 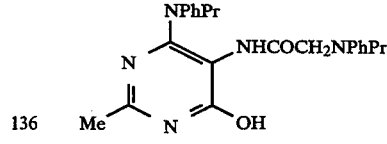

137 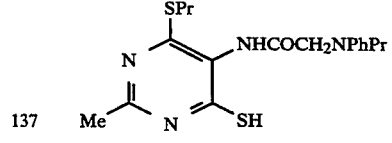

Example No. -continued

138 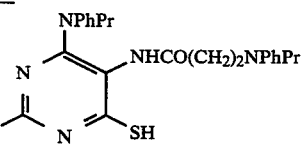

139 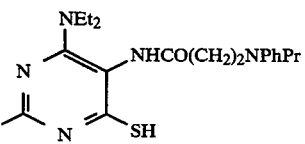

140 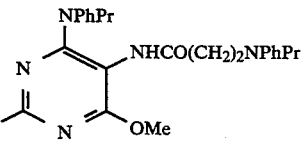

141 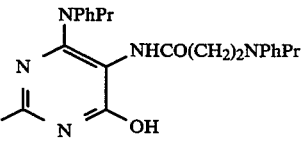

142 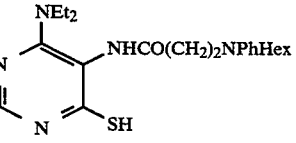

143 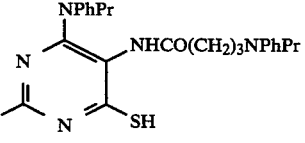

144 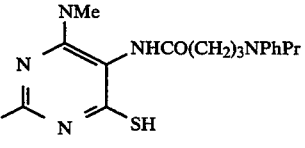

145 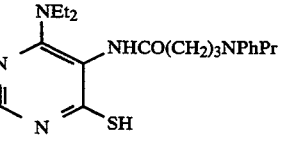

146 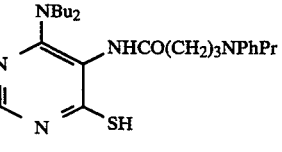

147 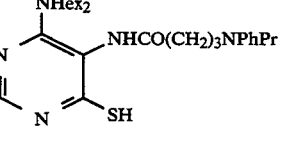

148 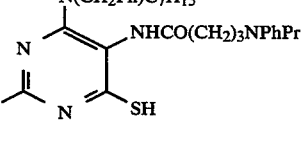

-continued
Example No.
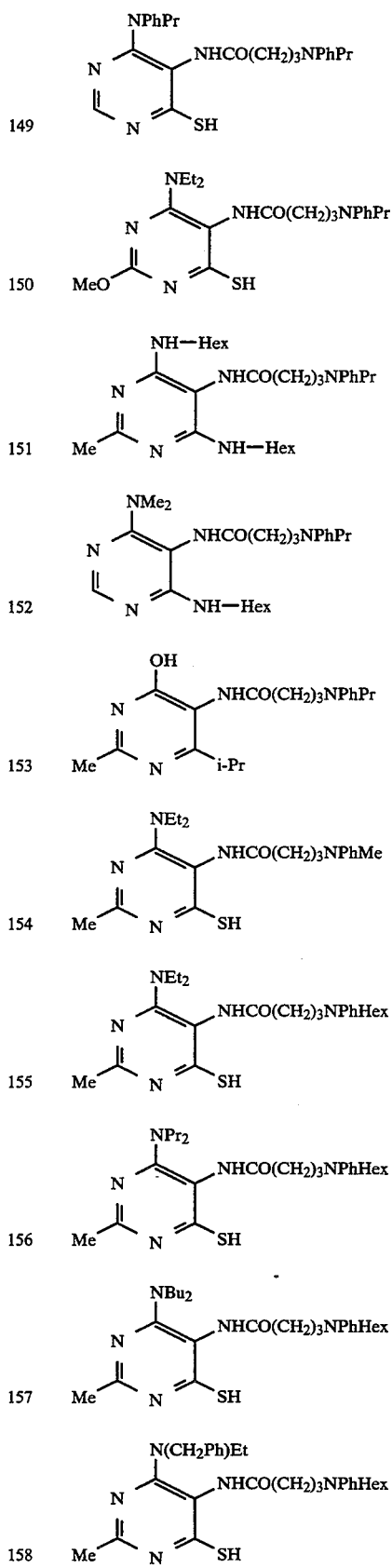
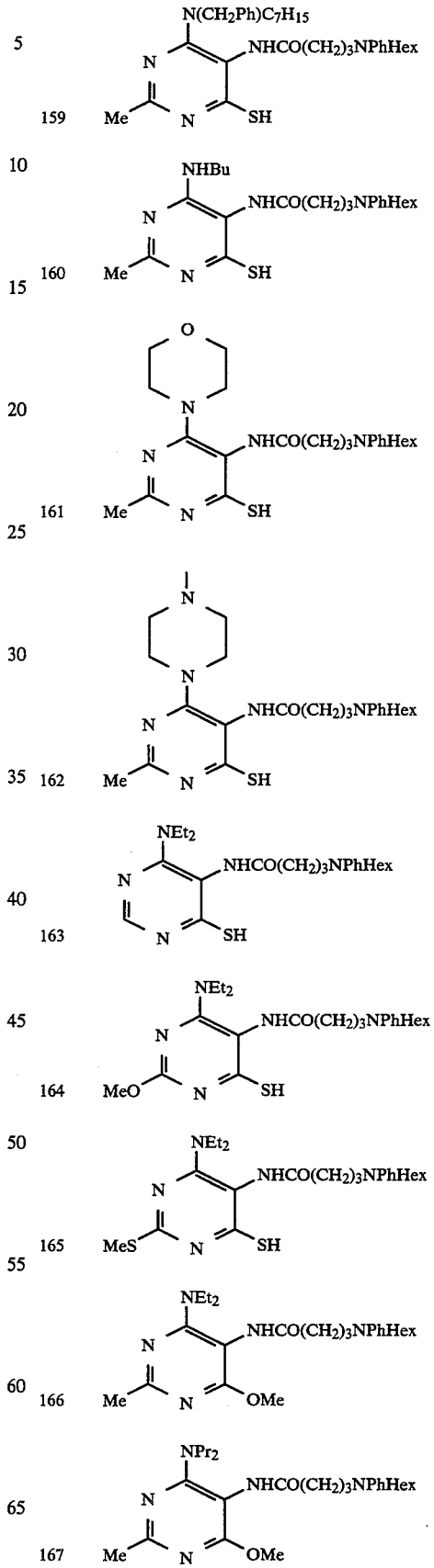

| Example No. | |
|---|---|
| 168 | 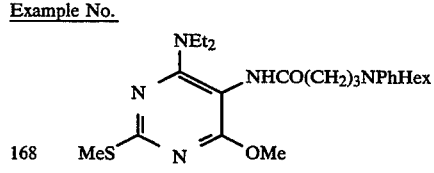 |
| 169 | 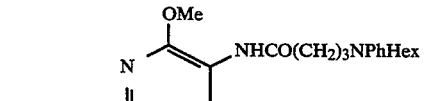 |
| 170 | 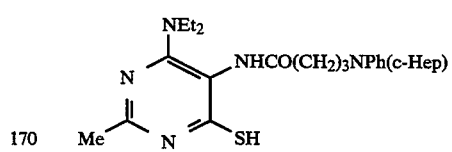 |
| 171 | 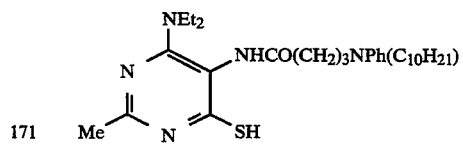 |
| 172 | 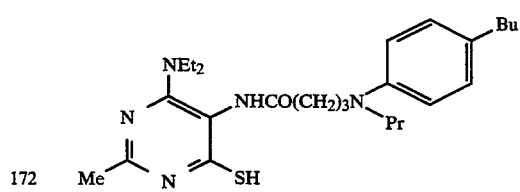 |
| 173 | 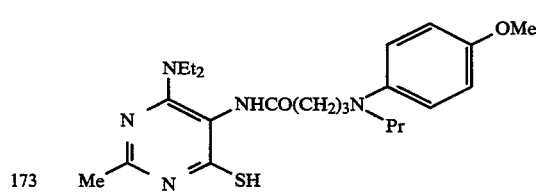 |
| 174 | 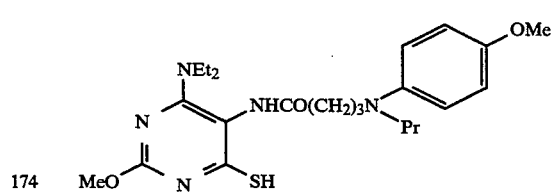 |
| 175 | 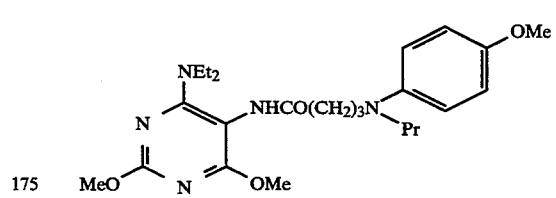 |
| 176 | 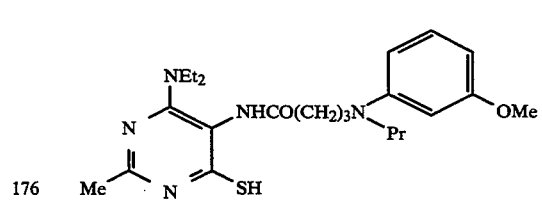 |
| Example No. | |
|---|---|
| 177 | 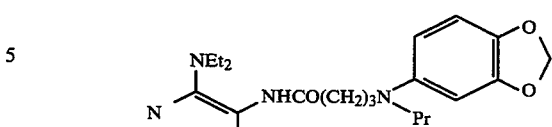 |
| 178 | 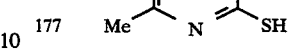 |
| 179 |  |
| 180 | 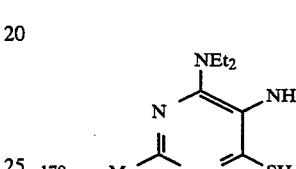 |
| 181 | 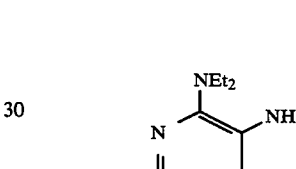 |
| 182 | 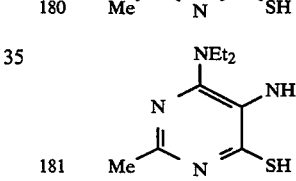 |
| 183 | 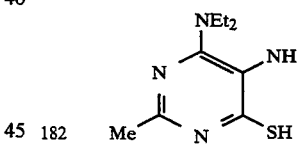 |
| 184 | 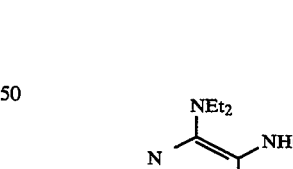 |
| 185 | 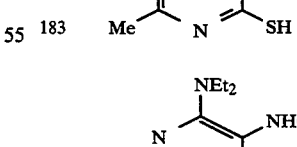 |

-continued

| Example No. | Structure |
|---|---|
| 186 | 4-NMe₂, 5-NHCO(CH₂)₄NPhPr, 6-SH, 2-Me pyrimidine |
| 187 | 4-NEt₂, 5-NHCO(CH₂)₄NPhPr, 6-SH, 2-Me pyrimidine |
| 188 | 4-NPr₂, 5-NHCO(CH₂)₄NPhPr, 6-SH, 2-Me pyrimidine |
| 189 | 4-NBu₂, 5-NHCO(CH₂)₄NPhPr, 6-SH, 2-Me pyrimidine |
| 190 | 4-N(CH₂Ph)Et, 5-NHCO(CH₂)₄NPhPr, 6-SH, 2-Me pyrimidine |
| 191 | 4-N(CH₂Ph)C₇H₁₅, 5-NHCO(CH₂)₄NPhPr, 6-SH, 2-Me pyrimidine |
| 192 | 4-NBu₂, 5-NHCO(CH₂)₄NPhPr, 6-SH pyrimidine |
| 193 | 4-NBu₂, 5-NHCO(CH₂)₄NPhPr, 6-SH, 2-NMe₂ pyrimidine |
| 194 | 4-NPr₂, 5-NHCO(CH₂)₄NPhPr, 6-OMe, 2-Me pyrimidine |
| 195 | 4-NBu₂, 5-NHCO(CH₂)₄NPhPr, 6-OMe, 2-Me pyrimidine |
| 196 | 4-NBu₂, 5-NHCO(CH₂)₄NPhPr, 6-OEt, 2-Me pyrimidine |
| 197 | 4-NBu₂, 5-NHCO(CH₂)₄NPhPr, 6-OEt pyrimidine |
| 198 | 4-OMe, 5-NHCO(CH₂)₄NPhPr, 6-OMe, 2-Me pyrimidine |
| 199 | 4-NEt₂, 5-NHCO(CH₂)₄NPhHex, 6-SH, 2-Me pyrimidine |
| 200 | 4-NBu₂, 5-NHCO(CH₂)₄NPr(c-Hex), 6-SH, 2-Me pyrimidine |

EXAMPLE 201

Preparation of N-(4,6-dimethoxy-2-methylpyrimidin-5-yl)-2-(N-phenyl-N-propylamino)acetamide To a solution of the product obtained in EXAMPLE 109 (0.23 g) in methylene chloride (5 ml), 2-chloro-1-methylpyridinium iodide (0.47 g) and triethylamine (0.49 ml) were added under ice-cooling. After stirring for 40 minutes at room temperature, a solution of the product obtained in EXAMPLE 102 (0.20 g) in methylene chloride (1 ml) was added dropwise to the mixture under ice cooling. The reaction mixture was stirred at room temperature for 30 minutes and then refluxed for 1 hour. After cooling to room temperature, the mixture was diluted with water and extraction with ethyl acetate. The organic layers was washed with water and saturated sodium chloride in order and dried over anhydrous sodium sulfate and solvents ware removed under reduced pressure. The residue was purified by silica gel column chromatography (ethyl acetate:hexane=1:1) and followed by crystallization from ether-petroleum ether to give 0.18 g (44%) of the objective compound.

Melting point: 173.1°–174.4° C.

IR(KBr) ν cm⁻¹: 3238, 1671, 1580, 1530, 1509, 1359, 1135

NMR(90 MHz, DMSO-d₆) δ ppm: 9.04(1H, s), 7.32–7.02(2H, m), 6.78–6.48(3H, m), 3.98(2H, s), 3.84(6H, s), 3.50–3.18(2H, m), 2.51(3H, s), 1.77–1.32(2H, m), 0.90(3H, t, J=7.2 Hz)

The following compounds were prepared in a similar manner as EXAMPLE 201.

EXAMPLE 202

N-[4,6-bis(N,N-diethylamino)-2-methylpyrimidin-5-yl]-2-(N-phenyl-N-propylamino)acetamide Yield: 6%

Melting point: 146.2°–147.5° C.

IR(KBr) ν cm⁻¹: 2962, 1672, 1600, 1548, 1508, 1445, 1438, 1283

NMR(90 MHz, DMSO-d$_6$) δ ppm: 7.60(1H, s), 7.37–6.34(5H, m), 3.97 (2H, s), 3.64–3.30(2H, m), 3.22(8H, q, J=6.9 Hz), 2.37(3H, s), 1.76–1.46(2H, m), 1.20(3H, t, J=6.9 Hz), 0.99(12H, t, J=6.9 Hz)

EXAMPLE 203

N-[4,6-bis(methylthio)-2-methylpyrimidin-5-yl]-2-(N-phenyl-N-propylamino)acetamide Yield: 6%

Melting point: 195.1°–196.3° C.

IR(KBr) ν cm$^{-1}$: 3246, 1676, 1521, 1507

NMR(90 MHz, DMSO-d$_6$) δ ppm: 9.58(1H, s), 7.26–7.02(2H, m), 6.78–6.48(3H, m), 4.03(2H, s), 3.48–3.00(2H, m), 2.56(3H, s), 2.44(6H, s), 1.80–1.32(2H, m), 0.91(3H, t, J=7.1 Hz)

EXAMPLE 204

N-[4,6-bis(hexylthio)-2-methylpyrimidin-5-yl]-4-(N-phenyl-N-propylamino)butanamide Yield: 26%

IR(KBr) ν cm$^{-1}$: 3228, 1655, 1598, 1506

NMR(90 MHz, CDCl$_3$ ) δ ppm: 7.38–7.02(2H, m), 6.84–6.36(3H, m), 3.72–2.82(8H, m), 2.57(3H, s), 2.46–1.08(22H, m), 0.90(9H, t, J=7.1 Hz)

EXAMPLE 205

N-[4-mercapto-2-methyl-6-(N-phenyl-N-propylamino)pyrimidin-5-yl]-6-(N-phenyl-N-propylamino)hexanamide Yield: 14%

Melting point: 121.9°–125.9° C.

IR(KBr) ν cm$^{-1}$: 2957, 1602, 1594, 1560, 1506, 1459, 1422

NMR(90 MHz, DMSO-d$_6$) δ ppm: 13.06(1H, s), 7.76(1H, s), 7.30–6.84(7H, m), 6.66–6.36(3H, m), 3.96–3.72(2H, m), 3.33–3.06(4H, m), 2.58–2.28(2H, m), 2.36(3H, s), 1.68–1.08(10H, m), 0.98–0.72(6H, m)

The structures of the compounds of examples 201–205 are shown in the following.

Example No.

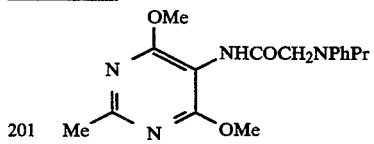
201

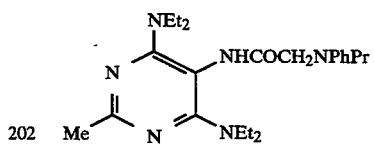
202

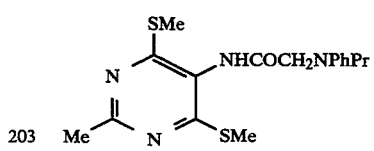
203

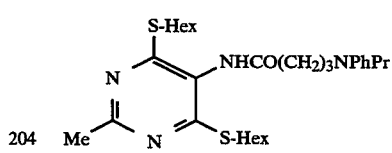
204

Example No.

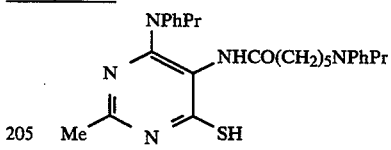
205

EXAMPLE 206

Preparation of N-[4-(N,N-diethylamino)-2-methyl-6-methylthiopyrimidin-5-yl]-3-(N-phenyl-N-propylamino)propionamide To a solution of the product obtained in EXAMPLE 110 (0.27 g) and N-methylmorpholine (0.15 ml) in methylene chloride (4 ml), isobutyl chloroformate (0.17 ml) was added dropwise under ice-salt-cooling. After stirring for 30 minutes, a solution of the product obtained in EXAMPLE 105 (0.27 g) in methylene chloride (1 ml) was added dropwise to the reaction mixture. After stirring for 3 hours at room temperature, N-methylmorpholine (0.15 ml) and isobutyl chloroformate (0.17 ml) were added to the mixture and the mixture was stirred at room temperature for another 10 hours. The reaction mixture was diluted with water and extracted with ethyl acetate. The obtained organic layer was washed with water, saturated sodium bicarbonate and saturated sodium chloride in order. After drying over anhydrous sodium sulfate, the organic layer was concentrated under reduced pressure. The residue was crystallized from ether-hexane to give 0.26 g (46%) of the objective compound.

Melting point: 147.1°–148.8° C.

IR(KBr) ν cm$^{-1}$: 3249, 2964, 2928, 1647, 1599, 1556, 1523, 1505

NMR(90 MHz, DMSO-d$_6$) δ ppm: 9.33(1H, s), 7.29–7.03(2H, m), 6.77–6.43(3H, m), 3.73–3.00(8H, m), 2.64–2.28(2H, m), 2.35(6H, s), 1.71–1.37(2H, m), 1.06(6H, t, J=6.9 Hz), 0.88(3H, t, J=7.3 Hz)

The following compound was prepared in a similar manner as EXAMPLE 206.

EXAMPLE 207

N-[4-(N,N-diethylamino)-2-methyl-6-methylthiopyrimidin-5-yl]-4-(N-phenyl-N-propylamino)butanamide Yield: 9%

Melting point: 97.3°–98.8° C.

IR(KBr) ν cm$^{-1}$: 2965, 1649, 1598, 1546, 1506, 1413

NMR(90 MHz, DMSO-d$_6$) δ ppm: 9.28(1H, s), 7.26–7.00(2H, m), 6.78–6.42(3H, m), 3.63–3.03(8H, m), 2.46–2.22(2H, m), 2.35(3H, s), 2.34(3H, s), 2.04–1.32(4H, m), 1.08(6H, t, J=6.8 Hz), 0.88(3H, t, J=7.3 Hz)

The structures of the compounds of examples 206–207 are shown in the following.

Example No.

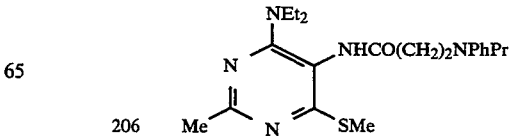
206

Example No.

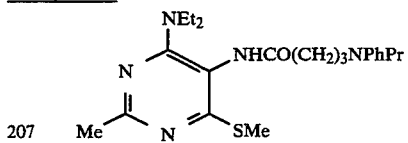

207

EXAMPLE 208

Preparation of 2-bromo-N-[4-(N,N-diethylamino)-2-methyl-6-methylthiopyrimidin-5-yl]acetamide To a solution of the product obtained in EXAMPLE 105 (16 g) and triethylamine (13.8 ml) in methylene chloride (240 ml) was added dropwise, and then the solution of bromoacetyl bromide (7.4 ml) in methylene chloride (10 ml) was added dropwise under ice cooling. After stirring at room temperature for 1 hour, bromoacetyl bromide (0.6 ml) was added to the solution and the mixture was stirred under reflux for 15 minutes. After cooling to room temperature, the mixture was poured into water and decanted and then the aqueous layer was extracted with methylene chloride. The organic layer was washed with aqueous sodium chloride in order, dried over ahnhydrous saturated aqueous sodium bicarbonate, water and saturated sodium sulfate and then concentrated under reduced pressure. The residue was purified by silica gel column chlomatography (ethyl acetate:hexane=1:4.–1:2) to give 13.2 g (54%) of the objective compound.

Melting point: 173.1°–174.1° C.

IR(KBr) $\nu$ cm$^{-1}$: 3228, 1662, 1552, 1536

NMR(90 MHz, CDCl$_3$) $\delta$ ppm: 7.54(1H, s), 4.04(2H, s), 3.48(4H, q, J=7.1 Hz), 2.47(3H, s), 2.44(3H, s), 1.17(6H, t, J=7.1 Hz)

The following compound was prepared in a similar manner as EXAMPLE 208.

EXAMPLE 209

2-bromo-N-[4,6-bis(methylthio)-2-methylpyrimidin-5-yl]acetamide

Yield: 75%

Melting point: 223.8°–225.5° C.

IR(KBr) $\nu$ cm$^{-1}$: 3421, 1669, 1542, 1509, 1408, 811

NMR(90 MHz, CDCl$_3$) $\delta$ ppm: 7.50(1H, s), 4.06(2H, s), 2.61(3H, s), 2.52(6H, s)

EXAMPLE 210

Preparation of 2-(N-benzyl-N-propylamino) N-[4-(N,N-diethylamino)-2-methyl-6-methylthiopyrimidin-5-yl]acetamide A solution of the product obtained in EXAMPLE 208 (0.5 g) and N-benzyl -N-propylamine (0.43 g) in diethylaniline (5 ml) was stirred at 100° C. for 1.5 hour. After cooling to room temperature, the reaction mixture was poured into water and extracted with ethyl acetate. The organic layer was washed with water and saturated sodium chloride, dried over anhydrous sodium sulfate and then concentrated under reduced pressure. the residue was crystallized from ether to give 0.5 g (84%) of the objective compound.

Melting point: 161.3°–164.1° C.

IR(KBr) $\nu$ cm$^{-1}$: 3226, 1671, 1549, 1463, 1426

NMR (90 MHz, CDCl$_3$) $\delta$ ppm: 8.36(1H, s), 7.32(5H, s), 3.71(2H, s), 3.34(4H, q, J=7.0 Hz), 3.22(2H, s), 2.63(2H, t, J=6.9 Hz), 2.44(3H, s), 2.43(3H, s), 1.92–1.41(2H, m), 0.97(6H, t, J=7.0 Hz), 0.95(3H, t, J=7.1 Hz)

The following compounds were prepared in a similar manner as EXAMPLE 210.

EXAMPLE 211

N-[4-(N,N-diethylamino)-2-methyl-6-methylthiopyrimidin-5-yl]-2-(N,N-dipropylamino)acetamide Yield: 28%

Melting point: 66.2°–69.8° C.

IR (KBr) $\nu$ cm$^{-1}$: 3261, 1666, 1558, 1414

NMR(90 MHz, CDCl$_3$) $\delta$ ppm: 8.55(1H, s), 3.48(4H, q, J=7.1 Hz), 3.21(2H, s), 2.57(4H, t, J=7.1 Hz), 2.46(3H, s), 2.43(3H, s), 1.80–1.26(4H, m), 1.14(6H, t, J=7.1 Hz), 0.92 (6H, t, J=7.1 Hz)

EXAMPLE 212

N-[4-(N,N-diethylamino)-2-methyl-6-methylthiopyrimidin-5-yl]-2-(4-phenylpiperazinyl)acetamide Yield: 55%

Melting point: 166.5°–168.4° C.

IR(KBr) $\nu$ cm$^{-1}$: 3259, 1670, 1599, 1548, 1493, 1421, 1360, 1239

NMR(90 MHz, CDCl$_3$) $\delta$ ppm: 8.52(1H, s), 7.41–7.14(2H, m), 7.05–6.72(3H, m), 3.87(4H, q, J=7.1 Hz), 3.36–3.09(4H, m), 3.23(2H, s), 3.00–2.70(4H, m), 2.47(3H, s), 2.44(3H, s), 1.17(6H, t, J=7.1 Hz)

EXAMPLE 213

N-[4,6-bis(methylthio)-2-methylpyrimidin-5-yl]-2-(N-phenyl-N-propylamino)acetamide Yield: 60%

Melting point: 195.1°–196.3° C.

IR(KBr) $\nu$ cm$^{-1}$: 3246, 1676, 1521, 1507

NMR(90 MHz, DMSO-d$_6$) $\delta$ ppm: 9.58(1H, s), 7.26–7.02(2H, m), 6.78–6.48(3H, m), 4.03(2H, s), 3.48–3.00(2H, m), 2.56(3H, s), 2.44(6H, s), 1.80–1.32(2H, m), 0.91(3H, t, J=7.1 Hz)

The structures of the compounds of examples 208–213 are shown in the following.

Example No.

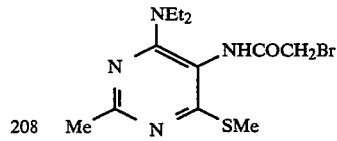

208

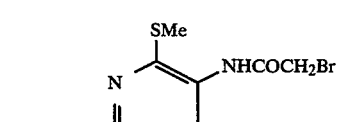

209

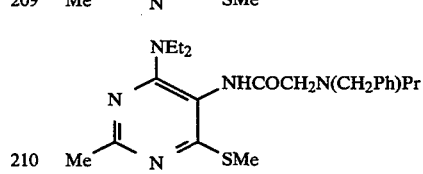

210

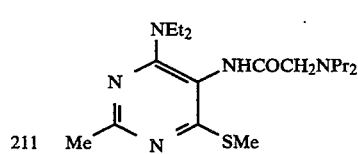

211

| Example No. | |
|---|---|
| 212 | 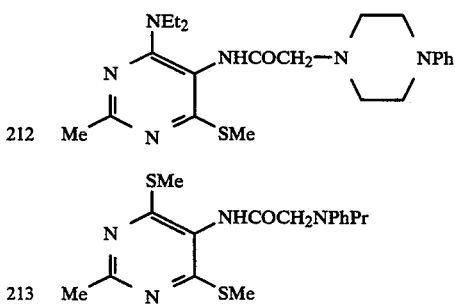 |
| 213 | |

EXAMPLE 214

Preparation of N-[4-(N,N-diethylamino)-2-methyl-6-methylthiopyrimidin-5-yl]-2-(N-phenyl -N propylamino)acetamide To a suspension of the product obtained in EXAMPLE 133 (1.2 g) and triehtylamine (0.63 ml) in methylene chloride (12 ml), methyl iodide (0.8 ml) was added under ice cooling. After stirring at room temperature for 1.5 hours, triethylamine (0.63 ml) and methyl iodide (0.28 ml) were added and the solution was stirred for another 1.5 hour. The mixture was poured into water and extracted twice with ethyl acetate. The combined organic layer was washed with water and saturated sodium chloride in order, dried over anhydrous sodium sulfate and then concentrated under reduced pressure. The residue was purified by silica gel column chromatography (ethyl acetate:hexane=1:3) and followed by crystallization from ether to give 1.08 g (90%) of the objective compound.

Melting point: 173.2°–175.2° C.
IR(KBr) $\nu$ cm$^{-1}$: 3226, 2960, 1668, 1549, 1519, 1507, 1426, 1416
NMR(90 MHz, DMSO-d$_6$) $\delta$ ppm: 9.32(1H, s), 7.24–7.03(2H, m), 6.77–6.47(3H, m), 4.03(2H, s), 3.56–3.21(6H, m), 2.36(3H, s), 2.35(3H, s), 1.71–1.41(2H, m), 1.07(6H, t, J=6.9 Hz), 0.89(3H, t, J=7.4 Hz)

The following compounds were prepared in a similar manner as EXAMPLE 214.

EXAMPLE 215

N-[2-methyl-4-methylthio-6-(N-phenyl-N-propylamino)pyrimidin-5-yl]-3-(N-phenyl-N-propylamino)propionamide
Yield: 79%
Melting point: 132.9°–134.1° C.
IR(KBr) $\nu$ cm$^{-1}$: 2962, 1663, 1599, 1543, 1530, 1506, 1494, 1416
NMR(90 MHz, DMSO-d$_6$) $\delta$ ppm: 8.42(1H, s), 7.37–6.90(7H, m), 6.64–6.43(3H, m), 3.81(2H, t, J=5.9 Hz), 3.30–2.96(4H, m), 2.58–2.34(2H, m), 2.47(3H, s), 2.36(3H, s), 1.80–1.33(4H, m), 0.86(6H, t, J=6.6 Hz)

EXAMPLE 216

N-[4-(N,N-diethylamino)-2-methyl-6-methylthiopyrimidin-5-yl]-3-(N-phenyl-N-propylamino)propionamide
Yield: 76%
Melting point: 147.1°–148.8° C.
IR (KBr) $\nu$ cm$^{-1}$: 3249, 2964, 2928, 1647, 1599, 1556, 1523, 1505
NMR(90 MHz, DMSO-d$_6$) $\delta$ ppm: 9.33(1H, s), 7.29–7.03(2H, m), 6.77–6.43(3H, m), 3.73–3.00(8H, m), 2.64–2.28(2H, m), 2.35(6H, s), 1.71–1.37(2H, m), 1.06(6H, t, J=6.9 Hz), 0.88(3H, t, J=7.3 Hz)

EXAMPLE 217

N-[4-(N,N-diethylamino)-2-methyl-6-methylthiopyrimidin-5-yl]-3-(N-hexyl-N-phenylamino)propionamide
Yield: 74%
Melting point: 110.5°–111.7° C.
IR(KBr) $\nu$ cm$^{-1}$: 3232, 2927, 1653, 1599, 1552, 1506, 1414, 1365
NMR(270 MHz, DMSO-d$_6$) $\delta$ ppm: 9.37(1H, s), 7.16(2H, dd, J=8.3 and 7.3 Hz), 6.67(2H, d, J=8.3 Hz), 6.58(1H, t, J=7.3 Hz), 3.58(2H, t, J=7.1 Hz), 3.40(4H, q, J=6.9 Hz), 3.28(2H, t, J=7.4 Hz), 2.56–2.45(2H, 2.36(3H, s), 2.35(3H, s), 1.57–1.44(2H, m), 1.34m), 1.21(6H, m), 1.06(6H, t, J=6.9 Hz), 0.87(3H, t, J=6.6 Hz)

EXAMPLE 218

N-[2-methyl-4-methylthio-6-(N-phenyl-N-propylamino)pyrimidin-5-yl]-4-(N-phenyl-N-propylamino)butanamide
Yield: 73%
Melting point: 140.9°–142.7° C.
IR(KBr) $\nu$ cm$^{-1}$: 3245, 1670, 1542, 1533, 1506, 1415
NMR(90 MHz, CDCl$_3$) $\delta$ ppm: 7.62–6.84(7H, m), 6.75–6.42(3H, m), 5.39(1H, s), 3.88(2H, t, J=7.6 Hz), 3.33–2.88(4H, m), 2.54(3H, s), 2.45(3H, s), 1.98–1.32(8H, m), 0.89(6H, t, J=7.3 Hz)

EXAMPLE 219

N-[4-(N,N-dimethylamino)-2-methyl-6-methylthiopyrimidin-5-yl]-4-(N-phenyl-N-propylamino)butanamide
Yield: 85%
Melting point: 145.0°–146.8° C.
IR(KBr) $\nu$ cm$^{-1}$: 1644, 1548, 1506, 1413, 1399
NMR(90 MHz, DMSO-d$_6$) $\delta$ ppm: 9.25(1H, s), 7.22–6.98(2H, m), 6.75–6.36(3H, m), 3.42–3.00(4H, m), 3.03(6H, s), 2.36(3H, s), 2.34(3H, s), 2.16–1.30(6H, m), 0.88(3H, t, J=7.1 Hz)

EXAMPLE 220

N-[4-(N,N-diethylamino)-2-methyl-6-methylthiopyrimidin-5-yl]-4-(N-phenyl-N-propylamino)butanamide
Yield: 62%
Melting point: 97.3°–98.8° C.
IR(KBr) $\nu$ cm$^{-1}$: 2965, 1649, 1598, 1546, 1506, 1413
NMR (90 MHz, DMSO-d$_6$ ) $\delta$ ppm: 9.28(1H, s), 7.26–7.00(2H, m), 6.78–6.42(3H, m), 3.63–3.03(8H, m), 2.46–2.22(2H, m), 2.35(3H, s), 2.34(3H, s), 2.04–1.32(4H, m), 1.08(6H, t, J=6.8 Hz), 0.88(3H, t, J=7.3 Hz)

EXAMPLE 221

N-[4-(N,N-dibutylamino)-2-methyl-6-methylthiopyrimidin-5-yl]-4-(N-phenyl-N-propylamino)butanamide
Yield: 58%
Melting point: 129.5°–130.8° C.
IR(KBr) $\nu$ cm$^{-1}$: 3242, 2956, 2929/ 1654, 1551, 1506, 1415, 1376
NMR (90 MHz, DMSO-d$_6$ ) $\delta$ ppm: 9.28(1H, s), 7.17–6.87(2H, m), 6.72–6.64(3H, m), 3.48–3.00(8H, m), 2.40–2.06(2H, m), 2.34(6H, s), 1.98–1.02(12H, m), 0.88(9H, t, J=6.4 Hz)

EXAMPLE 222

N-[4-(N,N-dihexylamino)-2-methyl-6-methylthiopyrimidin-5-yl]-4-(N-phenyl-N-propylamino)butanamide.
Yield: 45%
Melting point: 114.6°–117.8° C.
IR(KBr) $\nu$ cm$^{-1}$: 2957, 2930, 1654, 1551, 1507, 1415
NMR(90 MHz, DMSO-d$_6$) $\delta$ ppm: 9.26(1H, s), 7.20–6.96(2H, m), 6.72–6.36(3H, m), 3.48–3.06(8H, m), 2.34(6H, s), 1.98–1.65(2H, m), 1.65–0.99(20H, m), 0.99–0.69(9H, m)

EXAMPLE 223

N-[4-(N-benzyl-N-heptylamino)-2-methyl-6-methylthiopyrimidin-5-yl]-4-(N-phenyl-N-propylamino)butanamide
Yield: 64%
Melting point: 109.2°–111.8° C.
IR(KBr) $\nu$ cm$^{-1}$: 3220, 2956, 2928, 1654, 1545, 1506
NMR(90 MHz, CDCl$_3$) $\delta$ ppm: 7.44–7.02(7H, m), 6.72–6.48(3H, m), 6.09(1H, s), 4.65(2H, s), 3.60–3.00(6H, m), 2.47(3H, s), 2.44(3H, s), 2.04–1.08(16H, m), 0.91(3H, t, J=6.9 Hz), 0.87(3H, t, J=4.6 Hz)

EXAMPLE 224

N-[4-(N,N-diethylamino)-2-methyl-6-methylthiopyrimidin-5-yl]-4-(N-methyl-N-phenylamino)butanamide
Yield: 47%
Melting point: 146.0°–148.3° C.
IR(KBr) $\nu$ cm$^{-1}$: 3241, 1666, 1600, 1557, 1507, 1411
NMR(90 MHz, DMSO-d$_6$) $\delta$ ppm: 9.25(1H, s), 7.26–6.99(2H, m), 6.78–6.4.5(3H, m), 3.57–3.18(6H, m), 2.88(3H, s), 2.40–2.16(2H, m), 2.34(6H, s), 1.98–1.62(2H, m), 1.08(6H, t, J=6.8 Hz)

EXAMPLE 225

N-[4-(N,N-diethylamino)-2-methyl-6-methylthiopyrimidin-5-yl]-4-(N-hexyl-N-phenylamino)butanamide
Yield: 85%
Melting point: 90.1°–91–4° C.
IR(KBr) $\nu$ cm$^{-1}$: 3210, 2956, 2930, 1649, 1545, 1507
NMR(90 MHz, DMSO-d$_6$) $\delta$ ppm: 9.25(1H, s), 7.23–6.93(2H, m), 6.75–6.36(3H, m), 3.60–2.94(8H, m), 2.40–2.13(2H, m), 2.35(3H, s), 2.34(3H, s), 1.95–1.62(2H, m), 1.62–1.17(8H, m), 1.08(6H, t, J=6.8 Hz), 0.86(3H, t, J=4.6 Hz)

EXAMPLE 226

N-[4-(N,N-dipropylamino)-2-methyl-6-methylthiopyrimidin-5-yl]-4-(N-hexyl-N-phenylamino)butanamide
Yield: 74%
Melting point: 101.4°–102.8° C.
IR(KBr) $\nu$ cm$^{-1}$: 2960, 2929, 1653, 1551, 1506, 1416, 1375
NMR(270 MHz, DMSO-d$_6$) $\delta$ ppm: 9.31(1H, s), 7.12(2H, dd, J=7.9 and 7.3 Hz), 6.66(2H, d, J=7.9 Hz), 6.53(1H, t, J=7.3 Hz), 3.45–3.018(8H, m), 2.43–2.18(2H, m),2.35(3H, s), 2.34(3H, s), 1.90–1.72(2H, m), 1.65–1.37(6H, m), 1.37–1.18(6H, m), 0.86(3H, t, J=6.6 Hz), 0.80(6H, t, J=7.4 Hz)

EXAMPLE 227

N-[4-(N,N-dibutylamino)-2-methyl-6-methylthiopyrimidin-5-yl]-4-(N-hexyl-N-phenylamino)butanamide
Yield: 41%
Melting point: 95.2°–96.7° C.
IR(KBr) $\nu$ cm$^{-1}$: 3207, 1654, 1551, 1507, 1414
NMR(90 MHz, DMSO-d$_6$) $\delta$ ppm: 9.28(1H, s), 7.26–6.96(2H, m), 6.78–6.36(3H, m), 3.54–2.82(8H, m), 2.40–2.10(2H, m), 2.34(6H, s), 2.04–0.96(18H, m), 0.87(9H, t, J=5.9 Hz)

EXAMPLE 228

N-[4-(N-benzyl-N-ethylamino)-2-methyl-6-methylthiopyrimidin-5-yl]-4-(N-hexyl-N-phenylamino)butanamide
Yield: 98%
Melting point: 153.9°–154.6° C.
IR(KBr) $\nu$ cm$^{-1}$: 1655, 1599, 1547, 1504, 1444, 1412, 1369
NMR(270 MHz, DMSO-d$_6$) $\delta$ ppm: 9.26(1H, s), 7.31–7.15(5H, m), 7.11(2H, dd, J=8.2 and 7.3 Hz), 6.63(2H, d, J=8.2 Hz), 6.52(1H, t, J=7.3 Hz), 4.74(2H, s), 3.52–3.28(2H, m), 3.28–3.12(4H, m), 2.37(3H, s), 2.35(3H, s), 2.26–1.88(2H, m), 1.76–1.59(2H, m), 1.54–1.39(2H, m), 1.33–1.19(6H, m), 1.08(3H, t, J=6.8 Hz), 0.86(3H, t, J=6.4 Hz)

EXAMPLE 229

N-[4-(N-benzyl-N-heptylamino)-2-methyl-6-methylthiopyrimidin-5yl]-4-(N-hexyl-N-phenylamino)butanamide
Yield: 62%
Melting point: 93.8°–94.6° C.
IR(KBr) $\nu$ cm$^{-1}$: 3257, 2929, 1656, 1549, 1506
NMR(90 MHz, DMSO-d$_6$) $\delta$ ppm: 9.27(1H, s), 7.32–6.90(7H, m), 6.72–6.36(3H, m), 4.77(2H, s), 3.48–2.82(6H, m), 2.36(6H, s), 2.22–1.92(2H, m), 1.86–1.02(20H, m), 0.96–0.66(6H, m)

EXAMPLE 230

N-[4-(N-butylamino)-2-methyl-6-methylthiopyrimidin-5-yl]-4-(N-hexyl-N-phenylamino)butanamide
Yield: 65%
Melting point: 111.7°–114.8° C.
IR(KBr) $\nu$ cm$^{-1}$: 3303, 2954, 2929, 1648, 1590, 1560, 1505
NMR(90 MHz, DMSO-d$_6$) $\delta$ ppm: 8.88(1H, s), 7.20–6.96(2H, m), 6.72–6.36(4H, m), 3.42–3.09(6H, m), 2.40–2.16(2H, m), 2.35(6H, s), 1.98–1.65(2H, m), 1.65–1.02(12H, m), 0.87(6H, t, J=6.3 Hz)

EXAMPLE 231

N-[2-methyl-4-methylthio-6-morpholinopyrimidin-5-yl]-4-(N-hexyl-N-phenylamino)butanamide
Yield: 50%
Melting point: 100.5°–103.4° C.
IR(KBr) $\nu$ cm$^{-1}$: 2957, 2927, 1652, 1542, 1506, 1414
NMR(90 MHz, DMSO-d$_6$) $\delta$ ppm: 9.31(1H, s), 7.26–6.96(2H, m), 6.78–6.42(3H, m), 3.66–3.42(8H, m), 3.42–3.06(4H, m), 2.43–2.16(2H, m), 2.40(3H, s), 2.37(3H, s), 1.92–1.59(2H, m), 1.59–1.08(8H, m), 0.86(6H, t, J=5.4 Hz)

EXAMPLE 232

N-[4-(N,N-diethylamino)-6-methylthiopyrimidin-5-yl]-4-(N-hexyl-N-phenylamino)butanamide Yield: 76%
Melting point: 83.9°–85.0° C.
IR(KBr) ν cm$^{-1}$: 2929, 1653, 1599, 1552, 1504, 1373
NMR(270 MHz, DMSO-d$_6$) δ ppm: 9.42(1H, s), 8.27(1H, s), 7.12(2H, dd, J=8.6 and 7.3 Hz), 6.67(2H, d, J=8.6 Hz), 6.53(1H, t, J=7.3 Hz), 3.54–3.38(4H, m), 3.38–3.20(4H, m), 2.42–2.22(2H, m), 2.36(3H, s), 1.90–1.76(2H, m), 1.56–1.42(2H, m), 1.36–1.20(6H, m), 1.10(6H, t, J=6.9 Hz), 0.87(3H, t, J=6.6 Hz)

EXAMPLE 233

N-[4-(N,N-diethylamino)-2-methoxy-6-methylthiopyrimidin-5-yl]-4-(N-hexyl-N-phenylamino)butanamide
Yield: 81%
Melting point: 74.0°–75.7° C.
IR(KBr) ν cm$^{-1}$: 1651, 1599, 1552, 1506, 1464, 1443, 1375, 1333
NMR(270 MHz, DMSO-d$_6$) δ ppm: 9.20(1H, s), 7.12(2H, dd, J=8.3 and 7.3 Hz), 6.67(2H, d, J=8.3 Hz), 6.53(1H; t, J=7.3 Hz), 3.81(3H, s), 3.54–3.22(8H, m), 2.40–2.18(2H, m), 2.33(3H, s), 1.92–1.74(2H, m), 1.58–1.42 (2H, m), 1.38–1.20(6H, m), 1.10(6H, t, J=6.9 Hz), 0.87(3H, t, J=6.3 Hz)

EXAMPLE 234

N-[4-(N,N-diethylamino)-2,6-bis(methylthio)pyrimidin-5-yl]-4-(N-hexyl-N-phenylamino)butanamide
Yield: 83%
Melting point: 86.3°–87.4° C.
IR(KBr) ν cm$^{-1}$: 2926, 1651, 1597, 1537, 1506, 1348, 1037
NMR(270 MHz, DMSO-d$_6$) δ ppm: 9.33(1H, s), 7.12(2H, dd, J=8.3 and 7.3 Hz), 6.67(2H, d, J=8.3 Hz), 6.53(1H, t, J=7.3 Hz), 3.56–3.18(8H, m), 2.45(3H, s), 2.42–2.22(2H, m), 2.33(3H, s), 1.90–1.72(2H, m), 1.57–1.40(2H, m), 1.38–1.20(6H, m), 1.09(6H, t, J=6.9 Hz), 0.87(3H, t, J=6.8 Hz)

EXAMPLE 235

4-(N-cycloheptyl-N-phenylamino)-N-[4-(N,N-diethylamino)-2-methyl-6-methylthiopyrimidin-5-yl]butanamide
Yield: 75%
Melting point: 134.3°–135.5° C.
IR(KBr) ν cm$^{-1}$: 2927, 1653, 1547, 1502, 1429, 1414, 1360
NMR(270 MHz, DMSO-d$_6$) δ ppm: 9.30(1H, s), 7.13(2H, dd, J=8.6 and 7.3 Hz), 6.74(2H, d, J=8.6 Hz), 6.57(1H, t, J=7.3 Hz), 3.76–3.62(1H, m), 3.52–3.34(4H, m), 3.25–3.10(2H, m), 2.40–2.25(2H, m), 2.36(3H, s), 2.34(3H, s), 1.88–1.38(14H, m), 1.08(6H, t, J=6.9 Hz)

EXAMPLE 236

4-(N-decyl-N-phenylamino)-N-[4-(N,N-diethylamino)-2-methyl-6-methylthiopyrimidin-5-yl]butanamide
Yield: 80%
Melting point: 81.9°–83.6° C.
IR(KBr) ν cm$^{-1}$: 3255, 2925, 2853, 1651, 1546, 1508
NMR(90 MHz, DMSO-d$_6$) δ ppm: 9.27(1H, s), 7.23–6.96(2H, m), 6.72–6.3.9(3H, m), 3.57–3.12(8H, m), 2.36(3H, s), 2.34(3H, s), 1.92–1.62(2H, m), 1.62–1.14(18H, m), 1.09(6H, t, J=6.8 Hz), 0.85(3H, t, J=5.6 Hz)

EXAMPLE 237

4-[N-(4-butylphenyl)-N-propylamino]-N-[4-(N,N-diethylamino)-2-methyl-6-methylthiopyrimidin-5-yl]butanamide
Yield: 97%
IR(KBr) ν cm$^{-1}$: 3240, 1655, 1549, 1519, 1414
NMR(90 MHz, DMSO-d$_6$) δ ppm: 9.27(1H, s), 6.94(2H, d, J=8.1 Hz), 6.59(2H, d, J=8.1 Hz), 3.60–2.88(8H, m), 2.46–2.04(4H, m), 2.34(6H, s), 1.98–1.26(8H, m), 1.09(6H, t, J=6.9 Hz), 0.88(6H, t, J=6.8 Hz)

EXAMPLE 238

N-[4-(N,N-diethylamino)-2-methyl-6-methylthiopyrimidin-5-yl]-4-[N-(4-methoxyphenyl)-N-propylamino)butanamide
Yield: 14%
Melting point: 69.2°–72.8° C.
IR(KBr) ν cm$^{-1}$: 3233, 2962, 2930/1662, 1550, 1514, 1413, 1242
NMR(90 MHz, DMSO-d$_6$) δ ppm: 9.24(1H, s), 6.87–6.54(4H, m), 3.64(3H, s), 3.57–2.94(8H, m), 2.40–2.13(2H, m), 2.35(3H, s), 2.33(3H, s), 1.92–1.29(4H, m), 1.08(6H, t, J=6.8 Hz), 0.86(3H, t, J=7.1 Hz)

EXAMPLE 239

N-[4-(N,N-diethylamino)-2-methyl-6-methylthiopyrimidin-5-yl]-4-[N-hexyl-N-(4-methoxyphenyl)amino]butanamide
Yield: 67%
Melting point: 41.2°–44.2° C.
IR(KBr) ν cm$^{-1}$: 2956, 2929, 1655, 1549, 1514, 1429, 1246
NMR(270 MHz, CDCl$_3$) δ ppm: 6.88–6.69(5H, m), 3.75(3H, s), 3.44(4H, q, J=6.9 Hz), 3.25–3.05(4H, m), 2.45(3H, s), 2.43(3H, s), 2.52–2.36(2H, m), 2.08–1.98(2H, m), 1.58–1.40(2H, m), 1.37–1.20(6H, m), 1.13(6H, t, J=6.9 Hz), 0.88(3H, t, J=6.6 Hz)

EXAMPLE 240

N-[4-(N,N-diethylamino)-2-methyl-6-methylthiopyrimidin-5-yl]-4-[N-hexyl-N-(2-methoxyphenyl)amino ]butanamide
Yield: 99%
IR(neat) ν cm$^{-1}$: 3238, 2929, 1659, 1552, 1500, 1414, 1238
NMR(270 MHz, DMSO-d$_6$) δ ppm: 9.19(1H, s), 6.96–6.77(4H, m), 3.76(3H, s), 3.46–3.33 (4H, m), 3.12–2.97(4H, m), 2.35(3H, s), 2.32(3H, s), 2.30–2.19(2H, m), 1.74–1.60(2H, m), 1.42–1.30(2H, m), 1.30–1.15(6H, m), 1.06(6H, t, J=6.8 Hz), 0.83(3H, t, J=6.6 Hz)

EXAMPLE 241

N-[4-(N,N-diethylamino)-2-methyl-6-methylthiopyrimidin-5-yl]-4-[N-(2,4-difluorophenyl)-N-propylamino]butanamide
Yield: 86%
Melting point: 87.5°–89.0° C.
IR(KBr) ν cm$^{-1}$: 3232, 2967, 2931, 1655, 1559, 1511, 1429, 1419
NMR(90 MHz, DMSO-d$_6$) δ ppm: 9.19(1H, s), 7.26–6.75(3H, m), 3.39(4H, q, J=6.8 Hz), 3.09(2H, t, J=7.1 Hz), 3.00(2H, t, J=7.3 Hz), 2.40–2.10(2H, m), 2.34(3H, s), 2.32(3H, s), 1.86–1.20(4H, m), 1.06(6H, t, J=6.8 Hz), 0.82(3H, t, J=7.1 Hz)

EXAMPLE 242

4-(N-benzyl-N-propylamino)-N-[4-(N,N-diethylamino)-2-methyl-6-methylthiopyrimidin-5-yl]butanamide
Yield: 51%
Melting point: 74.6°–77.1° C.
IR(KBr) ν cm$^{-1}$: 3228, 2958, 1656, 1550, 1416
NMR(90 MHz, DMSO-d$_6$) δ ppm: 9.18(1H, s), 7.38–7.08(5H, m), 3.53(2H, s), 3.48–3.00(4H, m), 2.40–1.98(6H, m), 2.35(3H, s), 2.33(3H, s), 1.92–1.20(4H, m), 1.07(6H, t, J=6.8 Hz), 0.81(3H, t, J=7.1 Hz)

EXAMPLE 243

4-(N-benzyl-N-heptylamino)-N-[4-(N,N-diethylamino)-2-methyl-6-methylthiopyrimidin-5-yl]butanamide
Yield: 45%
IR(neat) ν cm$^{-1}$: 2956, 2930, 1654/ 1559, 1542, 1414
NMR(90 MHz, CDCl$_3$) δ ppm: 7.38–7.00(6H, m), 3.59(2H, s), 3.43(4H, q, J=6.9 Hz), 2.76–1.16(18H, m), 2.44(6H, s), 1.14(6H, t, J=6.9 Hz), 0.87(3H, t, J=5.0 Hz)

EXAMPLE 244

N-[4-(N,N-diethylamino)-2-methyl-6-methylthiopyrimidin-5-yl]-4-(N-tetrahydroquinolino)butanamide
Yield: 64%
Melting point: 146.9°–147.8° C.
IR(KBr) ν cm$^{-1}$: 3254, 1656, 1551, 1507, 1416
NMR (90 MHz, DMSO-d$_6$) δ ppm: 9.26(1H, s), 7.08–6.72(2H, m), 6.72–6.30(2H, m), 3.66–3.00(8H, m), 2.67(2H, t, J=6.6 Hz), 2.40–2.10(2H, m), 2.36(3H, s), 2.34(3H, s), 2.04–1.56(4H, m), 1.08(6H, t, J=6.8 Hz)

EXAMPLE 245

N-[4-(N,N-diethylamino)-2-methyl-6-methylthiopyrimidin-5-yl]-5-(N-phenyl-N-propylamino)pentanamide
Yield: 79%
Melting point: 132.1°–135.2° C.
IR(KBr) ν cm$^{-1}$: 1648, 1546, 1506, 1416, 1361
NMR(90 MHz, DMSO-d$_6$) δ ppm: 9.20(1H, s), 7.26–6.90(2H, m), 6.72–6.39(3H, m), 3.63–2.84 (8H, m), 2.46–2.04(2H, m), 2.35(3H, s), 2.32(3H, s), 1.80–1.26(6H, m), 1.07(6H, t, J=6.9 Hz), 0.88(3H, t, J=7.2 Hz)

EXAMPLE 246

N-[4-(N,N-dipropylamino)-2-methyl-6-methylthiopyrimidin-5-yl]-5-(N-phenyl-N-propylamino)pentanamide
Yield: 77%
Melting point: 115.3°–116.2° C.
IR(KBr) ν cm$^{-1}$: 2958, 1649, 1599, 1547, 1504, 1416, 1363, 750
NMR(270 MHz, DMSO-d$_6$) δ ppm: 9.22(1H, s), 7.11(2H, dd, J=8.6 and 7.3 Hz), 6.61(2H, d, J=8.6 Hz), 6.52(1H, t, J=7.3 Hz), 3.46–3.10(8H, m), 2.42–2.14(2H, m), 2.34(3H, s), 2.31(3H, s), 1.72–1.32(10H, m), 0.88(3H, t, J=7.4 Hz), 0.80(6H, t, J=7.3 Hz)

EXAMPLE 247

N-[4-(N,N-dibutylamino)-2-methyl-6-methylthiopyrimidin-5-yl]-5-(N-phenyl-N-propylamino)pentanamide
Yield: 41%
Melting point: 70.4°–72.8° C.
IR(KBr) ν cm$^{-1}$: 3213, 2957, 1653, 1551, 1506, 1417
NMR(90 MHz, DMSO-d$_6$) δ ppm: 9.22(1H, s), 7.26–6.90(2H, m), 6.72–6.36(3H, m), 3.66–2.88(8H, m), 2.42–2.10(2H, m), 2.33(3H, s), 2.32(3H, s), 1.80–1.02(14H, m), 0.87(9H, t, J=6.6 Hz)

EXAMPLE 248

N-[4-(N-benzyl-N-ethylamino)-2-methyl-6-methylthiopyrimidin-5-yl]-5-(N-phenyl-N-propylamino)pentanamide
Yield: 77%
Melting point: 99.6°–100.3° C.
IR(KBr) ν cm$^{-1}$: 1657, 1597, 1551, 1506, 1437, 1414, 1363
NMR(270 MHz, DMSO-d$_6$) δ ppm: 9.19(1H, s), 7.33–7.17(5H, m), 7.11(2H, dd, J=8.3 and 7.3 Hz), 6.59 (2H, d, J=8.3 Hz), 6.52(1H, t, J=7.3 Hz), 4.73(2H, s), 3.49–3.30(2H, m), 3.30–3.10(4H, m), 2.36(3H, s), 2.33(3H, s), 2.21–1.88(2H, m), 1.60–1.39(6H, m), 1.06(3H, t; J=6.8 Hz), 0.88(3H, t, J=7.4 Hz)

EXAMPLE 249

N-[4-(N-benzyl-N-heptylamino)-2-methyl-6-methylthiopyrimidin-5-yl]-5-(N-phenyl-N-propylamino)pentanamide
Yield: 14%
IR(neat) ν cm$^{-1}$: 2956, 2928, 2856, 1654, 1598, 1541, 1506
NMR(90 MHz, DMSO-d$_6$) δ ppm: 9.19(1H, s), 7.29–6.99(7H, m), 6.66–6.39(3H, m), 4.73(2H, s), 3.36–3.06(6H, m), 2.34(6H, s), 2.25–1.95(2H, m), 1.68–1.02(16H, m), 0.99–0.72(6H, m)

EXAMPLE 250

N-[4-(N,N-dibutylamino)-6-methylthiopyrimidin-5-yl]-5-(N-phenyl-N-propylamino)pentanamide
Yield: 78%
Melting point: 69.7°–71.1° C.
IR(KBr) ν cm$^{-1}$: 2958, 2931, 1659, 1554, 1508, 1371
NMR(270 MHz, DMSO-d$_6$) δ ppm: 9.35(1H, s), 8.26(1H, s), 7.12(2H, dd, J=8.2 and 7.3 Hz), 6.62(2H, d, J=8.2 Hz), 6.53(1H, t, J=7.3 Hz), 3.46–3.15(8H, m), 2.40–2.20(2H, m), 2.33(3H, s), 1.69–1.38(10H, m), 1.30–1.14(4H, m), 0.88(3H, t, J=7.4 Hz), 0.87(6H, t, J=7.3 Hz)

EXAMPLE 251

N-[4-(N,N-dibutylamino)-2-(N,N-diethylamino)-6-methylthiopyrimidin-5-yl]-5-N-phenyl-N-propylamino)pentanamide
Yield: 50%
Melting point: 90.1°–91.3° C.
IR(KBr) ν cm$^{-1}$: 2956, 1657, 1560, 1541, 1506, 1398, 1375, 1350
NMR(270 MHz, DMSO-d$_6$) δ ppm: 8.93(1H, s), 7.11(2H, dd, J=8.6 and 7.3 Hz), 6.61(2H, d, J=8.6 Hz), 6.52(1H, t, J=7.3 Hz), 3.43–3.12(8H, m), 3.06(6H, s), 2.40–2.06(2H, m), 2.28(3H, s), 1.70–1.30(10H, m), 1.22(4H, m), 0.88(3H, t, J=7.3 Hz), 0.87(6H, t, J=7.1 Hz)

EXAMPLE 252

N-[4-(N,N-diethylamino)-2-methyl-6-methylthiopyrimidin-5-yl]-5-(N-hexyl-N-phenylamino)pentanamide
Yield: 92%
Melting point: 135.9°–138.3° C.
IR(KBr) ν cm$^{-1}$: 3215, 2929, 1651, 1548, 1505, 1415

NMR(90 MHz, DMSO-d₆) δ ppm: 9.18(1H, s), 7.23–6.96(2H, m), 6.69–6.39(3H, m), 3.40(4H, q, J=7.0 Hz), 3.33–3.03(4H, m), 2.40–2.13(2H, m), 2.35(3H, s), 2.32(3H, s), 1.86–1.17(12H, m), 1.07(6H, t, J=7.0 Hz), 0.86(3H, t, J=5.8 Hz)

EXAMPLE 253

(N-cyclohexyl-N-propylamino)-N-[4-(N,N-dibutylamino)-2-methyl-6-methylthiopyrimidin-5-yl]pentanamide Yield: 17%

Melting point: 93.6°–94.7° C.

IR (KBr) ν cm⁻¹: 2933, 2860, 1659, 1549, 1454, 1414

NMR (270 MHz, DMSO-d₆) δ ppm: 8.64 (1H, s), 3.44–2.84(9H, m), 2.44–2.20(2H, m), 2.34(3H, s), 2.02–1.02(24H, m), 0.92(3H, t, J=7.3 Hz), 0.89(6H, t, J=7.6 Hz)

EXAMPLE 254

N-[4-isopropylthio-2-methyl-6-(N-phenyl-N-propylamino)pyrimidin-5-yl]-3-(N-phenyl-N-propylamino)propionamide Yield: 24%

Melting point: 66.2°–69.8° C.

IR(KBr) ν cm⁻¹: 3235, 1661, 1528, 1496, 1411

NMR(90 MHz, CDCl₃) δ ppm: 7.44–6.87(7H, m), 6.81–6.39(3H, m), 5.72(1H, s), 4.20–3.75 (1H, m), 3.88(2H, t, J=7.3 Hz), 3.54–3.00(4H, m), 2.52 (3H, s), 1.82(2H, t, J=7.3 Hz), 1.74–1.44(4H, m), 1.35(6H, d, J=6.9 Hz), 0.89(6H, t, J=6.9 Hz)

EXAMPLE 255

N-[4-benzylthio-2-methyl-6-(N-phenyl-N-propylamino)pyrimidin-5-yl]-3-(N-phenyl-N-propylamino)propionamide Yield: 78%

Melting point: 141.9°–145.8° C.

IR(KBr) ν cm⁻¹: 3257, 1662, 1542, 1529, 1506, 1494, 1416

NMR(90 MHz, CDCl₃) δ ppm: 7.68–6.40(15H, m), 5.73(1H, s), 4.37(2H, s), 3.88(2H, t, J=7.4 Hz), 3.32(2H, t, J=7.3 Hz), 3.13(2H, t, J=7.3 Hz), 2.56(3H, s), 1.79(2H, t, J=6.9 Hz), 1.74–1.14(4H, m), 0.89(3H, t, J=7.3 Hz), 0.83(3H, t, J=6.9 Hz)

EXAMPLE 256

N-[2-methyl-4-(N-phenyl-N-propylamino)-6-propylthiopyrimidin-5-yl]-4-(N-phenyl-N-propylamino)-butanamide Yield: 55%

Melting point: 141.2°–143.0° C.

IR(KBr) ν cm⁻¹: 2959, 1656, 1533, 1507, 1493, 1415

NMR(90 MHz, CDCl₃) δ ppm: 7.38–6.84(7H, m), 6.72–6.48(3H, m), 5.39(1H, s), 3.88(2H, t, J=7.4 Hz), 3.30–2.84(6H, m), 2.51(3H, s), 2.36–1.84(10H, m), 1.10–0.72(9H, m)

EXAMPLE 257

N-[4-hexylthio-2-methyl-6-(N-phenyl-N-propylamino)pyrimidin-5-yl]-4-(N-phenyl-N-propylamino)butanamide Yield: 36%

Melting point: 95.8°–97.5° C.

IR(KBr) ν cm⁻¹: 2958, 2931, 1540, 1533, 1506, 1493

NMR(90 MHz, CDCl₃) δ ppm: 7.38–6.84(7H, m), 6.72–6.48(3H, m), 5.39(1H, s), 3.88(2H, t, J=7.4 Hz), 3.30–2.94(6H, m), 2.52(3H, s), 1.80–1.02(16H, m), 0.89(9H, t, J=7.3 Hz)

EXAMPLE 258

N-[4-benzylthio-2-methyl-6-(N-phenyl-N-propylamino)pyrimidin-5-yl]-4-(N-phenyl-N-propylamino)butanamide Yield: 56%

Melting point: 137.6°–140.1° C.

IR(KBr) ν cm⁻¹: 3244, 1662, 1541, 1533, 1529, 1506, 1494, 1414

NMR(90 MHz, CDCl₃) δ ppm: 7.80–6.36(15H, m), 5.36(1H, s), 4.37(2H, s), 3.89(2H, t, J=7.3 Hz), 3.30–2.94(4H, m), 2.56(3H, s), 1.98–1.08(8H, m), 0.89(3H, t, J=7.3 Hz), 0.86(3H, t, J=7.3 Hz)

EXAMPLE 259

N-[4-benzylthio-6-(N,N-dietylamino)-2-methyl-pyrimidin-5-yl]-4-(N-phenyl-N-propylamino)butanamide Yield: 36%

Melting point: 66.3°–69.1° C.

IR(KBr) ν cm⁻¹: 3234, 1654, 1550, 1506

NMR(90 MHz, CDCl₃) δ ppm: 7.62–6.90(7H, m), 6.78–6.18(3H, m), 4.37(2H, s), 3.72–2.88(8H, m), 2.46(3H, s), 2.04–1.20(6H, m), 1.13(6H, t, J=6.9 Hz), 0.87(3H, t, J=7.1 Hz)

EXAMPLE 260

N-[4-(N,N-dietylamino)-6-ethylthio-2-methylpyrimidin-5-yl]-4-(N-hexyl-N-phenylamino)butanamide Yield: 72%

Melting point: 80.2°–82.4° C.

IR(KBr) ν cm⁻¹: 3224, 1651, 1545, 1518, 1506

NMR(270 MHz, DMSO-d₆) δ ppm: 9.27(1H, s), 7.12(2H, dd, J=8.6 and 7.3 Hz), 6.67(2H, d, J=8.6 Hz), 6.53(1H, t, J=7.3 Hz), 3.52–3.20(8H, m), 3.08–2.88(2H, m), 2.42–2.22(2H, m), 2.35(3H, s), 1.88–1.72(2H, m), 1.58–1.42(2H, m), 1.36–1.22(6H, m), 1.21(3H, t, J=7.3 Hz), 1.08(6H, t, J=6.8 Hz), 0.86(3H, t, J=6.6 Hz)

EXAMPLE 261

N-[4-(N,N-dietylamino)-2-methyl-6-propylthiopyrimidin-5-yl]-4-(N-hexyl-N-phenylamino)butanamide Yield: 56%

Melting point: 77.8°–78.9° C.

IR(KBr) ν cm⁻¹: 3226, 2960, 2929, 1655, 1554, 1504, 1414

NMR(270 MHz, DMSO-d₆) δ ppm: 9.26(1H, s), 7.11(2H, dd, J=7.9 and 7.3 Hz), 6.66(2H, d, J=7.9 Hz), 6.53(1H, t, J=7.3 Hz), 3.50–3.20(8H, m), 3.06–2.90(2H, m), 2.42–2.20(2H, m), 2.34(3H, s), 1.92–1.74(2H, m), 1.66–1.42(4H, m), 1.36–1.18(6H, m), 1.08(3H, t, J=6.8 Hz), 0.92(3H, t, J=7.4 Hz), 0.86(3H, t, J=6.9 Hz)

EXAMPLE 262

N-[4-(N,N-dietylamino)-6-isopropylthio-2-methyl-pyrimidin-5-yl]-4-(N-hexyl-N-phenylamino)butanamide Yield: 70%

Melting point: 84.8°–86.5° C.

IR(KBr) ν cm⁻¹: 2960, 2931, 1653, 1547, 1506, 1414

NMR(270 MHz, DMSO-d₆) δ ppm: 9.21(1H, s), 7.11(2H, dd, J=7.6 and 6.9 Hz), 6.66(2H, d, J=7.6 Hz), 6.54(1H, t, J=6.9 Hz)3.94–3.78(1H, m), 3.50–3.20(8H, m), 2.40–2.22(2H, m), 2.34(3H, s), 1.88–1.72(2H, m), 1.56–1.40(2H, m), 1.36–1.20(12H, m), 1.07(6H, t, J=6.5 Hz), 0.86(3H, t, J=5.9 Hz)

EXAMPLE 263

N-(4-benzyloxy-6-isopropyl-2-methylpyrimidin-5-yl)-4-(N-phenyl-N-propylamino)butanamide
Yield: 31%
Melting point: 55.8°–58.4° C.
IR(KBr) ν cm$^{-1}$: 3274, 2963, 1648, 1598, 1548, 1506
NMR(90 MHz, CDCl$_3$) δ ppm: 7.50–6.48(11H, m), 5.24(2H, s), 3.48–2.64(5H, m), 2.58–1.32(6H, m), 2.45(3H, s), 1.19(6H, d, J=6.9 Hz), 0.91(3H, t, J=7.3 Hz)

EXAMPLE 264

Preparation of N-[4-(N,N-diethylamino)-2-(N,N-dimethylamino)-6-methylthiopyrimidin-5-yl]-4-(N-hexyl-N-phenylamino)butanamide Starting from N-[4-(N,N-dietylamino)-2-(N,N-dimethylamino)-6-mercaptopyrimidin-5-yl]-4-(N-hexyl-N-phenylamino)butanamide (prepared in a similar manner as EXAMPLE 132 from the product obtained in EXAMPLE 9 and the product obtained in EXAMPLE 114), the objective compound was prepared in a similar manner as EXAMPLE 214.

Yield: 12%
Melting point: 114.3°–115.3° C.
IR (KBr) ν cm$^{-1}$: 3230, 2931, 1653, 1558, 1506, 1400, 1367
NMR(270 MHz, DMSO-d$_6$) δ ppm: 9.00(1H; s), 7.11(2H, dd,, J=8.3 and 7.3 Hz), 6.66(2H, d, J=8.3 Hz), 6.53(1H, t, J=7.3 Hz), 3.53–3.10(8H, m), 3.07(6H, s), 2.45–2.10(2H, m), 2.31(3H, s), 1.92–1.70(2H, m), 1.60–1.37(2H, m), 1.40–1.15(6H, m), 1–09(6H, t, J=6.9 Hz), 0.87(3H, t, J=6.9 Hz)

The structures of the compounds of examples 214–264 are shown in the following.

Example No.

214 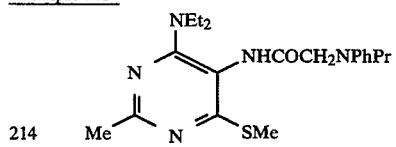

215 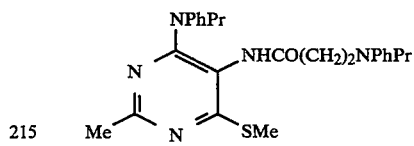

216 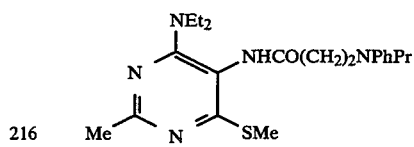

217 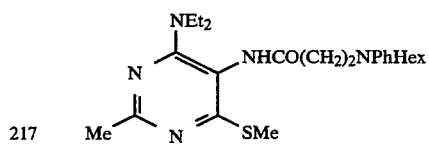

218 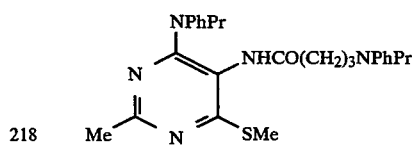

Example No.

219 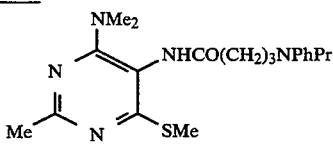

220 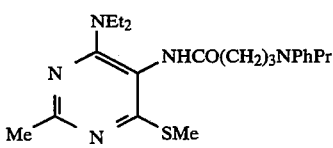

221 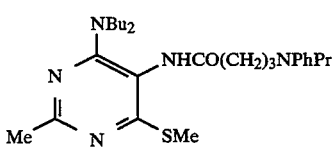

222 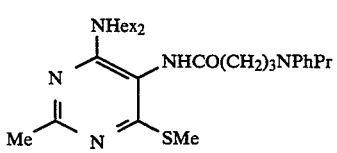

223 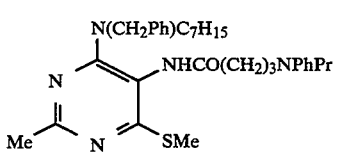

224 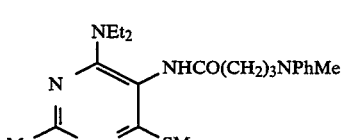

225 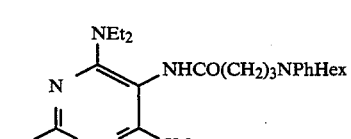

226 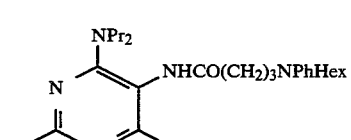

227 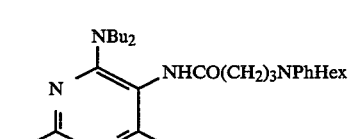

228 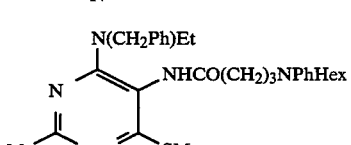

229 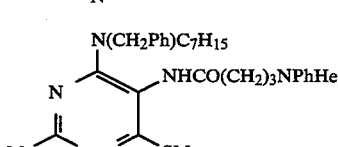

-continued
| Example No. | | Example No. | |
|---|---|---|---|
| 230 | 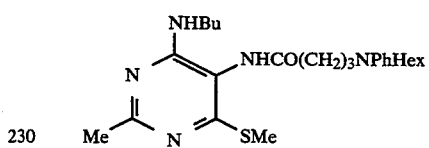 | 239 | 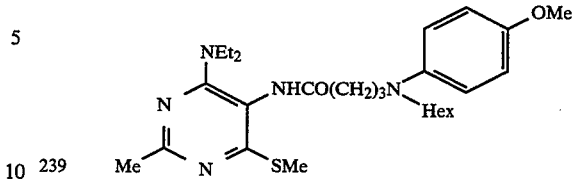 |
| 231 | 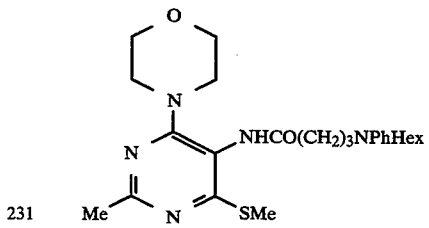 | 240 | 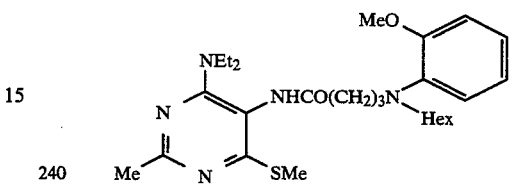 |
| 232 | 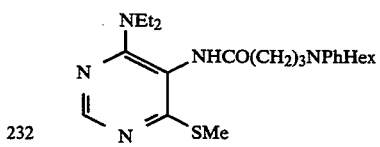 | 241 | 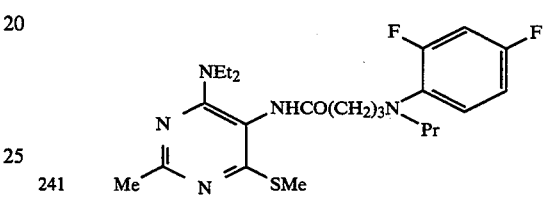 |
| 233 | 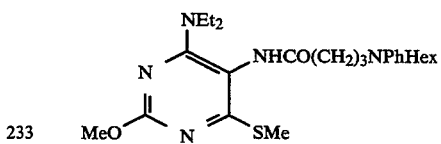 | 242 | 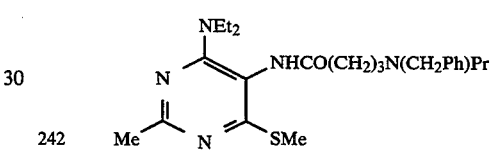 |
| 234 | 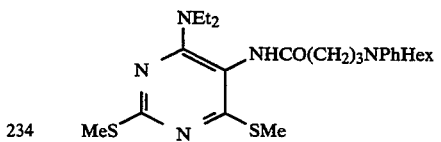 | 243 | 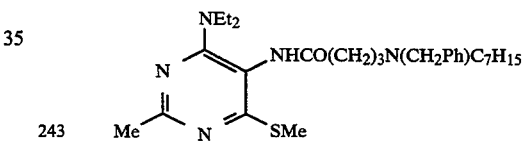 |
| 235 | 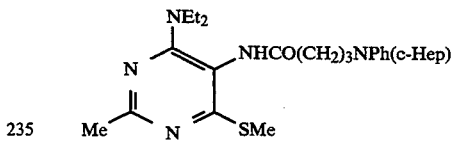 | 244 | 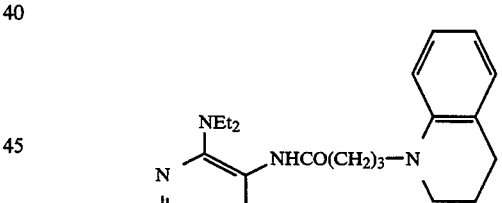 |
| 236 | 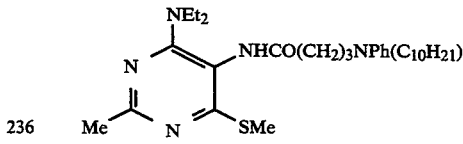 | 245 | 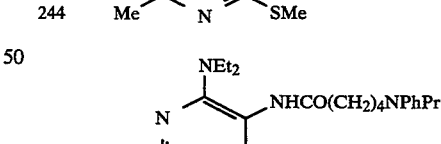 |
| 237 | 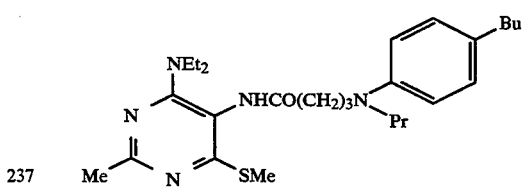 | 246 | 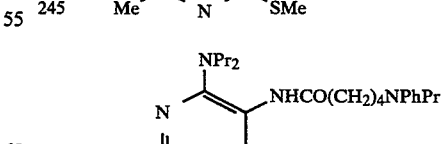 |
| 238 | 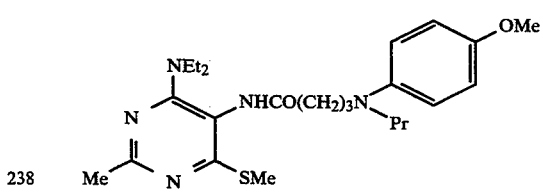 | 247 | 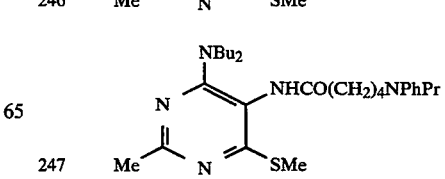 |

-continued

| Example No. | Structure |
|---|---|
| 248 | 2-Me, 4-N(CH₂Ph)Et, 5-NHCO(CH₂)₄NPhPr, 6-SMe pyrimidine |
| 249 | 2-Me, 4-N(CH₂Ph)C₇H₁₅, 5-NHCO(CH₂)₄NPhPr, 6-SMe pyrimidine |
| 250 | 4-NBu₂, 5-NHCO(CH₂)₄NPhPr, 6-SMe pyrimidine |
| 251 | 2-Me₂N, 4-NBu₂, 5-NHCO(CH₂)₄NPhPr, 6-SMe pyrimidine |
| 252 | 2-Me, 4-NEt₂, 5-NHCO(CH₂)₄NPhHex, 6-SMe pyrimidine |
| 253 | 2-Me, 4-NBu₂, 5-NHCO(CH₂)₄NPr(c-Hex), 6-SMe pyrimidine |
| 254 | 2-Me, 4-NPhPr, 5-NHCO(CH₂)₂NPhPr, 6-S-iPr pyrimidine |
| 255 | 2-Me, 4-NPhPr, 5-NHCO(CH₂)₂NPhPr, 6-SCH₂Ph pyrimidine |
| 256 | 2-Me, 4-NPhPr, 5-NHCO(CH₂)₃NPhPr, 6-SPr pyrimidine |
| 257 | 2-Me, 4-NPhPr, 5-NHCO(CH₂)₃NPhPr, 6-SHex pyrimidine |
| 258 | 2-Me, 4-NPhPr, 5-NHCO(CH₂)₃NPhPr, 6-SCH₂Ph pyrimidine |
| 259 | 2-Me, 4-NEt₂, 5-NHCO(CH₂)₃NPhPr, 6-SCH₂Ph pyrimidine |
| 260 | 2-Me, 4-NEt₂, 5-NHCO(CH₂)₃NPhHex, 6-SEt pyrimidine |
| 261 | 2-Me, 4-NEt₂, 5-NHCO(CH₂)₃NPhHex, 6-SPr pyrimidine |
| 262 | 2-Me, 4-NEt₂, 5-NHCO(CH₂)₃NPhHex, 6-S-iPr pyrimidine |
| 263 | 2-Me, 4-OCH₂Ph, 5-NHCO(CH₂)₃NPhPr, 6-i-Pr pyrimidine |
| 264 | 2-Me₂N, 4-NEt₂, 5-NHCO(CH₂)₃NPhHex, 6-SMe pyrimidine |

EXAMPLE 265

Preparation of N-(4-chloro-6-isopropyl-2-methyl-pyrimidin-5-yl)-4-(N-phenyl-N-propylamino)butanamide A mixture of the product obtained in EXAMPLE 153 (12.0 g) and phosphorus oxychloride(5 ml) was stirred at room temperature for 1 hour. The reaction mixture was poured into ice-water and extracted with ethyl acetate. The organic layer was washed with water and saturated sodium chloride, dried over anhydrous sodium sulfate and then concentrated under reduced pressure. The residue was purified by silica gel column chromatography (ethyl acetate:hexane=1:4) to give 300mg (29%) the objective compound.

IR(neat) $\nu$ cm$^{-1}$: 3246, 2966, 1661, 1599, 1568, 1506, 1417, 1369

NMR(90 MHz, CDCl₃) $\delta$ ppm: 7.38–7.02(2H, m), 6.90–6.48(4H, m), 3.54–2.76(5H, m), 2.68(3H, s), 2.50(2H, t, J=5.6 Hz), 2.26–1.80(2H, m), 1.80–1.38(2H, m), 1.22(6H, d, J=6.9 Hz), 0.92(3H, t, J=7.3 Hz)

The structure of the compound of Example 265 is shown in the following.

Example No.

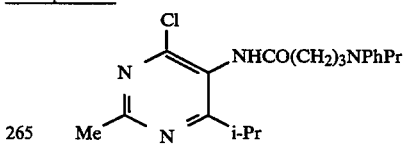

265

EXAMPLE 266

Preparation of N-[4-(N,N-diethylamino)-6-isopropyl-2-methylpyrimidin-5-yl]-4-(N-phenyl-N-propylamino)-butanamide A mixture of the product obtained in EXAMPLE 265 (100mg) and diethylamine (2 ml) was stirred under reflux for 4 hours. After evaporation of excess diethylamine under reduced pressure, the residue was poured into water and extracted with ethyl acetate. The organic layer was washed with water and saturated sodium chloride, dried over anhydrous sodium sulfate and then concentrated under reduced pressure. The residue was purified by silica gel column chromatography (ethyl acetate:hexane=3:7) and followed by crystallization from ether to give 51mg (47%) of the objective compound.

Melting point: 129.4°-130.8° C.

IR(KBr) $\nu$ cm$^{-1}$: 3232, 2962, 1654, 1562, 1507, 1367, 751

NMR(90 MHz, CDCl$_3$) $\delta$ ppm: 7.38–6.96(2H, m), 6.84–6.30(4H, m), 3.90–2.64(9H, m), 2.47(3H, s), 2.42(2H, t, J=7.3 Hz), 2.25–1.31(4H, m), 1.17(6H, d, J=6.6 Hz), 1.13(6H, t, J=6.6 Hz), 0.92(3H, t, J=7.1 Hz)

EXAMPLE 267

Preparation of N-(4-isopropyl-6-mercapto-2-methylpyrimidin-5-yl)-4-(N-phenyl-N-propylamino)butanamide To a solution of the product obtained in EXAMPLE 265 (200mg) in ethanol (1 ml), sodium hydrosulfide (100mg) was added and the mixture was stirred at room temperature for 2 hours. The reaction mixture was poured into water and extracted with ethyl acetate. The organic layer was washed with water and saturated sodium chloride, dried over anhydrous sodium sulfate and then concentrated under reduced pressure. The residue was purified by silica gel column chromatography (ethyl acetate:hexane=3:7) and followed by crystallization from ether to give 156mg (78%) of the objective compound.

Melting point: 144.1°-145.2° C.

IR(KBr) $\nu$ cm$^{-1}$: 3277, 2961, 1663, 1596, 1571, 1506, 1245, 746

NMR(90 MHz, CDCl$_3$) $\delta$ ppm: 12.40(1H, s), 7.42(1H, s), 7.31–6.97(2H, m), 6.81–6.42(3H, m), 3.54–2.76(5H, m), 2.70–2.28(2H, m), 2.52(3H, s), 2.28–1.80(2H, m), 1.80–1.38(2H, m), 1.20(6H, d, J=6.6 Hz), 0.92(3H, t, J=7.3 Hz)

EXAMPLE 268

Preparation of N-(4-isopropyl-2-methyl-6-methylthiopyrimidin-5-yl)-4-(N-phenyl-N-propylamino)butanamide Starting from the product obtained in EXAMPLE 267, the objective compound was prepared in a similar manner as EXAMPLE 214.

Yield: 96%

Melting point: 103.1°-104.6° C.

IR(KBr) $\nu$ cm$^{-1}$: 3215, 2966, 1648, 1598, 1542, 1505, 1409, 1368, 748

NMR(90 MHz, CDCl$_3$) $\delta$ ppm: 7.35–6.99(2H, m), 6.84–6.30(4H, m), 3.60–2.79(5H, m), 2.64–2.28(2H, m), 2.63(3H, s), 2.50(3H, s), 2.22–1.80(2H, m), 1.80–1.35(2H, m), 1.19(6H, d, J=6.9 Hz), 0.92(3H, t, J=7.1 Hz)

EXAMPLE 269

Preparation of N-[4-(N,N-diethylamino)-2-methylpyrimidin-5-yl]-2-(N-phenyl-N-propylamino)acetamide To a suspension of Raney Ni (4 g) in methanol, the product obtained in EXAMPLE 133 (0.2 g) was added. After stirring for 1 hour at room temperature, the reaction mixture was filtrated to remove the catalyst. The filtrate was concentrated under reduced pressure, and the residue was dissolved in ethyl acetate. The organic solution was washed with water and saturated sodium chloride, dried over anhydrous sodium sulfate and then concentrated under reduced pressure. The residue was crystallized from hexane to give 67 mg (37%) of the objective compound.

Melting point: 96.6°-98.1° C.

IR(KBr) $\nu$ cm$^{-1}$: 3269, 1663, 1578, 1508

NMR(90 MHz, DMSO-d$_6$) $\delta$ ppm: 9.37(1H, s), 7.71(1H, s), 7.32–7.02(2H, m), 6.78–6.48(3H, m), 4.03(2H, s), 3.66–3.12(6H, m), 2.34(3H, s), 1.86–1.32(2H, m), 1.05(6H, t, J=6.9 Hz), 0.90(3H, t, J=7.6 Hz)

The following compound was prepared in a similar manner as EXAMPLE 269.

EXAMPLE 270

N-[2-methyl-(4-N-phenyl-N-propylamino)pyrimidin-5-yl]-3-(N-phenyl-N-propylamino)propionamide Yield: 61%

Melting point: 114.0°-116.2° C.

IR(KBr) $\nu$ cm$^{-1}$: 3226, 2959, 1652, 1598, 1580, 1504, 1421

NMR(90 MHz, DMSO-d$_6$) $\delta$ ppm: 8.59(1H, s), 7.91(1H, s), 7.40–6.93(7H, m), 6.65–6.40(3H, m), 3.88(2H, t, J=7.4 Hz), 3.34–2.95(4H, m), 2.48(3H, s), 1.84–1.28(6H, m), 0.86(6H, t, J=7.3 Hz)

The structures of the compounds of the Examples 266–270 are shown in the following.

Example No.

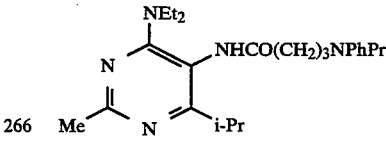

266

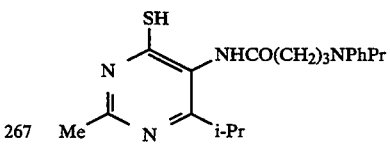

267

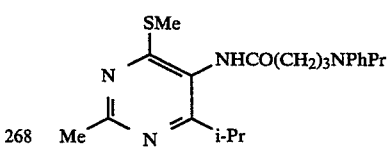

268

| Example No. | |
|---|---|
| 269 | 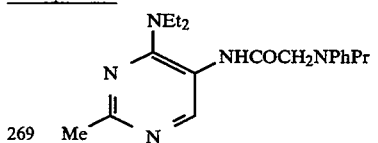 |
| 270 | 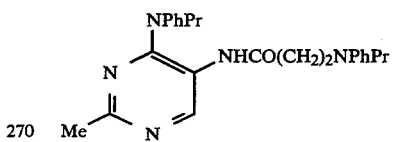 |

EXAMPLE 271

Preparation of N-[4-(N,N-diethylamino)-2-methyl-6-methylthiopyrimidin-5-yl]-4-[N-(4-hydroxyphenyl)-N-propylamino]butanamide To a solution of the product obtained in EXAMPLE 238 (2.0 g) in acetic acid (20 ml), hydrobromic acid (48%; 3 ml) and concentrated sulfuric acid (0.5 ml) were added. After stirring under reflux for 12 hours, the mixture was poured into water (20 ml). The aqueous solution was neutralized with 3N sodium hydroxide and extracted twice with ethyl acetate. The collected organic layer was washed with saturated sodium bicarbonate, water and saturated sodium chloride, dried over anhydrous sodium sulfate and then concentrated under reduced pressure. The residue was purified by silica gel column chromatography (ethyl acetate:hexane=1:2) to give 0.74 g (38%) of the objective compound.

IR(KBr) $\nu$ cm$^{-1}$: 3234, 1660, 1551, 1514, 1414

NMR(270 MHz, DMSO-d$_6$) $\delta$ ppm: 9.26(1H, s), 8.52(1H, s), 6.59(4H, s), 3.53–3.26(4H, m), 3.22–3.01(4H, m), 2.42–2.18(2H, m), 2.36(3H, s), 2.33(3H, s), 1.86–1.65(2H, m), 1.54–1.37(2H, m), 1.08(6H, t, J=6.8 Hz), 0.85(3H, t, J=7.3 Hz)

EXAMPLE 272

Preparation of 4-[N-(4-bromophenyl)-N-hexylamino]-N-[4-(N,N-diethylamino)-2-methyl-6-methylthiopyrimidin-5yl]butanamide To a solution of the product obtained in EXAMPLE 225 (100mg) in carbon tetrachloride (2 ml) was added N-bromosuccinimide (45mg) and the mixture was stirred at room temperature for 20 minutes. The reaction mixture was poured into water and extracted twice with ethyl acetate. The collected organic layer was washed with saturated sodium chloride, dried over anhydrous sodium sulfate and then concentrated under reduced pressure. The residue was purified by silica gel column chromatography (ethyl acetate:hexane=1:3) to give 62 mg (53%) of the objective compound.

Melting point: 89.8°–93.0° C.

IR(KBr) $\nu$ cm$^{-1}$: 2927, 1653, 1547, 1500, 1414, 1049, 808

NMR(270 MHz, DMSO-d$_6$) $\delta$ ppm: 9.30(1H, s), 7.23(2H, d, J=8.9 Hz), 6.63(2H, d, J=8.9 Hz), 3.53–3.19(8H, m), 2.43–2.22(2H, m), 2.36(3H, s), 2.34(3H, s), 1.88–1.71(2H, m), 1.56–1.41(2H, m), 1.35–1.19(6H, m), 1.08(6H, t, J=6.9 Hz), 0.86(3H, t, J=6.6 Hz)

The structures of the compounds of examples 271–272 are shown in the following.

| Example No. | |
|---|---|
| 271 | 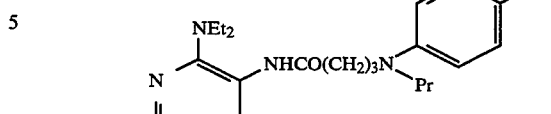 |
| 272 | 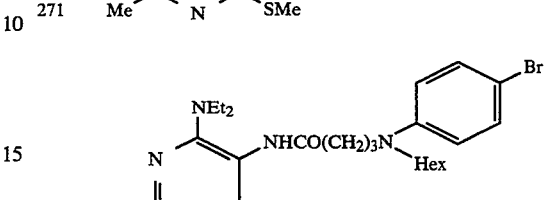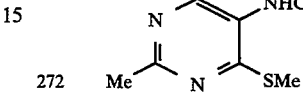 |

Now, typical but non-limiting examples of formulations of the compound of the present invention will be shown below.

Formulations A (Capsules)

The compound of the example 159(500 g of weight), 485 g of lactose and 15 g of magnesium stearate were weighed and mixed until the mixture became homogeneous. The mixture was then filled in No.1 hard gelatin capsule at 300 mg each to obtain capsule preparations.

Formulations B (Tablets)

The compound of the example 187(500 g of weight), 350 g of lactose, 120 g of potato starch, 15 g of polyvinyl alcohol and 15 g of magnesium stearate were weighed. The weighed amount of compound 187, lactose and potato starch were mixed until accomplishing homogeneity. Then aqueous solution of polyvinylalcohol was added to the mixture and granulated by wet process. The granules were then dried, mixed with the weighed magnesium stearate and pressed into tablets, each weighing 300 mg.

Formulations C (Powders)

The compound of the example 245(200 g of weight), 790 g of lactose and 10 g of magnesium stearate were weighed and mixed until the mixture became homogeneous to obtain 20 % powder preparation.

Formulations D (Rectal suppositories)

The compound of the example 148(100 g of weight), 180 g of polyethyleneglycol 1500 and 720 g of polyethyleneglycol 4000 were ground well in a mortar and formulated into suppository by melting and casting into 1 g of appropriate mold.

What is claimed is:

1. A pyrimidine derivative represented by the formula (I) or a salt thereof:

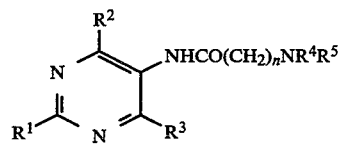   (I)

wherein R$^{10}$ represents hydrogen atom, an alkyl group of straight or branched chain having 1 to 4 carbon atoms, NR$^6$R$^7$, SR$^8$ or OR$^8$, $R^2$ represents hydrogen atom, $NR^9R^{10}$, $SR^{11}$, $OR^{11}$, an alkyl group of straight or branched chain having 1 to 6 carbon atoms, or a halogen atom, $R^3$ represents hydrogen atom, $NR^{12}R^{13}$, $SR^{14}$, $OR^{14}$, an alkyl group of straight or branched chain having 1 to 6 carbon atoms, or a halogen atom, $R^4$ and $R^5$ are identical or different and each represents a group selected from the group consisting of hydrogen atom, an alkyl group of straight or branched chain having 1 to 12 carbon atoms, a benzyl group, a cycloalkyl group having 3 to 10 carbon atoms and a phenyl group which may be substituted with 1 to 5 substituents that are selected from the group consisting of an alkyl group of straight or branched chain having 1 to 6 carbon atoms, an alkoxyl group of straight or branched chain having 1 to 4 carbon atoms, a halogen atom, a hydroxy group and an alkylenedioxy group having 1 or 2 carbon atoms; or $R^4$ and $R^5$, together with the nitrogen atom to which they are bonded, form a piperazine ring substituted with a phenyl group, or a tetrahydroquinoline ring, $R^6$, $R^7$ and $R^8$ are identical or different and each represents a group selected from the group consisting of hydrogen atom, and an alkyl group of straight or branched chain having 1 to 4 carbon atoms, $R^9$, $R^{10}$, $R^{11}$, $R^{12}$, $R^{13}$ and $R^{14}$ are identical or different and each represents a group selected from the group consisting of hydrogen atom, a phenyl group, a benzyl group, and an alkyl group of straight or branched chain having 1 to 10 carbon atoms, or $R^9$ and $R^{10}$, or $R^{12}$ and $R^{13}$, together with the nitrogen atom to which they are bonded, each form a morpholine ring, or a piperazine ring which may be substituted with an alkyl group of straight or branched chain having 1 to 4 carbon atoms, and n represents an integer from 1 to 6, provided that when n is 1 and $R^1$ is a methyl or $NH_2$ group, then at least one of $R^2$ and $R^3$ is not a methyl or ethyl group; and when n is 2, both $R^2$ and $R^3$ are not simultaneously methyl groups.

2. The pyrimidine derivative or salt thereof as claimed in claim 11, wherein $R^2$ represents $NR^9R^{10}$ or an alkyl group of straight or branched chain having 1 to 6 carbon atoms, $R^3$ represents $SR^{14}$, $OR^{14}$ or an alkyl group of straight or branched chain having 1 to 6 carbon atoms, $R^4$ and $R^5$ are identical or different and each represents a group selected from the group consisting of an alkyl group of straight or branched chain having 1 to 12 carbon atoms, a cycloalkyl group having 3 to 10 carbon atoms, a benzyl group and a phenyl group which may be substituted with 1 or 2 substituents that are selected from the group consisting of an alkyl group of straight or branched chain having 1 to 6 carbon atoms, an alkoxyl group of straight or branched chain having 1 to 4 carbon atoms, a halogen atom, a hydroxy group and an alkylenedioxy group having 1 to 2 carbon atoms; or $R^4$ and $R^5$, together with the nitrogen atom to which they are bonded, form a piperazine ring substituted with a phenyl group, or a tetrahydroquinoline ring.

3. The pyrimidine derivative or salt thereof as claimed in claim 2, wherein $R^3$ represents $SR^{14}$, $R^4$ represents an alkyl group of straight or branched chain having 3 to 10 carbon atoms or a cycloalkyl group having 3 to 10 carbon atoms, $R^5$ represents a benzyl group, or a phenyl group which may be substituted with 1 or 2 substituents that are selected from the group consisting of an alkyl group of straight or branched chain having 1 to 6 carbon atoms, an alkoxyl group of straight or branched chain having 1 to 4 carbon atoms, a halogen atom, a hydroxy group and an alkylenedioxy group having 1 or 2 carbon atoms; $R^9$ and $R^{10}$ are identical or different and each represents a group selected from the group consisting of an alkyl group of straight chain having 1 to 7 carbon atoms, a phenyl group, a benzyl group, or $R^9$ and $R^{10}$, together with the nitrogen atom to which they are bonded, form a morpholine ring, $R^{14}$ represents a hydrogen atom, an alkyl group of straight or branched chain having 1 to 6 carbon atoms or a benzyl group, and n represents an integer of 3 or 4.

4. The pyrimidine derivative or salt thereof as claimed in claim 3, wherein $R^5$ represents a phenyl group which may be substituted with 1 or 2 substituents that are selected from the group consisting of an alkyl group of straight or branched chain having 1 to 6 carbon atoms, an alkoxyl group of straight or branched chain having 1 to 4 carbon atoms, a halogen atom, a hydroxy group and an alkylenedioxy group having 1 or 2 carbon atoms, $R^9$ and $R^{10}$ identically represent ethyl groups, propyl groups or butyl groups, or $R^9$ represents a heptyl group and $R^{10}$ represents a benzyl group, or $R^9$ represents a phenyl group and $R^{10}$ represents a propyl group, or $R^9$ and $R^{10}$, together with the nitrogen atom to which they are bonded, form a morpholine ring.

5. The pyrimidine derivative or salt thereof as claimed in claim 2, wherein $R^2$ represents $NR^9R^{10}$, $R^3$ represents $OR^{14}$, $R^4$ represents an alkyl group of straight or branched chain having 3 to 10 carbon atoms, $R^5$ represents a phenyl group which may be substituted with 1 or 2 substituents that are selected from the group consisting of an alkyl group of straight or branched chain having 1 to 6 carbon atoms, an alkoxyl group of straight or branched chain having 1 to 4 carbon atoms, a halogen atom, a hydroxy group and an alkylenedioxy group having 1 or 2 carbon atoms; $R^9$, $R^{10}$ and $R^{14}$ are identical or different and each represents an alkyl group of straight or branched chain having 1 to 4 carbon atoms, and n represents an integer of 3 or 4.

6. The pyrimidine derivative or salt thereof as claimed in claim 11, wherein $R^1$ represents $NR^6R^7$, $SR^9$ or $OR^8$, $R^2$ represents $NR^9R^{10}$ or an alkyl group of straight or branched chain having 1 to 6 carbon atoms, $R^3$ represents $SR^{14}$, $OR^{14}$ or an alkyl group of straight or branched chain having 1 to 6 carbon atoms, $R^4$ and $R^5$ are identical or different and each represents a group selected from the group consisting of an alkyl group of straight or branched chain having 1 to 12 carbon atoms, a cycloalkyl group having 3 to 10 carbon atoms, a benzyl group and a phenyl group which may be substituted with 1 or 2 substituents that are selected from the group consisting of an alkyl group of straight or branched chain having 1 to 6 carbon atoms, an alkoxyl group of straight or branched chain having 1 to 4 carbon atoms, a halogen atom, a hydroxy group and an alkylenedioxy group having 1 or 2 carbon atoms; or $R^4$ and $R^5$, together with the nitrogen atom to which they are bonded, form a piperazine ring substituted with a phenyl group, or a tetrahydroquinoline ring.

7. The pyrimidine derivative or salt thereof as claimed in claim 6, wherein $R^2$ represents $NR^9R^{10}$, $R^3$ represents $SR^{14}$ or $OR^{14}$, $R^4$ represents an alkyl group of straight or branched chain having 3 to 10 carbon atoms, $R^5$ represents a phenyl group which may be substituted with 1 or 2 substituents that are selected from the group consisting of an alkyl group of straight or branched chain having 1 to 6 carbon atoms, an alkoxyl group of straight or branched chain having 1 to 4 carbon atoms, a halogen atom, a hydroxy group and an alkylenedioxy group having 1 or 2 carbon atoms, $R^6$, $R^7$, $R^8$, $R^9$, $R^{10}$ and $R^{14}$ are identical or different and each represents an alkyl group of straight or branched chain having 1 to 4 carbon atoms, and n represents an integer of 3 or 4.

8. A pharmaceutical composition which comprises a pharmaceutically acceptable carrier and an effective amount of at least one pyrimidine derivative represented by the formula (I) or a salt thereof:

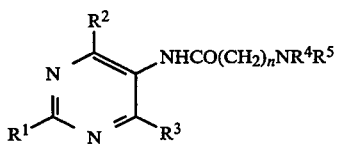

(I)

wherein $R^1$ represents hydrogen atom, an alkyl group of straight or branched chain having 1 to 4 carbon atoms, $NR^6R^7$, $SR^8$ or $OR^8$, $R^2$ represents hydrogen atom, $NR^9R^{10}$, $SR^{11}$, $OR^{11}$, an alkyl group of straight or branched chain having 1 to 6 carbon atoms, or a halogen atom, $R^3$ represents hydrogen atom, $NR^{12}R^{13}$, $SR^{14}$, $OR^{14}$, an alkyl group of straight or branched chain having 1 to 6 carbon atoms, or a halogen atom, $R^4$ and $R^5$ are identical or different and each represents a group selected from the group consisting of hydrogen atom, an alkyl group of straight or branched chain having 1 to 12 carbon atoms, a benzyl group, a cycloalkyl group having 3 to 10 carbon atoms and a phenyl group which may be substituted with 1 to 5 substituents that are selected from the group consisting of an alkyl group of straight or branched chain having 1 to 6 carbon atoms, an alkoxyl group of straight or branched chain having 1 to 4 carbon atoms, a halogen atom, a hydroxy group and an alkylenedioxy group having 1 or 2 carbon atoms; or $R^4$ and $R^5$, together with the nitrogen atom to which they are bonded, form a piperazine ring substituted with a phenyl group, or a tetrahydroquinoline ring, $R^6$, $R^7$ and $R^8$ are identical or different and each represents a group selected from the group consisting of hydrogen atom, and an alkyl group of straight or branched chain having 1 to 4 carbon atoms, $R^9$, $R^{10}$, $R^{11}$, $R^{12}$, $R^{13}$ and $R^{14}$ are identical or different and each represents a group selected from the group consisting of hydrogen atom, a phenyl group, a benzyl group, and an alkyl group of straight or branched chain having 1 to 10 carbon atoms, or $R^9$ and $R^{10}$, or $R^{12}$ and $R^{13}$, together with the nitrogen atom to which they are bonded, each form a morpholine ring, or a piperazine ring which may be substituted with an alkyl group of straight or branched chain having 1 to 4 carbon atoms, and n represents an integer from 1 to 6, provided that when n is 1 and $R^1$ is a methyl or $NH_2$ group, then at least one of $R^2$ and $R^3$ is not a methyl or ethyl group; and when n is 2, both $R^2$ and $R^3$ are not simultaneously methyl groups.

9. A pyrimidine derivative represented by the formula (I) or a salt thereof:

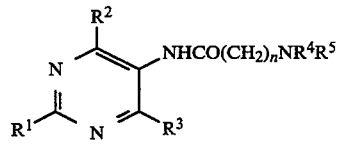

(I)

wherein $R^1$ represents hydrogen atom, an alkyl group of straight or branched chain having 1 to 4 carbon atoms, $NR^6R^7$, $SR^8$ or $OR^8$, $R^2$ represents hydrogen atom, $NR^9R^{10}$, $SR^{11}$, $OR^{11}$, an alkyl group of straight or branched chain having 1 to 6 carbon atoms, or a halogen atom, $R^3$ represents hydrogen atom, $NR^{12}R^{13}$, $SR^{14}$, $OR^{14}$, an alkyl group of straight or branched chain having 1 to 6 carbon atoms, or a halogen atom, $R^4$ and $R^5$ are identical or different and each represents a group selected from the group consisting of hydrogen atom, an alkyl group of straight or branched chain having 1 to 12 carbon atoms, a benzyl group, a cycloalkyl group having 3 to 10 carbon atoms and a phenyl group which may be substituted with 1 to 5 substituents that are selected from the group consisting of an alkyl group of straight or branched chain having 1 to 6 carbon atoms, an alkoxyl group of straight or branched chain having 1 to 4 carbon atoms, a halogen atom, a hydroxy group and an alkylenedioxy group having 1 or 2 carbon atoms; or $R^4$ and $R^5$, together with the nitrogen atom to which they are bonded, form a piperazine ring substituted with a phenyl group, or a tetrahydroquinoline ring, $R^6$, $R^7$ and $R^8$ are identical or different and each represents a group selected from the group consisting of hydrogen atom, and an alkyl group of straight or branched chain having 1 to 4 carbon atoms, $R^9$ and $R^{10}$, $R^{11}$, $R^{12}$, $R^{13}$ and $R^{14}$ are identical or different and each represents a group selected from the group consisting of hydrogen atom, a phenyl group, a benzyl group, and an alkyl group of straight or branched chain having 1 to 10 carbon atoms, or $R^9$ and $R^{10}$, or $R^{12}$ and $R^{13}$, together with the nitrogen atom to which they are bonded, each form a morpholine ring, or a piperazine ring which may be substituted with an alkyl group of straight or branched chain having 1 to 4 carbon atoms, and n represents an integer from 2 to 6, provided that when n is 2, both $R^2$ and $R^3$ are not simultaneously methyl groups.

10. A pharmaceutical composition which comprises a pharmaceutically acceptable carrier and an effective amount of at least one selected from a pyrimidine derivative represented by the formula (I) or a salt thereof:

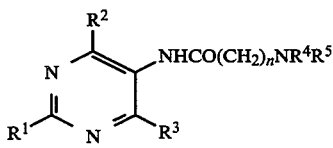

(I)

wherein $R^1$ represents hydrogen atom, an alkyl group of straight or branched chain having 1 to 4 carbon atoms, $NR^6R^7$, $SR^8$ or $OR^8$, $R^2$ represents hydrogen atom, $NR^9R^{10}$, $SR^{14}$, $OR^{14}$, an alkyl group of straight or branched chain having 1 to 6 carbon atoms, or a halogen atom, $R^3$ represents hydrogen atoms, $NR^{12}R^{13}$, $SR^{14}$, $OR^{14}$, an alkyl group of straight or branched chain having 1 to 6 carbon atoms, or a halogen atom, $R^4$ and $R^5$ are identical or different and each represents a group selected from the group consisting of hydrogen atom, an alkyl group of straight or branched chain having 1 to 12 carbon atoms, a benzyl group, a cycloalkyl group having 3 to 10 carbon atoms and a phenyl group which may be substituted with 1 to 5 substituents that are selected from the group consisting of an alkyl group of straight or branched chain having 1 to 6 carbon atoms, an alkoxyl group of straight or branched chain having 1 to 4 carbon atoms, a halogen atom, a hydroxy group and an alkylenedioxy group having 1 or 2 carbon atoms; or $R^4$ and $R^5$, together with the nitrogen atom to which they are bonded, form a piperazine ring substituted with a phenyl group, or a tetrahydroquinoline ring, $R^6$, $R^7$ and $R^8$ are identical or different and each represents a group selected from the group consisting of hydrogen atom, and an alkyl group of straight or branched chain having 1 to 4 carbon atoms, $R^9$, $R^{10}$, $R^{11}$, $R^{12}$, $R^{13}$ and $R^{14}$ are identical or different and each represents a group selected from the group consisting of hydrogen atom, a phenyl group, a benzyl group, and an alkyl group of straight or branched chain having 1 to 10 carbon atoms, or $R^9$ and $R^{10}$, or $R^{12}$ and $R^{13}$, together with the nitrogen atom to which they are bonded, each form a morpholine ring, or a piperazine ring which may be substituted with an alkyl group of straight or branched chain having 1 to 4 carbon atoms, and n represents an integer from 2 to 6, provided that when n is 2, both $R^2$ and $R^3$ are not simultaneously methyl groups.

* * * * *

UNITED STATES PATENT AND TRADEMARK OFFICE
CERTIFICATE OF CORRECTION

PATENT NO. : 5,397,781
DATED : March 14, 1995
INVENTOR(S) : Kazutoshi YANAGIBASHI et al It is certified that error appears in the above-indentified patent and that said Letters Patent is hereby corrected as shown below:

In column 84, line 66, "$R^{10}$" should be --$R^1$--

In column 85, line 45, "claim 11" should be --claim 1--

In column 86, line 44, "claim 11" should be --claim 1--

Signed and Sealed this

Nineteenth Day of September, 1995

Attest:

BRUCE LEHMAN

Attesting Officer

Commissioner of Patents and Trademarks